US012790294B2

(12) United States Patent
Kaminski et al.

(10) Patent No.: US 12,790,294 B2
(45) Date of Patent: Nov. 10, 2026

(54) DEUTERATED FUNCTIONALIZED DERIVATIVES OF α-ALANINE, IN PARTICULAR FOR THE TREATMENT OF NEUROLOGICAL DISEASES

(71) Applicant: UNIWERSYTET JAGIELLONSKI, Cracow (PL)

(72) Inventors: Krzysztof Kaminski, Cracow (PL); Michal Abram, Cracow (PL); Rafal Kaminski, Warsaw (PL); Marcin Jakubiec, Wilkowice (PL)

(73) Assignee: UNIWERSYTET JAGIELLONSKI, Cracow (PL)

( * ) Notice: Subject to any disclaimer, the term of this patent is extended or adjusted under 35 U.S.C. 154(b) by 247 days.

(21) Appl. No.: 18/711,775

(22) PCT Filed: Nov. 24, 2022

(86) PCT No.: PCT/PL2022/050083
§ 371 (c)(1),
(2) Date: May 20, 2024

(87) PCT Pub. No.: WO2023/096512
PCT Pub. Date: Jun. 1, 2023

(65) Prior Publication Data

US 2025/0042848 A1 Feb. 6, 2025

(30) Foreign Application Priority Data

Nov. 24, 2021 (PL) ........................................ 439639

(51) Int. Cl.
*C07D 207/12* (2006.01)
*A61K 31/402* (2006.01)
*A61K 31/497* (2006.01)
*A61P 25/08* (2006.01)
*C07B 59/00* (2006.01)
*C07D 241/04* (2006.01)

(52) U.S. Cl.
CPC .......... *C07D 207/12* (2013.01); *A61K 31/402* (2013.01); *A61K 31/497* (2013.01); *A61P 25/08* (2018.01); *C07B 59/004* (2013.01); *C07D 241/04* (2013.01); *C07B 2200/05* (2013.01)

(58) Field of Classification Search
CPC .................................................... C07D 207/12
See application file for complete search history.

(56) References Cited

FOREIGN PATENT DOCUMENTS

WO 2020145831 A1 7/2020
WO 2020214043 A1 10/2020

OTHER PUBLICATIONS

Shao et al. The kinetic isotope effect in the search for deuterated drugs, Drug News and Perspectives, 2010, 23(6), 398-404.

*Primary Examiner* — Golam M Shameem
(74) *Attorney, Agent, or Firm* — Mintz Levin Cohn Ferris Glovsky and Popeo PC

(57) ABSTRACT

A group of chemical compounds has been disclosed, especially for the treatment of neurological diseases, which are modified alanine derivatives whose structures has been designed based on the bioisosteric and selective replacement of hydrogen atoms with deuterium.

22 Claims, 19 Drawing Sheets

1

2

State of the art $d_5$-(*R*)-3

$d_3$-(*R*)-8

Structures of compounds **$d_5$-(*R*)-3 and $d_3$-(*R*)-8** - comparative examples.

DEUTERATED FUNCTIONALIZED DERIVATIVES OF α-ALANINE, IN PARTICULAR FOR THE TREATMENT OF NEUROLOGICAL DISEASES

CROSS-REFERENCE TO RELATED APPLICATIONS

This application is a U.S. National Phase Application of PCT/PL2022/050083, filed on Nov. 24, 2022, which claims priority to a Polish Patent Application Serial No. P.439639 filed on Nov. 24, 2021, all of which are hereby incorporated by reference in their entirety to the extent permitted.

Field

The invention relates to chemical compounds that are, from structural point of view, modified (functionalized) derivatives of alanine, the structures of which were designed based on bioisosteric and selective replacement of hydrogen atoms with its stable isotope—deuterium. These compounds are intended for the treatment of, in particular, neurological diseases (especially epilepsy and neuropathic pain), and in relation to parent molecules substituted with hydrogen atoms they are characterized by distinctly more favorable pharmacokinetic properties in mice, i.e. they have a significantly longer biological half-life ($t_{0.5}$) in plasma and brain, they are eliminated from the body more slowly and have a distinctly more favorable absorption profile (bioavailability) from the site of administration (peritoneal or gastrointestinal tract). Therefore, selected deuterated derivatives which are the object of the present invention can be used as active ingredients of medicinal formulations used in particular in the treatment of neurological diseases. The more favorable pharmacokinetic profile of the disclosed deuterated compounds in relation to analogues containing hydrogen in their structure makes them potentially more promising candidates for preclinical and clinical development.

STATE OF THE ART

Previous studies performed in series of functionalized amino acid derivatives have revealed particularly favorable pharmacological properties and an above-average safety margin for compounds with the R-configuration of the stereogenic center, in which the central fragment of the molecule is formed by D(R)-alanine, the amino group of which has been incorporated into a pyrrolidine-2,5-dione ring, and the carboxyl moiety converted into a benzylamide moiety (preferably with unsubstituted aromatic ring or with fluorine atom at the 2-position). These compounds are disclosed in patent applications P.429656, PCT/PL2020/050028, and patent Pat.240297, and their structures are shown in FIG. 1.

The presented compounds show broad spectrum of anticonvulsant activity in animal models of seizures, which was confirmed in studies on mice and rats. Compound 1 has also been shown to be effective in models of neuropathic pain and a model of depression and anxiety in mice, as well as having neuroprotective and neurotrophic effects in vitro. A unique feature of compounds 1 and 2 is minimal effect on mouse motor coordination in the rotarod test, no sedative effect in spontaneous locomotor activity test on mice, no interaction with the CYP3A4 and CYP2D9 isoforms of cytochrome P-450 and very high metabolic stability on human microsomes. Considering the above facts, the disclosed substances, and in particular compound 1, is a promising candidate for a drug used in the treatment of various types of epilepsy (including drug-resistant epilepsy), epilepsy with accompanying affective diseases/disorders, i.e. depression and anxiety, neuropathic pain, neurodegenerative diseases (including Alzheimer's disease, Parkinson's disease, amyotrophic lateral sclerosis, etc.).

Despite the extremely promising pharmacological properties, the application potential of the above-mentioned substances is slightly reduced by the relatively short biological half-life ($t_{0.5}$) after their intraperitoneal (i.p.) administration to mice, which is approximately 47 minutes (20 mg/kg dose) and 56 minutes (40 mg/kg dose) in serum and 57 minutes (20 mg/kg dose) and 75 minutes (40 mg/kg dose) in the brain for compound 1. For compound 2, these values were as follow, 34 minutes (20 mg/kg dose) and 33 minutes (40 mg/kg dose) in serum and 34 minutes (20 mg/kg dose) and 38 minutes (40 mg/kg dose) in brain (see Tables 1-4). These results may necessitate administration of the substance several times a day to a person. As a result, the above-mentioned dosing regimen, i.e. multiple application of the drug during the day, may contribute to the patient's non-compliance or poor compliance with the planned pharmacotherapy, which may lead to a decrease of treatment efficacy . . .

Considering the above facts, the technical problem that the present invention solves is to provide analogues of compounds 1 and 2 disclosed in patent applications P.429656, PCT/PL2020/050028, and patent Pat.240297, and in particular compound 1, with more favorable pharmacokinetic parameters, characterized by, in particular, a longer plasma and brain biological half-life ($t_{0.5}$) of at least 80 minutes and still possessing similar, potent and broad-based anticonvulsant activity as parent molecules 1 and 2 in studies performed in vivo (in mice).

SUMMARY OF THE INVENTION

The object of the invention are deuterated derivatives of N-benzyl-2-(2,5-dioxopyrrolidin-1-yl)propanamide depicted on the general formula (I):

(I)

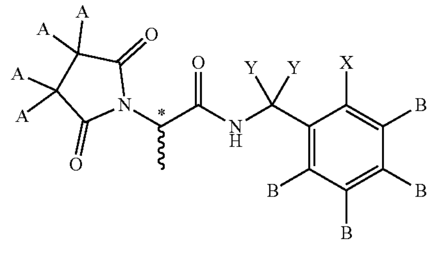

where:

A is hydrogen or deuterium, wherein at least one A is deuterium,

B is hydrogen or deuterium,

X is hydrogen or deuterium or fluorine,

Y is hydrogen or deuterium.

Preferably, X is hydrogen or fluorine, particularly preferably fluorine.

Preferably, each A is deuterium.

Particularly preferably, when each A is deuterium, each B and X are also deuterium.

Preferably, each Y is deuterium.

In a preferred embodiment, the object of the invention is deuterated N-benzyl-2-(2,5-dioxopyrrolidin-1-yl)propanamide derivative selected from:

(R)—N-benzyl-2-(2,5-dioxopyrrolidin-1-yl-3,3,4,4-$d_4$) propanamide (compound $d_4$-(R)-1, where A=D, B=H, X=H, Y=H), (R)-2-(2,5-dioxopyrrolidin-1-yl-3,3,4,4-$d_4$)-N-((phenyl-$d_5$)methyl)propanamide (compound $d_9$-(R)-2, where A=D, B=D, X=D, Y=H), (R)-2-(2,5-dioxopyrrolidin-1-yl-3,3,4,4-$d_4$)-N-(2-fluorobenzyl)propanamide (compound $d_4$-(R)-4, where A=D, B=H, X=F, Y=H), (R)-2-(2,5-dioxopyrrolidin-1-yl-3,3,4,4-$d_4$)-N-(phenylmethyl-$d_2$)propanamide (compound $d_6$-(R)-5, where A=D, B=H, X=H, Y=D), (R)-2-(2,5-dioxopyrrolidin-1-yl-3,3,4,4-$d_4$)-N-((phenyl-$d_5$)methyl-$d_2$)propanamide (compound $d_{11}$-(R)-6: A=D, B=D, X=D, Y=D), (R)-2-(2,5-dioxopyrrolidin-1-yl-3,3,4,4-$d_4$)-N-((2-fluorophenyl)methyl-$d_2$)propanamide (compound $d_6$-(R)-7, where A=D, B=H, X=F, Y=D), (S)—N-benzyl-2-(2,5-dioxopyrrolidin-1-yl-3,3,4,4-$d_4$) propanamide (compound $d_4$-(S)-1, where A=D, B=H, X=H, Y=H), (S)-2-(2,5-dioxopyrrolidin-1-yl-3,3,4,4-$d_4$)-N-((phenyl-$d_5$)methyl)propanamide (compound $d_9$-(S)-2, where A=D, B=D, X=D, Y=H), (S)-2-(2,5-dioxopyrrolidin-1-yl-3,3,4,4-$d_4$)-N-(2-fluorobenzyl)propanamide (compound $d_4$-(S)-4, where A=D, B=H, X=F, Y=H), (S)-2-(2,5-dioxopyrrolidin-1-yl-3,3,4,4-$d_4$)-N-(phenylmethyl-$d_2$)propanamide (compound $d_6$-(S)-5, where A=D, B=H, X=H, Y=D), (S)-2-(2,5-dioxopyrrolidin-1-yl-3,3,4,4-$d_4$)-N-((phenyl-$d_5$)methyl-$d_2$)propanamide (compound $d_{11}$-(S)-6, where A=D, B=D, X=D, Y=D), (S)-2-(2,5-dioxopyrrolidin-1-yl-3,3,4,4-$d_4$)-N-((2-fluorophenyl)methyl-$d_2$)propanamide (compound $d_6$-(S)-7, where A=D, B=H, X=F, Y=D), (R,S)—N-benzyl-2-(2,5-dioxopyrrolidin-1-yl-3,3,4,4-$d_4$) propanamide (compound $d_4$-(R,S)-1, where A=D, B=H, X=H, Y=H), (R,S)-2-(2,5-dioxopyrrolidin-1-yl-3,3,4,4-$d_4$)-N-((phenyl-$d_5$)methyl)propanamide (compound $d_9$-(R,S)-2, where A=D, B=D, X=D, Y=H), (R,S)-2-(2,5-dioxopyrrolidin-1-yl-3,3,4,4-$d_4$)-N-(2-fluorobenzyl)propanamide (compound $d_4$-(R,S)-4, where A=D, B=H, X=F, Y=H), (R,S)-2-(2,5-dioxopyrrolidin-1-yl-3,3,4,4-$d_4$)-N-(phenylomethyl-$d_2$)propanamide (compound $d_6$-(R,S)-5, where A=D, B=H, X=H, Y=D), (R,S)-2-(2,5-dioxopyrrolidin-1-yl-3,3,4,4-$d_4$)-N-((phenyl-$d_5$) methyl-$d_2$)propanamide (compound $d_{11}$-(R,S)-6, where A=D, B=D, X=D, Y=D), (R,S)-2-(2,5-dioxopyrrolidin-1-yl-3,3,4,4-$d_4$)-N-((2-fluorophenyl)methyl-$d_2$)propanamide (compound $d_6$-(R,S)-7, where A=D, B=H, X=F, Y=D).

These compounds are shown in the following scheme:

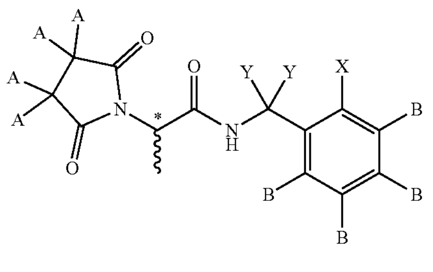

-continued

Compound $d_4$-(R)-1: A = D, B = H, X = H, Y = H
Compound $d_9$-(R)-2: A = D, B = D, X = D, Y = H
Compound $d_4$-(R)-4: A = D, B = H, X = F, Y = H
Compound $d_4$-(S)-1: A = D, B = H, X = H, Y = H
Compound $d_9$-(S)-2: A = D, B = D, X = D, Y = H
Compound $d_4$-(S)-4: A = D, B = H, X = F, Y = H
Compound $d_4$-(R,S)-1: A = D, B = H, X = H, Y = H
Compound $d_9$-(R,S)-2: A = D, B = D, X = D, Y = H
Compound $d_4$-(R,S)-4: A = D, B = H, X = F, Y = H
Compound $d_6$-(R)-5: A = D, B = H, X = H, Y = D
Compound $d_{11}$-(R)-6: A = D, B = D, X = D, Y = D
Compound $d_6$-(R)-7: A = D, B = H, X = F, Y = D
Compound $d_6$-(S)-5: A = D, B = H, X = H, Y = D
Compound $d_{11}$-(S)-6: A = D, B = D, X = D, Y = D
Compound $d_6$-(S)-7: A = D, B = H, X = F, Y = D
Compound $d_6$-(R,S)-5: A = D, B = H, X = H, Y = D
Compound $d_{11}$-(R,S)-6: A = D, B = D, X = D, Y = D
Compound $d_6$-(R,S)-7: A = D, B = H, X = F, Y = D Particularly preferably, the compound according to the invention is selected from the group consisting of N-benzyl-2-(2,5-dioxopyrrolidin-1-yl)propanamide derivatives with the R-configuration of the stereogenic center at C-2 and also containing deuterium, especially in position A in the general formula (I):

(R)—N-benzyl-2-(2,5-dioxopyrrolidin-1-yl-3,3,4,4-$d_4$) propanamide (compound $d_4$-(R)-1, where A=D, B=H, X=H, Y=H), (R)-2-(2,5-dioxopyrrolidin-1-yl-3,3,4,4-$d_4$)-N-((phenyl-$d_5$)methyl)propanamide (compound $d_9$-(R)-2, where A=D, B=D, X=D, Y=H), (R)-2-(2,5-dioxopyrrolidin-1-yl-3,3,4,4-$d_4$)-N-(2-fluorobenzyl)propanamide (compound $d_4$-(R)-4, where A=D, B=H, X=F, Y=H), (R)-2-(2,5-dioxopyrrolidin-1-yl-3,3,4,4-$d_4$)-N-(phenylmethyl-$d_2$)propanamide (compound $d_6$-(R)-5, where A=D, B=H, X=H, Y=D), (R)-2-(2,5-dioxopyrrolidin-1-yl-3,3,4,4-$d_4$)-N-((phenyl-$d_5$)methyl-$d_2$)propanamide (compound $d_{11}$-(R)-6: A=D, B=D, X=D, Y=D), (R)-2-(2,5-dioxopyrrolidin-1-yl-3,3,4,4-$d_4$)-N-((2-fluorophenyl)methyl-$d_2$)propanamide (compound $d_6$-(R)-7, where A=D, B=H, X=F, Y=D).

In pharmacokinetic studies performed in mice after intraperitoneal (i.p.) administration, the compound $d_4$-(R)-1 according to the invention containing 4 deuterium atoms in the imide ring (A=D), $d_9$-(R)-2 containing 9 deuterium atoms, including 4 in the imide ring and 5 in the aromatic ring (A=D, B=D, X=D), $d_6$-(R)-5 with 6 deuterium atoms in the succinimide and methylene bridge (A=D, Y=D) and $d_{11}$-(R)-6 with 11 deuterium atoms (A=D, B=D, X=D, Y=D), were characterized by a much slower elimination at both doses, i.e. 20 and 40 mg/kg, both from serum and the brain of the tested animals, as supported by the significantly longer (approx. 1.5-3 times) biological half-life ($t_{0.5}$) of these compounds in plasma, and especially in the brain, compared to the parent derivative 1 (Tables 1-4), containing hydrogen atoms in position A, B, X, and Y. In all cases, the $t_{0.5}$ values were above the minimum desired value of 80 minutes. A similar and very beneficial effect of extending $t_{0.5}$ by incorporating a different number of deuterium atoms into the structure was observed for compounds $d_4$-(R)-4 and $d_6$-(R)-7, which are bioisosteres of the parent compound 2. Notably, from the point of view of the activity in the central nervous system, the effect of extending $t_{0.5}$ (approx. 4 times)

was particularly visible in the brain of the tested animals. What is not obvious, a similar degree of extension of $t_{0.5}$ was not observed in the case of compound $d_5$-(R)-3 containing 5 deuterium atoms in the aromatic ring and compound $d_3$-(R)-8 containing 3 deuterium atoms in the side methyl group, which are negative examples. The structures of compounds $d_5$-(R)-3 and $d_3$-(R)-8 are shown in FIG. 2.

The obtained results prove that, in particular, the selective deuteration of the pyrrolidine-2,5-dione ring, i.e. incorporation of 4 deuterium atoms in place of 4 hydrogen atoms [position A in the general formula (I)], enables the extension of the biological half-life ($t_{0.5}$). Similarly, a favorable but slightly weaker effect was observed in the case of deuterium incorporation into the methylene bridge [position Y in general formula (I)]. The aforementioned influence of the selective deuterium replacement in the pyrrolidine-2,5-dione ring on the extension of $t_{0.5}$ is even more non-obvious when one considers the fact that both the parent compound 1 (FIG. 1) and the deuterated analogue $d_4$-(R)-1 described by the formula (I) according to the invention are also characterized by excellent metabolic stability on mouse microsomes in vitro, and the results obtained indicate that these substances are not metabolized in the aforementioned imide fragment (see FIG. 19). This may suggest that the extension of the $t_{0.5}$ caused by the selective incorporation of deuterium into the pyrrolidine-2,5-dione ring probably leads to decrease of phase II metabolic transformations, i.e. the coupling reaction (e.g. with glucuronic acid, glycine, etc.), inhibition of extrahepatic metabolism or reduction of excretion of unchanged drug from the body. The above-mentioned decrease of phase II metabolic transformations may hypothetically be the result of inhibiting the keto-enol tautomerism characteristic for imide derivatives (Valadbeigi, Y.; Farrokhpour, H. *Struct. Chem.* 2015, 26, 539-545), by eliminating "mobile" hydrogen atoms, which prevents the in vivo formation of the enol form susceptible to the coupling reaction. It is worth noting that the blocking of keto-enol tautomerism by the use of hydrogen/deuterium bioisosteric replacement has not been described in the literature so far, and it also seems impossible when at least one hydrogen atom is left in the ring [namely when at least one A=H in the general formula (I)].

Unexpectedly, the deuterated analogues of the parent compound 1, i.e. $d_4$-(R)-1 and $d_9$-(R)-2 according to the present invention, are characterized by significantly higher absorption after intraperitoneal administration, as well as better penetration into brain as evidenced by an increase in $AUC_{inf}$ parameters depending on the applied dose (20 or 40 mg/kg); i.e. 1.4-3.2-fold increase in plasma and 1.7-2.6-fold increase in brain. Unobviously, for derivatives $d_6$-(R)-5 and $d_{11}$-(R)-6, significant increases in $AUC_{inf}$ were noted in brain at both doses and only at the 40 mg/kg dose in plasma. It should be emphasized that the spectacular 4.4-5.3-fold (plasma) and 7.5-7.9-fold (brain) increase in $AUC_{inf}$ revealed deuterated analogues of compound 2, i.e. $d_4$-(R)-4 and $d_6$-(R)-7. A similar increase in AUC in the plasma and brain of tested animals was not observed for $d_5$-(R)-3, for which the determined $AUC_{inf}$ at a dose of 40 mg/kg was lower in plasma and only slightly higher in murine brain compared to the parent compound 1. Almost identical $AUC_{inf}$ values for plasma and brain were also obtained for $d_3$-(R)-8, which was tested exclusively at 40 mg/kg (data based on $AUC_{inf}$ values summarized in Tables 1-4).

The subsequent object of the invention is a compound according to the invention as defined above for use in pharmacy, especially in the treatment or prevention of neurological diseases, epilepsy, neurological pain, migraine, depression, anxiety, neurodegenerative disease or neuropathic pain. Preferably, the neurodegenerative disease is Parkinson's disease, Alzheimer's disease or amyotrophic lateral sclerosis.

FIGURES

In order to better explain the essence of the invention, its description is illustrated by the following figures.

Figure 13:
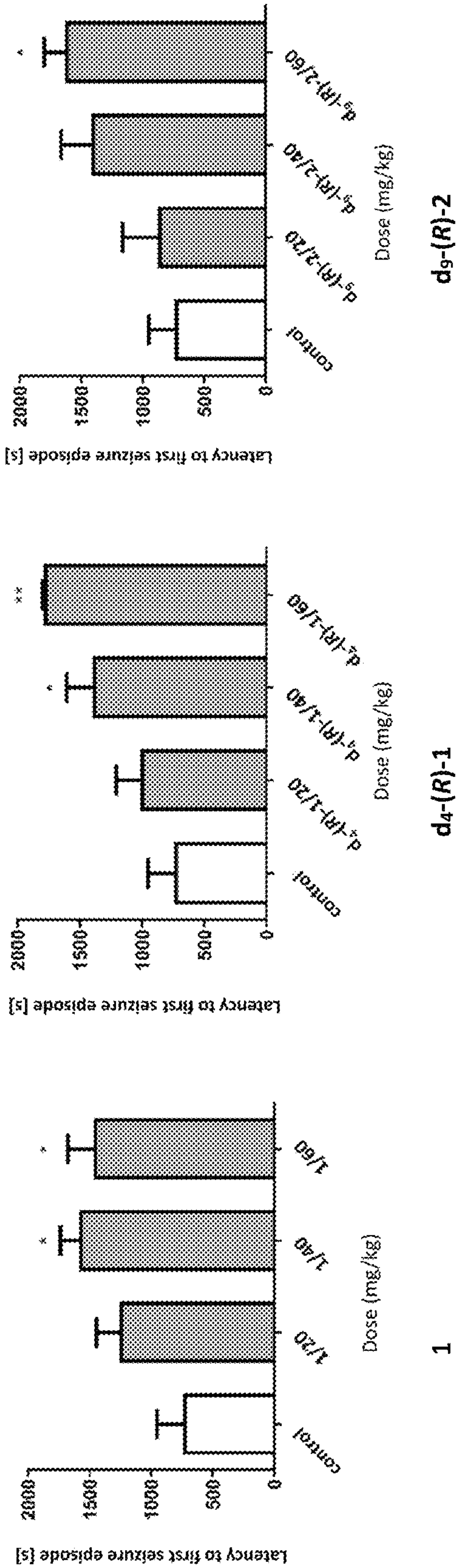

FIG. 13 shows the effect of tested compound 1 and deuterated derivatives $d_4$-(R)-1, $d_9$-(R)-2 on the latency of the first episode of clonic seizures in the scPTZ test. Results are presented as means±SEM (6 mice per group). Statistical analysis: one-way analysis of variance (ANOVA), followed by Dunnett's post hoc test: *p<0.05, **p<0.01.

Figure 14:
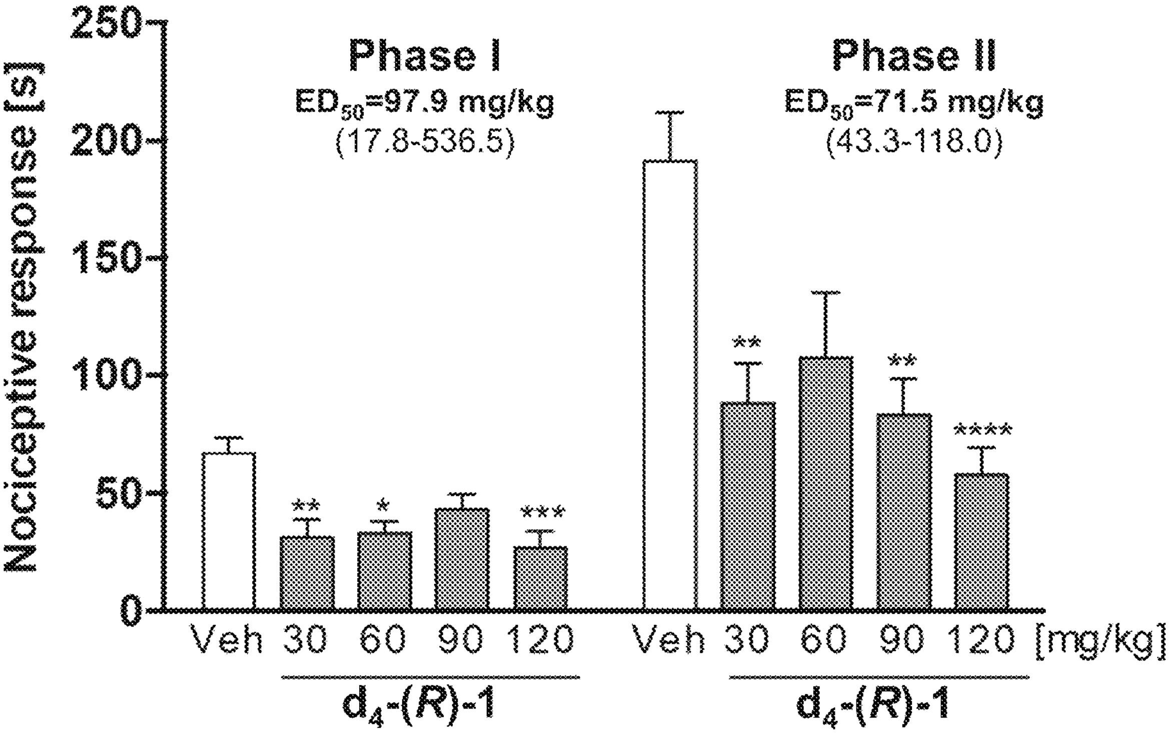

FIG. 14 shows the antinociceptive activity of compound $d_4$-(R)-1 in phase I and II of the formalin test. The results are presented as paw licking time in the first phase of the test (0-5 minutes after formalin injection) and in second phase of the test (15-30 minutes after formalin injection). The values represent means±SEM for a group of 8-10 animals. Statistically significant difference in comparison to the control group (Veh) given vehicle alone (1% aqueous solution of Tween 80). One-way analysis of variance (ANOVA), followed by Dunnett's post hoc test: *p<0.05, p<0.01, *p<0.001, ****p<0.0001.

Figure 15:
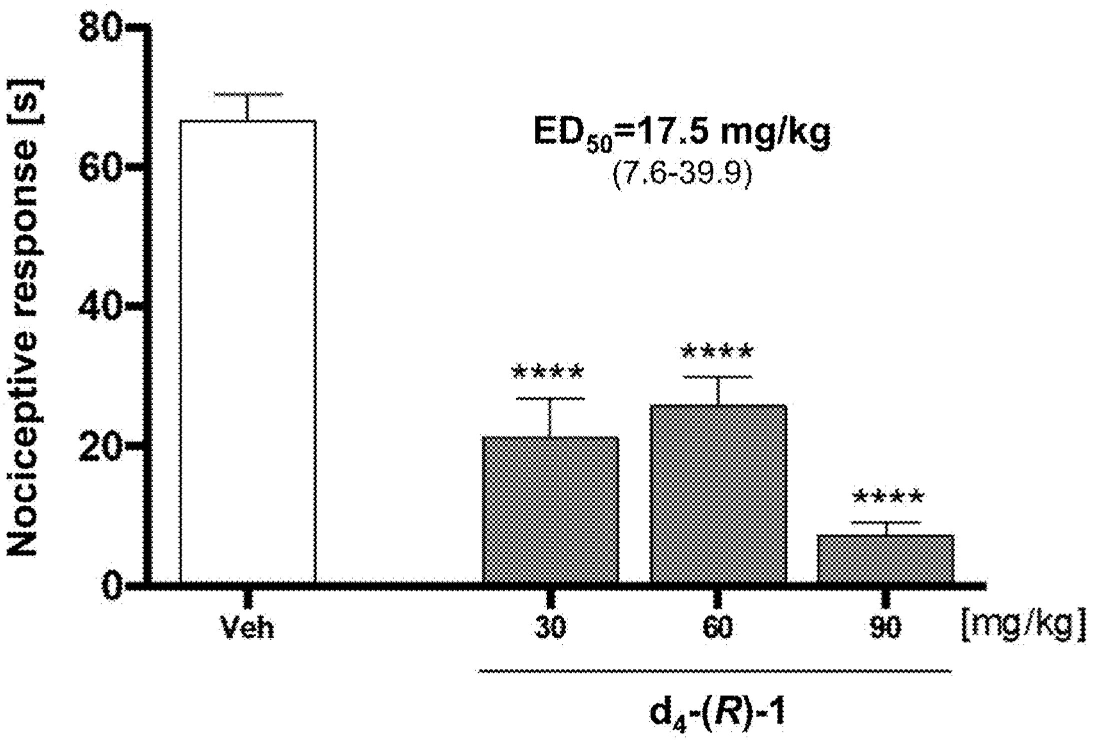

FIG. 15 shows the antinociceptive activity of compound $d_4$-(R)-1 in the capsaicin test, where the results are shown as paw licking time in 5 minutes period after capsaicin injection. The values represent means±SEM for a group of 8-10 animals; statistically significant difference in comparison to the control group (Veh) given vehicle alone (1% aqueous solution of Tween 80)—one-way analysis of variance (ANOVA), followed by Dunnett's post hoc test: ****p<0.0001.

Figure 16:
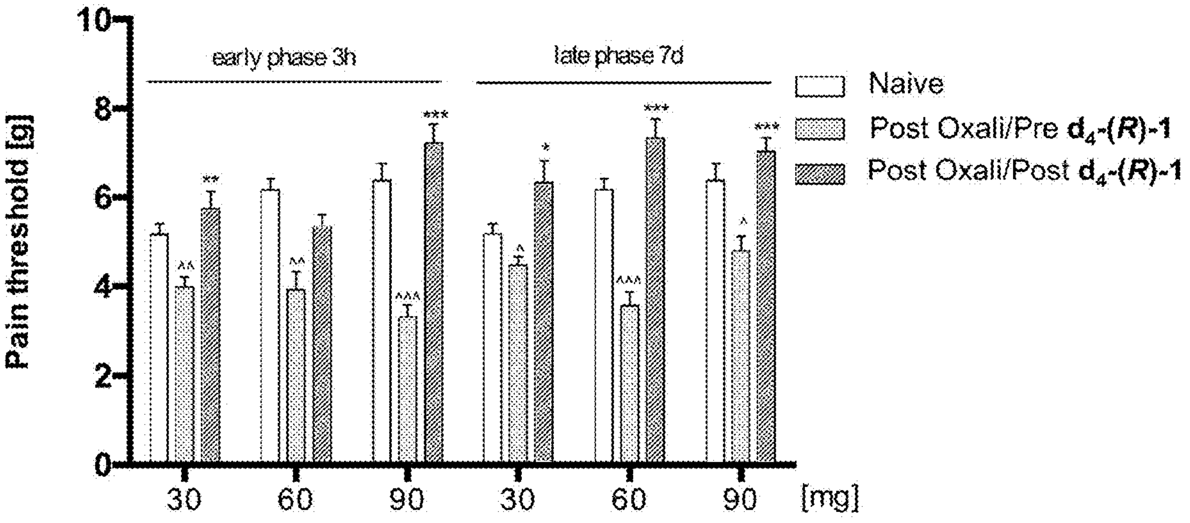

FIG. 16 shows the antinociceptive activity of compound $d_4$-(R)-1 in an oxaliplatin-induced neuropathic pain model. The results represent pain threshold in response to mechanical allodynia in the von Frey test 30 minutes after compound administration. The values represent means±SEM for a group of 8-10 animals. Statistically significant difference in comparison to the group given oxaliplatin alone, one-way repeated-measures analysis of variance (ANOVA), followed by Dunnett's post hoc test: *p<0.05, p<0.01, *p<0.001. Statistically significant difference in comparison to the group of healthy animals: /\p<0.05, /\/\p<0.01 /\/\/\p<0.001 (one-way repeated-measures analysis of variance (ANOVA), followed by Dunnett's post hoc test).

Figure 17:
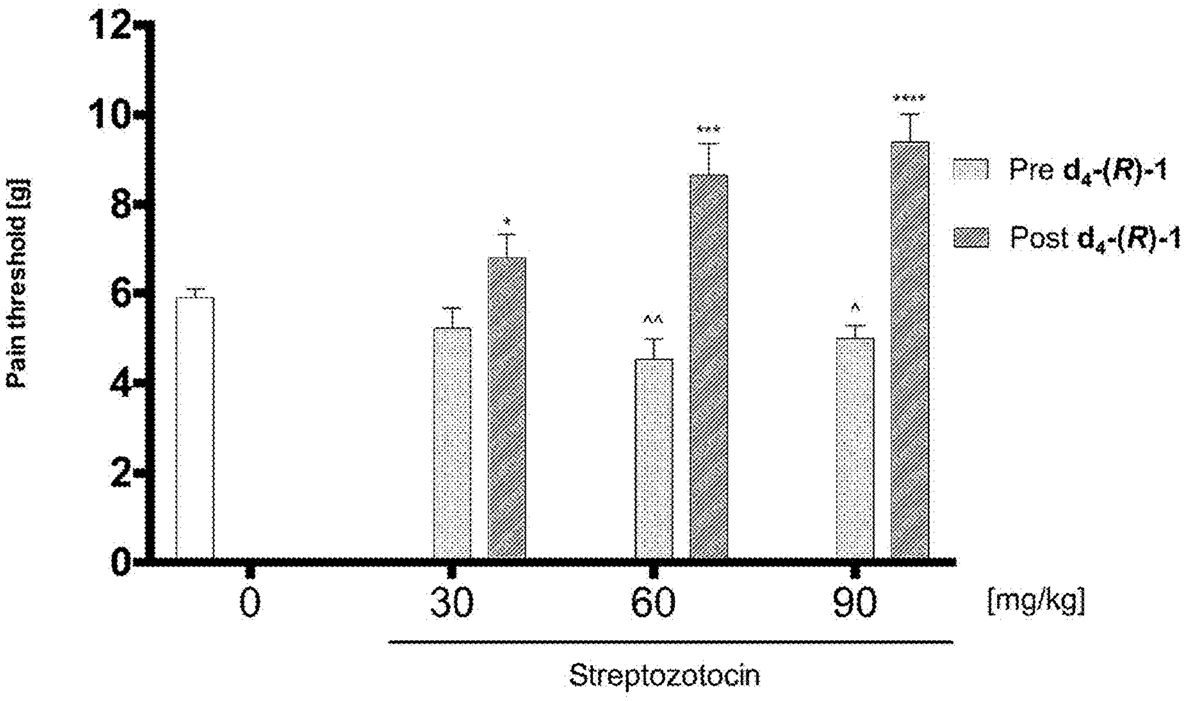

FIG. 17 shows the antinociceptive activity of compound $d_4$-(R)-1 in a streptozotocin-induced model of painful diabetic neuropathy. The results represent pain threshold in response to mechanical allodynia in the von Frey test 30 minutes after compound administration. The control group (0) was given vehicle (1% aqueous solution of Tween 80). The values represent means±SEM for a group of 8-10 animals. Statistically significant difference in comparison to group given STZ alone: *p<0.05, *p<0.001, **p<0.0001 (one-way repeated-measures analysis of variance (ANOVA), followed by Bonferroni post hoc test). Statistically significant difference in comparison to the control group (one-way analysis of variance (ANOVA), followed by Dunnett's post hoc test): /\p<0.05, /\/\p<0.01.

Figure 18:
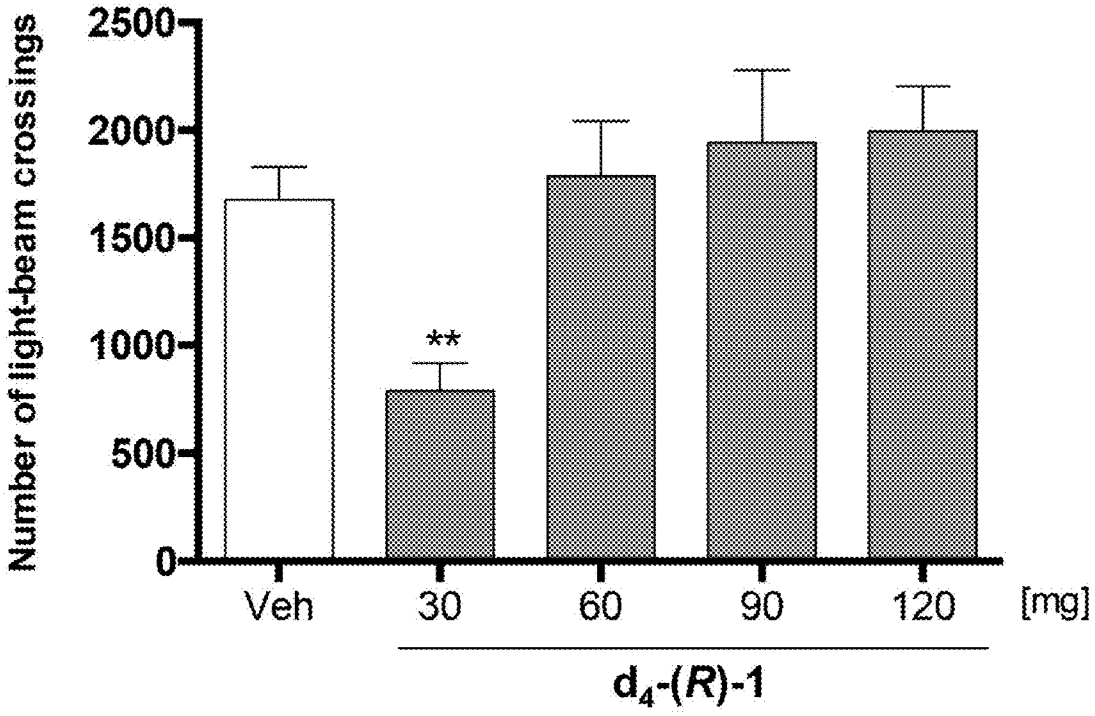

FIG. 18 shows the effect of compound $d_4$-(R)-1 on spontaneous locomotor activity of animals. The results show the number of infrared light beams interrupts during the 30 minutes of measurement. The values represent means ±SEM for a group of 8-10 animals. Statistically significant difference in comparison to control group (one-way repeated-measures analysis of variance (ANOVA), followed by Dunnett's post hoc test): ** p<0.01. Veh-1% aqueous solution of Tween 80.

Figure 19A:
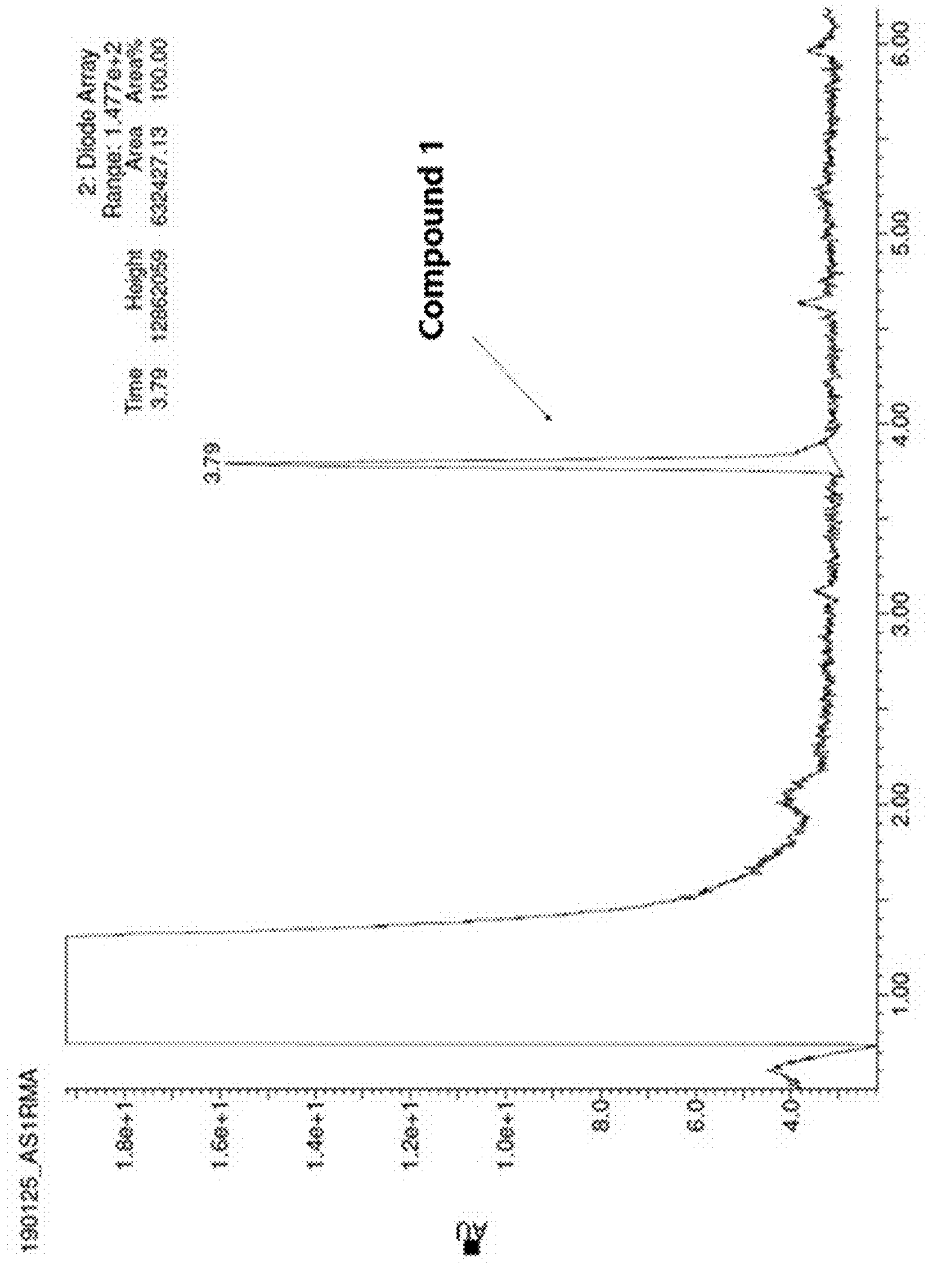
Figure 19B:
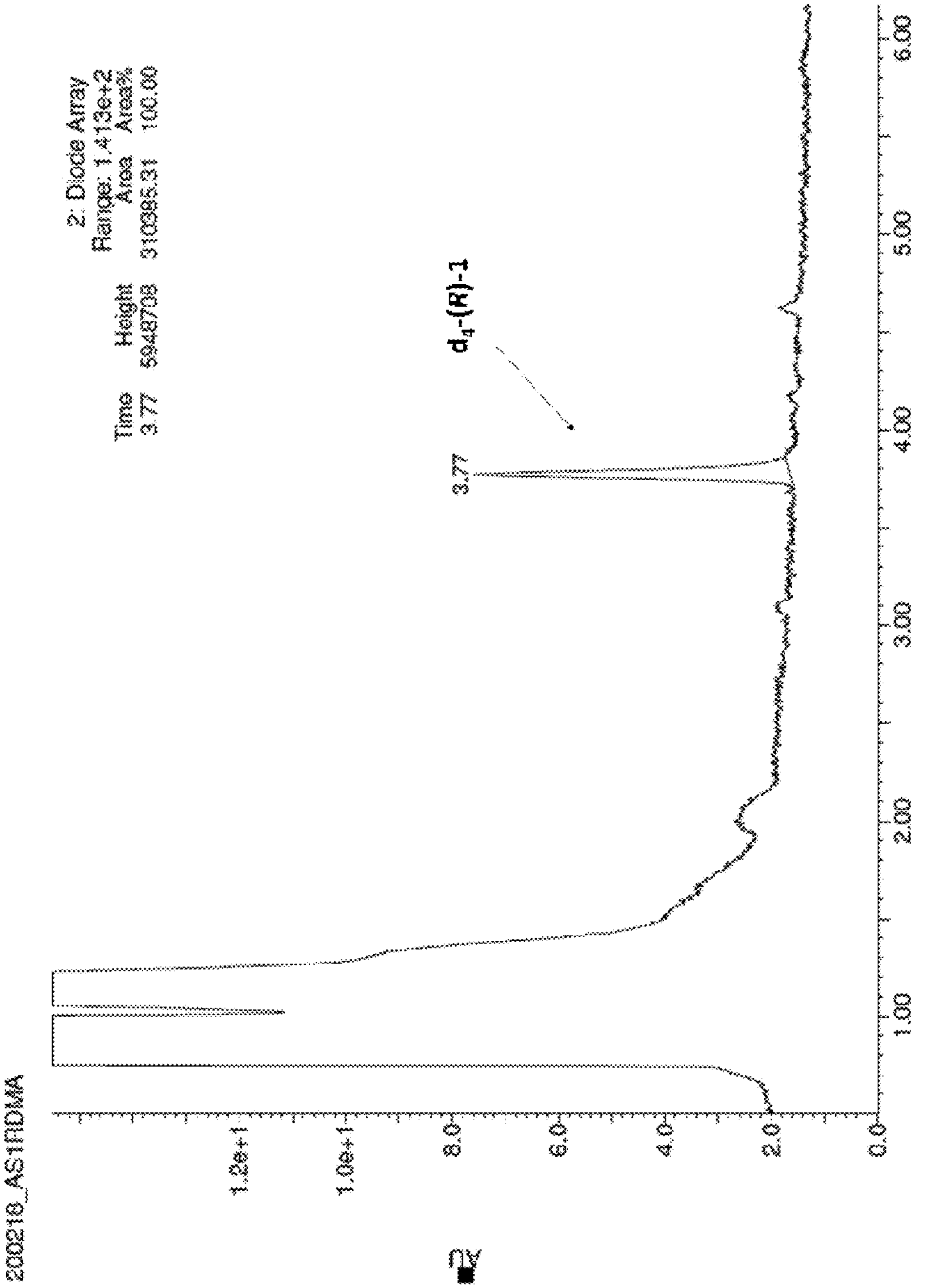

FIG. 19 shows the UPLC spectra after 120 min incubation of the parent compound 1 (A) and the deuterated analogue $d_4$-(R)-1 (B) with MLMs.

DETAILED DESCRIPTION OF THE INVENTION

Figure 1:
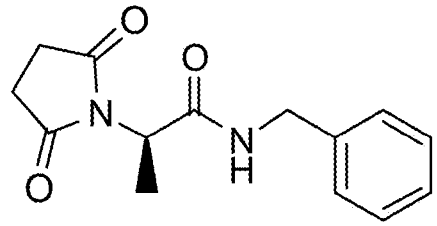
FIG. 1 shows the structures of prior art compounds 1 and 2 (patent applications P.429656, PCT/PL2020/050028 and patent Pat.240297).
Figure 1:
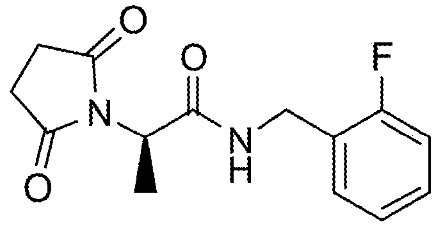
Figure 2:
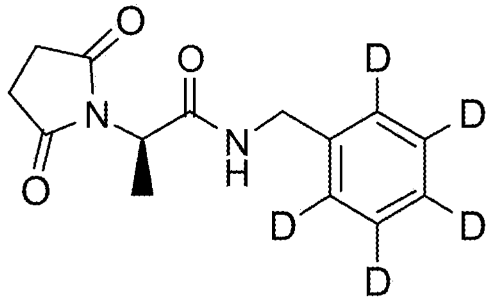
FIG. 2 shows the structures of compounds $d_5$-(R)-3 and $d_3$-(R)-8, which are not an embodiment of the invention and are comparative examples that do not show the technical effect obtained according to the invention.
Figure 2:
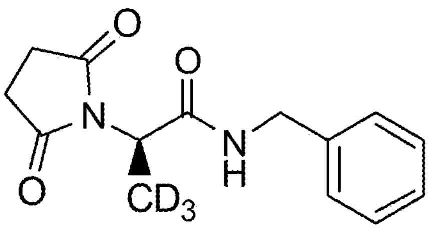

The present invention discloses analogues of the lead compounds 1 and 2 (FIG. 1) which are characterized by much longer biological half-life ($t_{0.5}$)—more than 80 minutes in plasma and brain, better brain penetration (AUC) and similar or more potent anticonvulsant activity in preclinical studies in mice. The disclosed compounds were designed using the hydrogen/deuterium bioisosteric replacement, and three or two sites, respectively, of deuterium incorporation into parent molecules 1 and 2 were proposed in the performed chemical studies. The incorporation of deuterium included the following fragments of the structure according to formula (I); (i) pyrrolidine-2,5-dione ring (replacement in position A); (ii) methylene moiety (replacement in position Y) (iii) benzylamine aromatic ring (replacement in positions B and X). In the performed chemical studies, a deuterated analogue of compound 1 was also synthesized, in the structure of which three deuterium atoms were incorporated in place of hydrogens atoms of the side methyl group (see compound $d_3$-(R)-8 in FIG. 2).

The compound of formula (I) has a chiral center, the scope of the invention includes in particular enantiomers with the R-configuration, which can be recognized as bioisosteres of compounds 1 and 2 which were disclosed in patent applications P.429656, PCT/PL2020/050028, and patent Pat.240297. These compounds can be obtained by using the appropriate isomeric forms of the starting material (amino acid derivatives) or they can be separated after preparation of the final compound according to known separation methods.

Chemical Studies:

The compounds of formula (I) according to the invention can be obtained according to four-step procedure using commercially available reagents as starting substances, i.e. a tert-butoxycarbonyl (Boc) derivative of alanine with the desired absolute configuration (R, S, or R,S), benzylamine (or its deuterated derivative—$d_2$-benzylamine, $d_5$-benzylamine or $d_7$-benzylamine) or 2-fluorobenzylamine (or its deuterated derivative—$d_2$-2-fluorobenzylamine) and succinic anhydride (or its deuterated analogue—$d_4$-succinic anhydride). The synthetic procedure and exemplary reaction conditions are illustrated in Scheme 1. In the first step, as a result of the condensation reaction of benzylamine or 2-fluorobenzylamine (or their respective deuterated derivatives) with alanine with the appropriate absolute configuration (R, S, or R,S) protected with tert-butoxycarbonyl group, an intermediate of formula (IV) is obtained, which is then deprotected to form a compound of formula (III). In the next step, the compound of formula (III) is used in a condensation reaction with the appropriate succinic anhydride (or $d_4$-succinic anhydride) to give an amido-acid compound of formula (II), which is then cyclized to form compounds of the general formula (I).

Intermediates and final compounds were obtained in good yield (>82%). Pseudo-molecular ion masses of intermediates and final products were determined by LC/MS method. The structures of the final compounds were confirmed by the 1H NMR and $^{13}$C NMR spectra analysis. The purity of the final compounds was determined by UPLC and was >99% for the final products. The enantiomeric purity was confirmed by chiral HPLC and was >99% ee.

Pharmacokinetic Studies:

As can be seen from the pharmacokinetic data in Tables 1-4, deuterium-free parent compounds 1 and 2 showed non-linear pharmacokinetics over the dose range studied, as evidenced by a disproportionate increase in area under the curve (a 2-fold increase in dose resulted in approx. a 2- and 1.4-fold increase in $AUC_{inf}$ in the serum and brain of animals, respectively, for compound 1, and a 4.1- and 2.4-fold increase in $AUC_{inf}$, respectively, for compound 2). In the case of the deuterated derivative $d_4$-(R)-1 according to the invention, a disproportionate 2.8-fold increase in the $AUC_{inf}$ ratio was observed with increasing the dose, but only in serum, which may indicate saturation of the elimination processes of this compound. Other derivatives, which are preferred embodiments of the invention, containing a different number of deuterium atoms in the structure, were characterized by non-linear pharmacokinetics in the tested dose range, and a doubling of the dose led to 1.7-($d_4$-(R)-4), 2.3-($d_6$-(R)-5) and 1.8-fold ($d_6$-(R)-7) increases in $AUC_{inf}$ in serum and 2.5-($d_6$-(R)-5) and 5.2-fold ($d_{11}$-(R)-6) increase in $AUC_{inf}$ in brain of tested animals. In contrast to the above data, the compound $d_9$-(R)-2 according to the invention exhibited linear pharmacokinetic processes (the area ratio was 1.9 after doubling the dose in both murine serum and brain). Similar linearity was observed for compound $d_{11}$-(R)-6 in plasma (the area ratio was 2.0 after doubling the dose). Surprisingly, in the case of analogues containing a fluorine atom in the structure, i.e. $d_4$-(R)-4 and $d_6$-(R)-7, doubling the dose resulted in a slight increase (1.1-fold) or a decrease in the $AUC_{inf}$ values in brains of animals tested.

Interestingly, $d_5$-(R)-3 derivative, containing 5 deuterium atoms only in the aromatic ring, and compound $d_3$-(R)-8, with the —$CD_3$ group in place of the —$CH_3$ group of the parent compound 1, were characterized by a similar concentration-time profile in serum and brain of the tested animals and similar values of pharmacokinetic parameters compared to the parent substance 1 (Table 2 and 4). For these derivatives, studies were performed only at a dose of 40 mg/kg. Compounds $d_5$-(R)-3 and $d_3$-(R)-8 can therefore be considered as negative examples where the incorporation of deuterium atoms did not result in an improvement of the pharmacokinetic profile of compound 1. All derivatives being preferred embodiments of the invention, i.e. $d_4$-(R)-1, $d_9$-(R)-2, $d_4$-(R)-4, $d_6$-(R)-5, $d_{11}$-(R)-6, and $d_6$-(R)-7 were characterized by much slower elimination, both from the serum and brain of the tested animals, as evidenced by the significantly longer biological half-life ($t_{0.5}$) of these compounds, exceeding 80 minutes, regardless of the dose used (20 or 40 mg/kg). For compounds $d_4$-(R)-1, $d_9$-(R)-2, $d_6$-(R)-5, and $d_{11}$-(R)-6, this was at least a 1.5-fold increase in $t_{0.5}$ in plasma and brain versus 1 and counterexamples—$d_5$-(R)-3 and $d_3$-(R)-8. A distinctly more pronounced extension of $t_{0.5}$ was observed for the deuterated analogues of the starting compound 2, i.e. $d_4$-(R)-4, $d_6$-(R)-7, at least 2.6-fold in plasma and at least 2.5-fold in the brain. Interestingly and unobviously, in the preferred embodiment, the incorporation of deuterium into molecule 1 increased the $AUC_{inf}$ parameter in the brain, but did not significantly change the $C_{max}$ values of the compounds tested. A similar relationship was not observed for counterexamples $d_5$-(R)-3 and $d_3$-(R)-8. Deuterated derivatives being the object of a particularly preferred embodiment of the present invention, i.e. $d_4$-(R)-1, $d_9$-(R)-2, $d_4$-(R)-4, $d_6$-(R)-5, $d_{11}$-(R)-6, and $d_6$-(R)-7, are also characterized by significantly longer mean residence time (MRT), i.e. in serum (>133 minutes) and brain (>148 minutes), compared to parent molecules 1 and 2 and counterexamples $d_5$-(R)-3 and $d_3$-(R)-8.

A similar beneficial isotope effect of deuterium incorporation into the molecule was observed for compound $d_6$-(R)-7, which was administered intragastrically (p.o.) to mice at a dose of 40 mg/kg. Comparison of profiles and pharmacokinetic parameters obtained for $d_6$-(R)-7 vs. parent compound 2 (see Table 5, FIGS. 11 and 12) indicates significantly better availability ($AUC_{inf}$), slightly higher plasma and brain concentrations, and a longer mean residence time of the deuterated compound.

Figure 3:
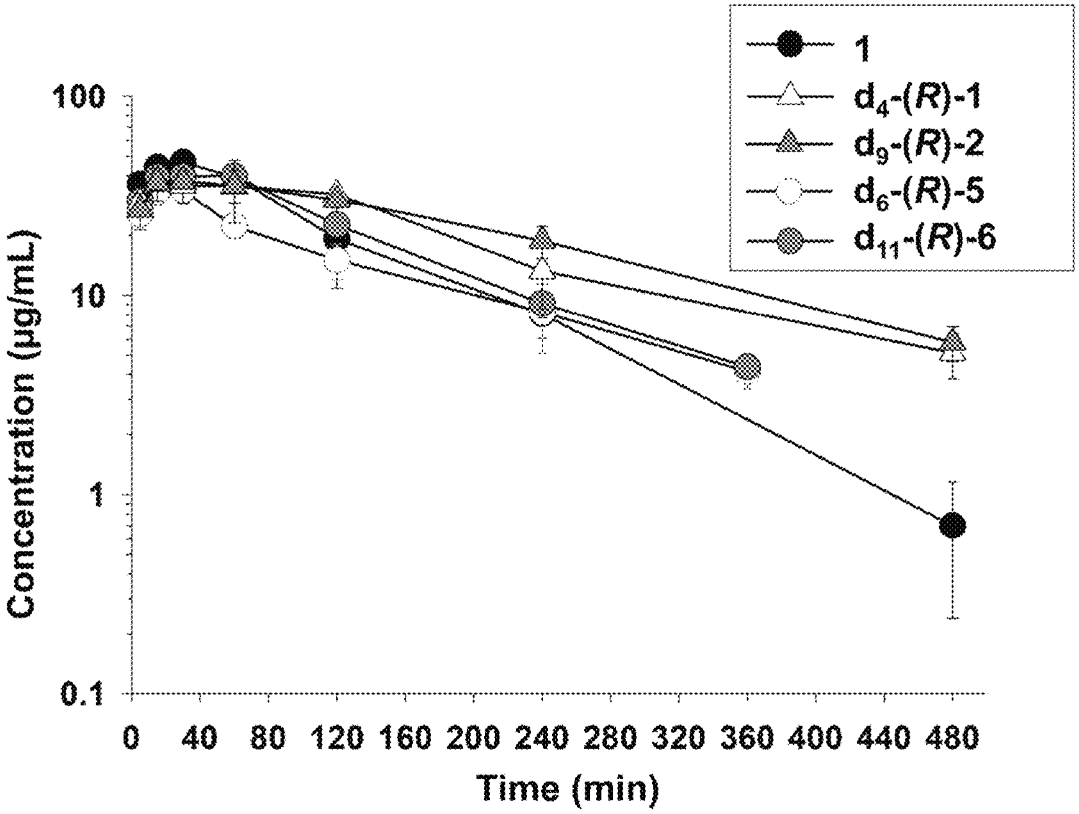
FIG. 3 shows a concentration of parent compound 1 and deuterated derivatives $d_4$-(R)-1, $d_9$-(R)-2, $d_6$-(R)-5, and $d_{11}$-(R)-6 in murine serum as a function of time following i.p. administration at a dose of 20 mg/kg (n=3-4).
Figure 4:
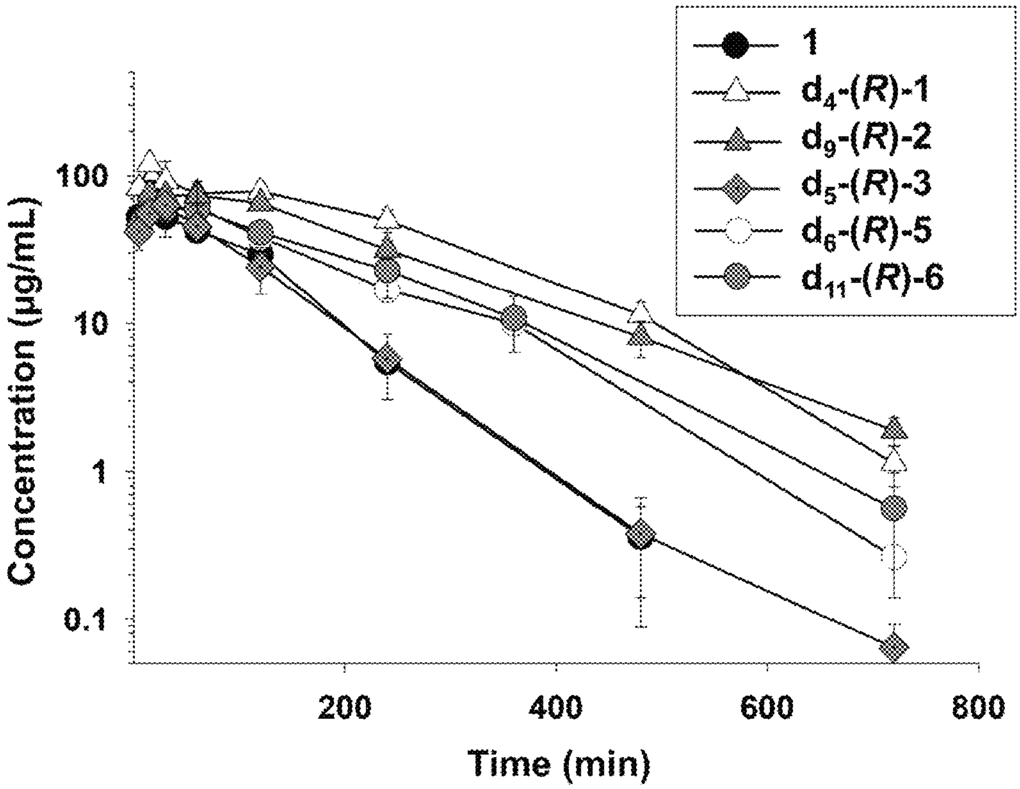
FIG. 4 shows a concentration of parent compound 1 and deuterated derivatives $d_4$-(R)-1, $d_9$-(R)-2, $d_5$-(R)-3, $d_6$-(R)-5, and $d_{11}$-(R)-6 in murine serum as a function of time following i.p. administration at a dose of 40 mg/kg (n=3-4). Compound $d_3$-(R)-8 having an identical profile to 1 and $d_5$-(R)-3 is not shown in the figure.
Figure 5:
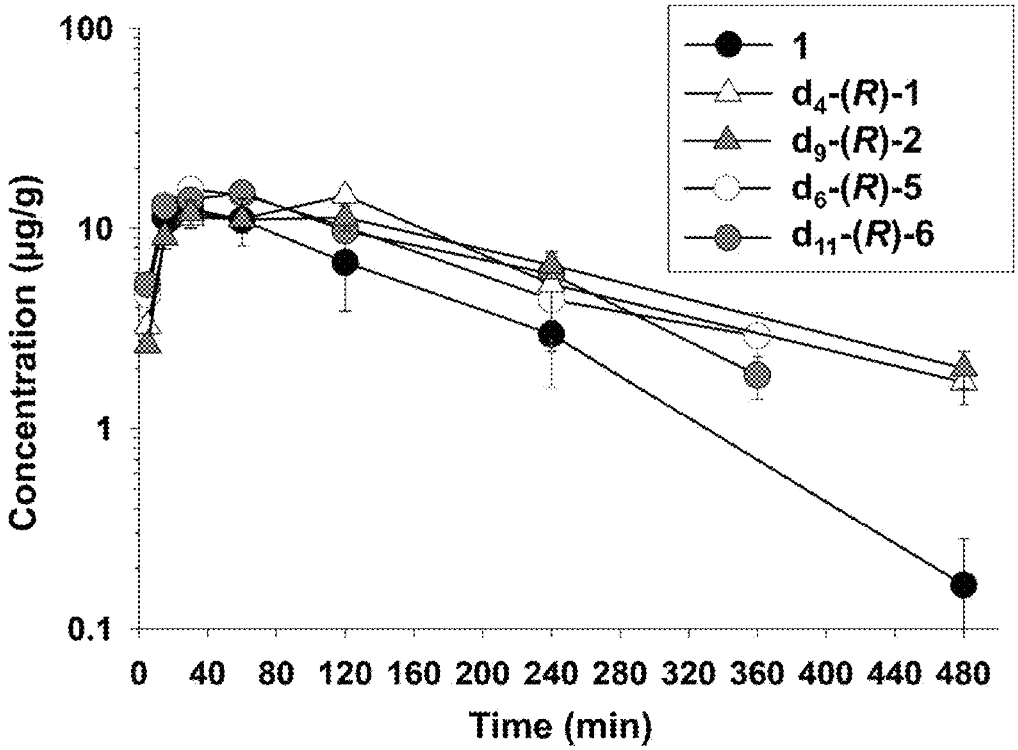
FIG. 5 shows a concentration of parent compound 1 and deuterated derivatives $d_4$-(R)-1, $d_9$-(R)-2, $d_6$-(R)-5, and $d_{11}$-(R)-6 in murine brain as a function of time following i.p. administration at a dose of 20 mg/kg (n=3-4).
Figure 6:
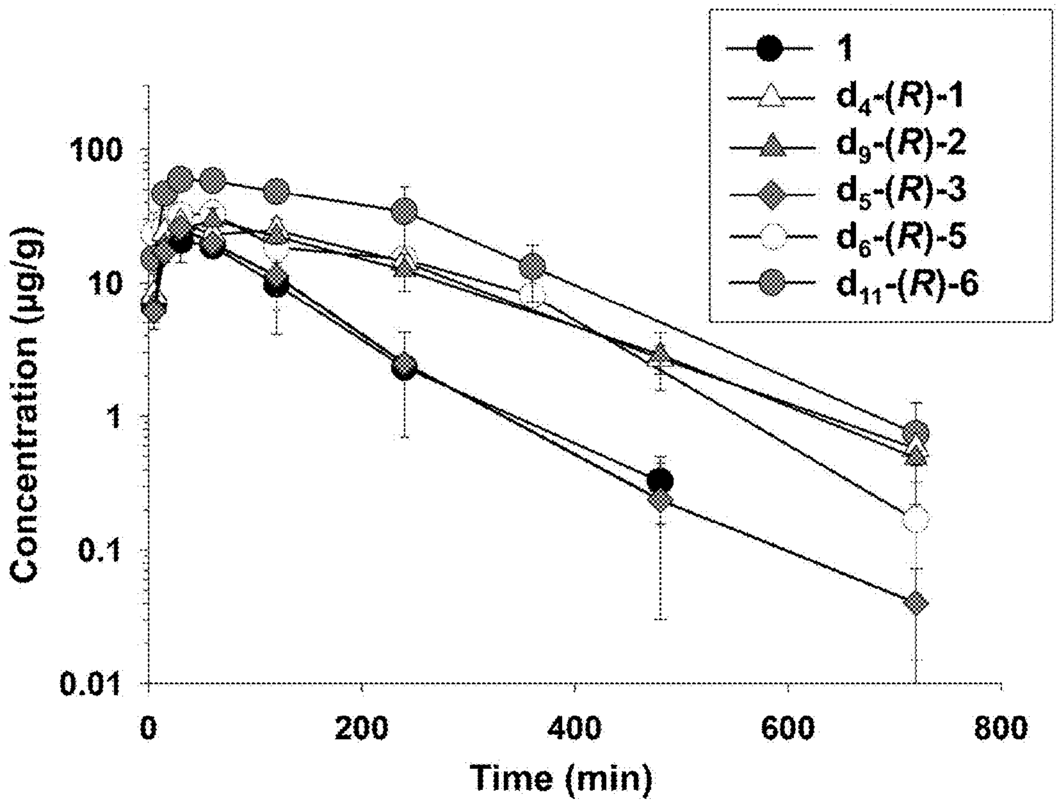
FIG. 6 shows a concentration of parent compound 1 and deuterated derivatives $d_4$-(R)-1, $d_9$-(R)-2, $d_5$-(R)-3, $d_6$-(R)-5, and $d_{11}$-(R)-6 in murine brain as a function of time following i.p. administration at a dose of 40 mg/kg (n=3-4). Compound $d_3$-(R)-8 having an identical profile to 1 and $d_5$-(R)-3 is not shown in the figure.
Figure 7:
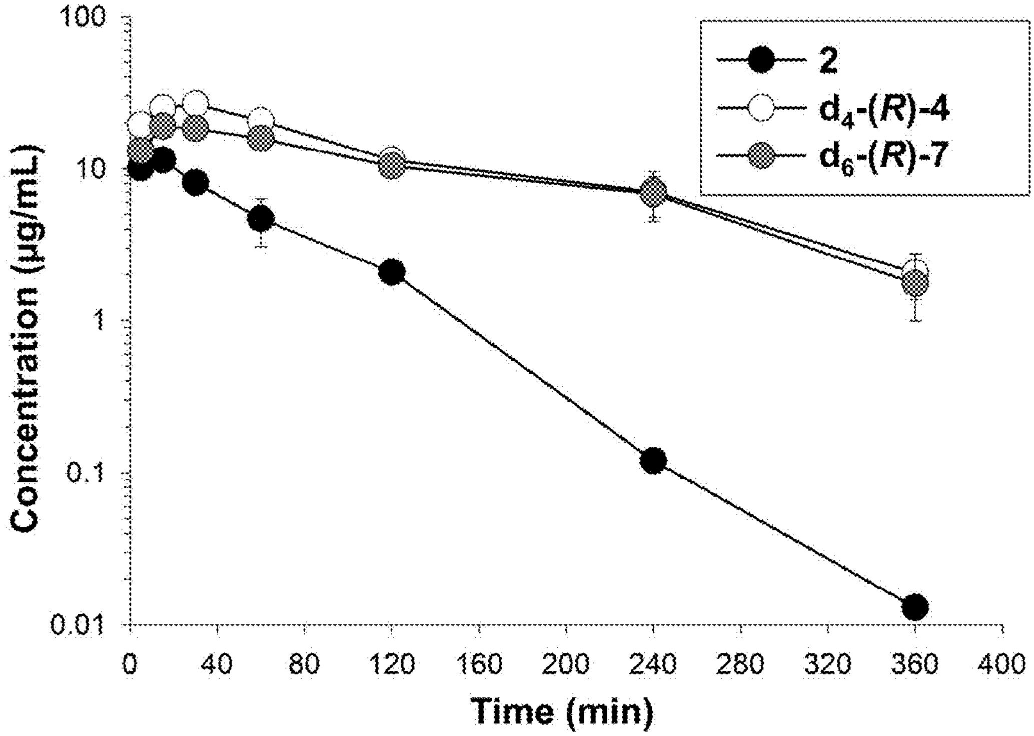
FIG. 7 shows a concentration of parent compound 2 and deuterated derivatives $d_4$-(R)-4 and $d_6$-(R)-7 in murine serum as a function of time following i.p. administration at a dose of 20 mg/kg (n=4).
Figure 8:
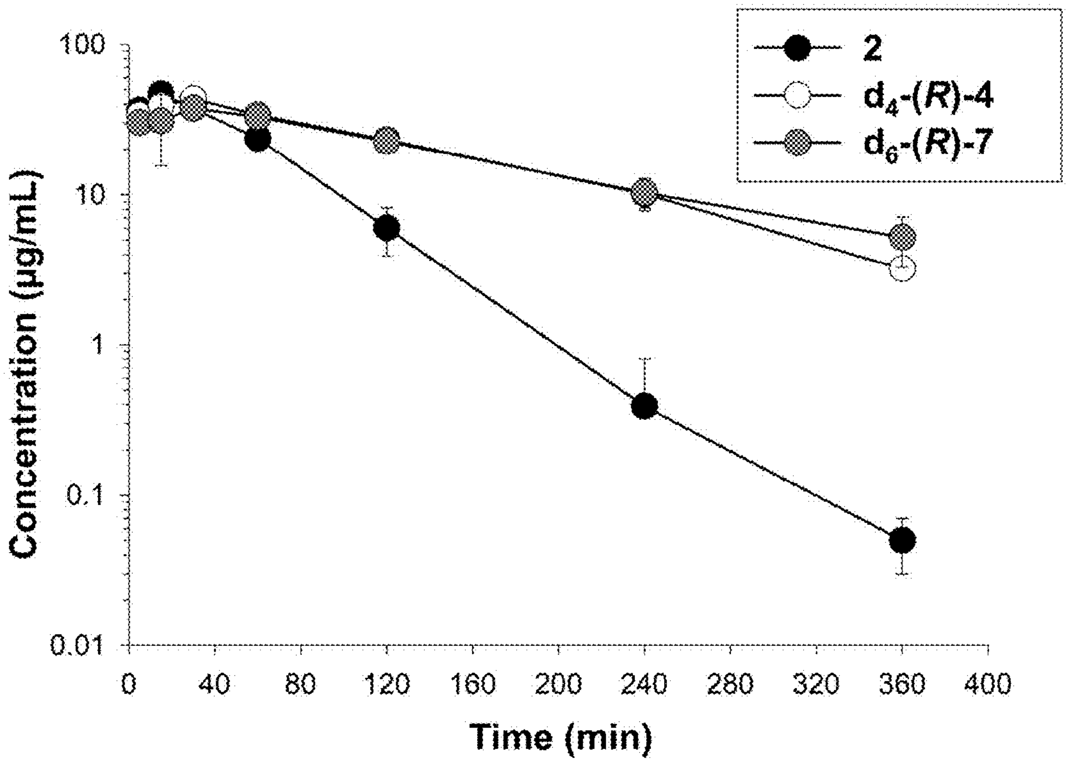
FIG. 8 shows a concentration of parent compound 2 and deuterated derivatives $d_4$-(R)-4 and $d_6$-(R)-7 in murine serum as a function of time following i.p. administration at a dose of 40 mg/kg (n=4).
Figure 9:
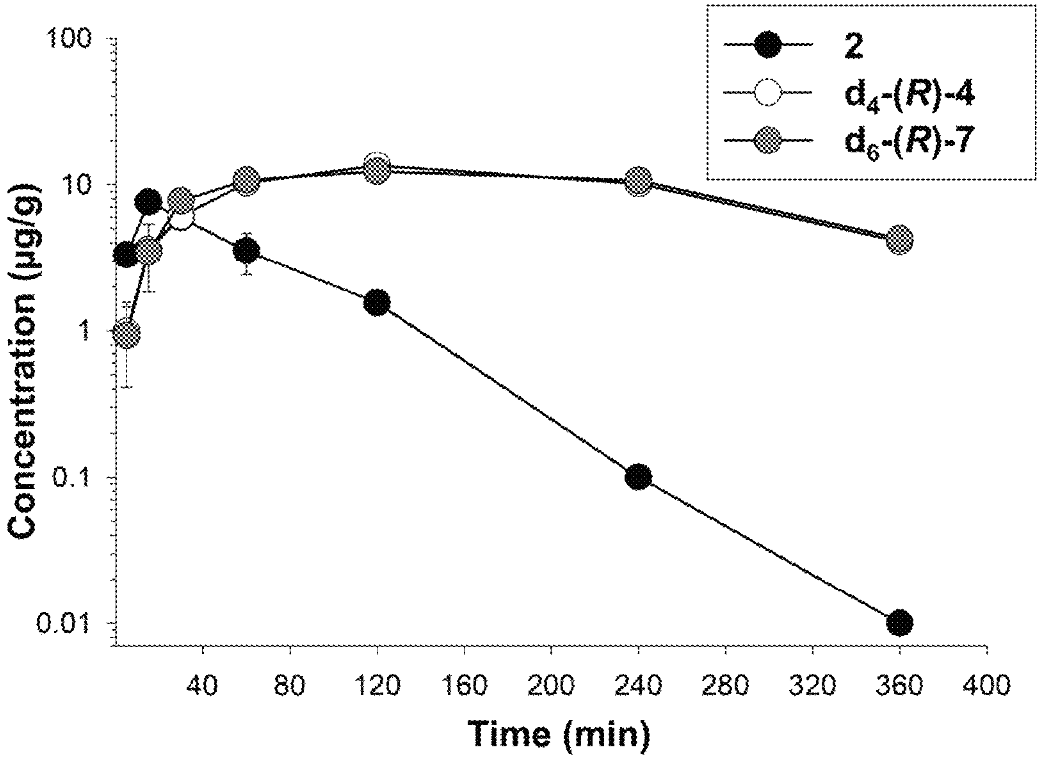
FIG. 9 shows a concentration of parent compound 2 and deuterated derivatives $d_4$-(R)-4 and $d_6$-(R)-7 in murine brain as a function of time following i.p. administration at a dose of 20 mg/kg (n=4).
Figure 10:
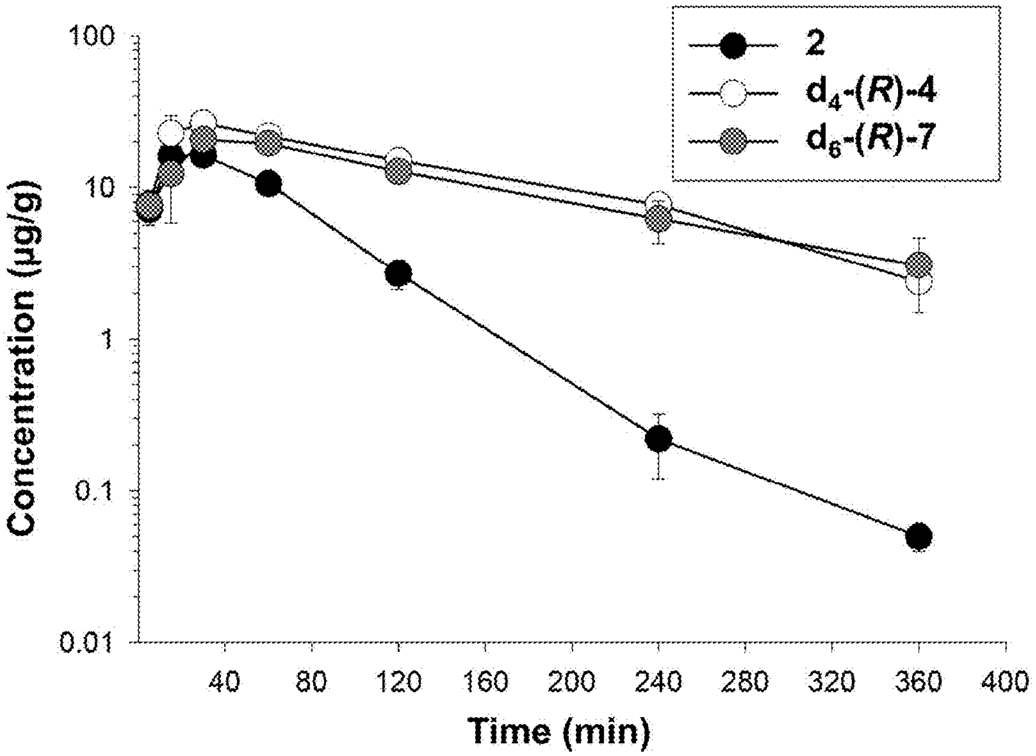
FIG. 10 shows a concentration of parent compound 2 and deuterated derivatives $d_4$-(R)-4 and $d_6$-(R)-7 in murine brain as a function of time following i.p. administration at a dose of 40 mg/kg (n=4).
Figure 11:
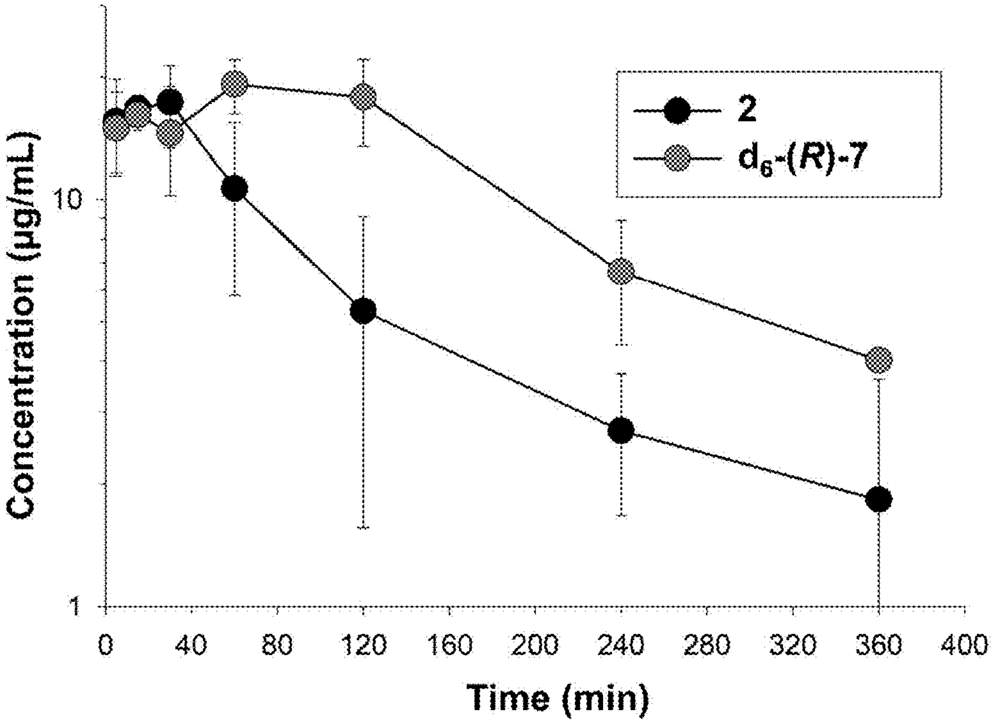
FIG. 11 shows a concentration of parent compound 2 and deuterated derivative $d_6$-(R)-7 in murine serum as a function of time following intragastric (p.o.) administration at a dose of 40 mg/kg (n=4).
Figure 12:
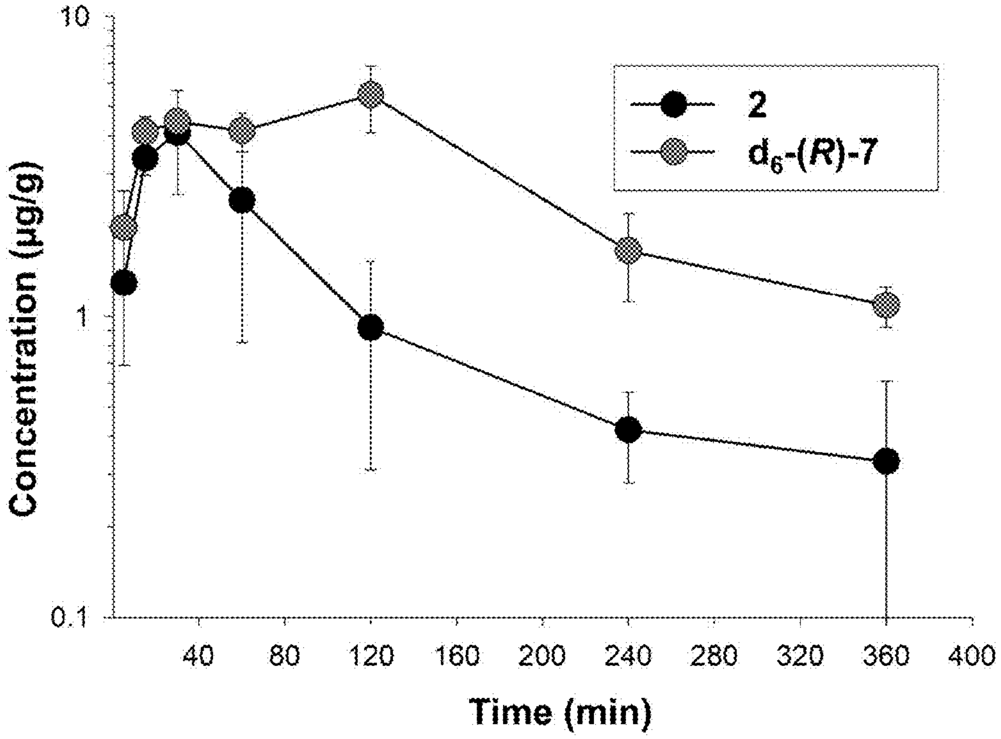
FIG. 12 shows a concentration of parent compound 2 and deuterated derivative $d_6$-(R)-7 in murine brain as a function of time following intragastric (p.o.) administration at a dose of 40 mg/kg (n=4).

FIG. 3 shows the concentration-time profiles of tested compounds 1, $d_4$-(R)-1, $d_9$-(R)-2, $d_6$-(R)-5 and $d_{11}$-(R)-6 in murine serum following administration at a dose of 20 mg/kg (i.p.), FIG. 4 shows the concentration-time profiles of the tested compounds, $d_4$-(R)-1, $d_9$-(R)-2, $d_5$-(R)-3, $d_6$-(R)-5 and $d_{11}$-(R)-6 in murine serum following administration at dose of 40 mg/kg (i.p.), FIG. 5 shows the concentration-time profiles of the tested compounds 1, $d_4$-(R)-1, $d_9$-(R)-2, $d_6$-(R)-5 and $d_{11}$-(R)-6 in murine brain following administration at a dose of 20 mg/kg (i.p.), FIG. 6 shows the concentration-time profiles of the tested compounds 1, $d_4$-(R)-1, $d_9$-(R)-2, $d_5$-(R)-3, $d_6$-(R)-5 and $d_{11}$-(R)-6 in murine brain following administration at a dose of 40 mg/kg (i.p.), FIG. 7 shows the concentration-time profiles of the tested compounds 2, $d_4$-(R)-4 and $d_6$-(R)-7 in murine serum following administration at a dose of 20 mg/kg (i.p.), FIG. 8 shows the concentration-time profiles of the tested of compounds 2, $d_4$-(R)-4 and $d_6$-(R)-7 in murine serum following administration at a dose of 40 mg/kg (i.p.), FIG. 9 shows the concentration-time profiles of the tested compounds 2, $d_4$-(R)-4 and $d_6$-(R)-7 in murine brain following administration at a dose of 20 mg/kg (i.p.), FIG. 10 shows the concentration-time profiles of tested compounds 2, $d_4$-(R)-4 and $d_6$-(R)-7 in murine brain following administration at a dose of 40 mg/kg (i.p.), FIG. 11 shows concentration-time profiles of tested compounds 2 and $d_6$-(R)-7 in murine plasma following administration at a dose of 40 mg/kg (p.o.), FIG. 12 shows the concentration-time profiles of tested compounds 2 and $d_6$-(R)-7 in murine brain following administration of a dose of 40 mg/kg (p.o.).

It is worth noting that a similar and clearly beneficial isotopic effect of incorporating four deuterium atoms into the pyrrolidine-2,5-dione ring was not observed in the case of compound $d_4$-(R)-KA-104, which, from a chemical point of view, is a deuterated analogue of the compound (R)-6, which was disclosed in patent applications P.428485 and PCT/PL2020/050001. It should be noted that the deuterated imide fragment in $d_4$-(R)-KA-104 is analogous to that observed with the compounds disclosed in this application, which are examples of preferred embodiments of the invention. Pharmacokinetic studies conducted for both of the above-mentioned substances, i.e. (R)-6 and $d_4$-(R)-KA-104, showed that $d_4$-(R)-KA-104 administered intraperitoneally at a dose of 40 mg/kg to mice has only a slightly longer biological half-life ($t_{0.5}$) and mean residence time (MRT), as well as slightly higher bioavailability ($AUC_{inf}$) compared to the parent compound—(R)-6, containing four hydrogen atoms in the succinimide ring. The chemical structure of the parent molecule, i.e. (R)-6, the deuterated analogue $d_4$-(R)-KA-104, and pharmacokinetic studies data are presented in Table 6.

TABLE 1

Pharmacokinetic parameters of the parent compounds 1 and 2 and their deuterated analogues following i.p. administration of a dose of 20 mg/kg, in murine serum, calculated using the non-compartmental analysis.

| | Parent compounds | | Deuterium-containing compounds | | | | | | | |
|---|---|---|---|---|---|---|---|---|---|---|
| Parameter | 1 | 2 | $d_4$-(R)-1 | $d_9$-(R)-2 | $d_5$-(R)-3* | $d_4$-(R)-4 | $d_6$-(R)-5 | $d_{11}$-(R)-6 | $d_6$-(R)-7 | $d_3$-(R)-8* |
| $t_{max}$ (min)[a] | 30 | 15 | 15 | 30 | NT | 30 | 30 | 60 | 15 | NT |
| $C_{max}$ (μg/mL)[b] | 46.60 | 11.36 | 36.60 | 37.46 | NT | 26.57 | 33.83 | 39.80 | 18.97 | NT |
| $\lambda_z$ ($min^{-1}$)[c] | 0.015 | 0.020 | 0.009 | 0.006 | NT | 0.007 | 0.006 | 0.007 | 0.007 | NT |
| $t_{0.5\lambda z}$ (min)[d] | 47.31 | 34.22 | 80.23 | 113.61 | NT | 96.00 | 125.78 | 94.77 | 99.74 | NT |
| $V_z$/F (L/kg)[e] | 0.20 | 1.21 | 0.24 | 0.30 | NT | 0.65 | 0.63 | 0.37 | 0.80 | NT |
| CL/F (L/min/kg)[f] | 0.003 | 0.025 | 0.002 | 0.002 | NT | 0.005 | 0.003 | 0.003 | 0.006 | NT |
| $AUC_{0-t}$ (μg · min/mL)[g] | 7000.20 | 811.93 | 9619.05 | 10733.91 | NT | 3964.95 | 4959.15 | 6792.25 | 3312.13 | NT |
| $AUC_{inf}$ (μg · min/mL)[h] | 7000.89 | 812.54 | 9641.41 | 10915.33 | NT | 4285.43 | 5715.14 | 7355.09 | 3615.74 | NT |
| MRT (min)[i] | 112.18 | 57.90 | 173.61 | 200.02 | NT | 141.73 | 173.08 | 139.15 | 154.28 | NT |

Pharmacokinetic parameters:

[a]$t_{max}$—time to reach the maximum concentration ($C_{max}$);

[b]$C_{max}$—maximum concentration;

[c]$\lambda_z$—terminal slope of the concentration-time curve;

[d]$t_{0.5\lambda z}$—terminal half-life;

[e]$V_z$/F—volume of distribution;

[f]CL/F— clearance;

[g]$AUC_{0-t}$—area under the concentration-time curve plotted to the last measured concentration;

[h]$AUC_{inf}$—area under the concentration-time curve plotted to infinity; and

MRT—mean residence time of the compound in the body.

*Compound not tested (NT) at a dose of 20 mg/kg. The substance was tested at a dose of –40 mg/kg (Table 2 and 4). The substances were dissolved in a mixture of DMSO, PEG400 and water for injection (1:4:5, v/v/v).

TABLE 2

Pharmacokinetic parameters of the parent compounds 1 and 2 and their deuterated analogues following i.p. administration of a dose of 40 mg/kg, in murine serum, calculated using the non-compartmental analysis.

| | Parent compounds | | Deuterium-containing compounds | | | | | | | |
|---|---|---|---|---|---|---|---|---|---|---|
| Parameter | 1 | 2 | $d_4$-(R)-1 | $d_9$-(R)-2 | $d_5$-(R)-3 | $d_4$-(R)-4 | $d_6$-(R)-5 | $d_{11}$-(R)-6 | $d_6$-(R)-7 | $d_3$-(R)-8 |
| $t_{max}$ (min)[a] | 15 | 15 | 15 | 15 | 30 | 30 | 60 | 30 | 30 | 15 |
| $C_{max}$ (μg/mL)[b] | 76.75 | 46.93 | 120.50 | 75.05 | 62.76 | 43.43 | 60.97 | 59.73 | 37.63 | 76.14 |
| $\lambda_z$ ($min^{-1}$)[c] | 0.012 | 0.021 | 0.008 | 0.006 | 0.01 | 0.008 | 0.007 | 0.008 | 0.006 | 0.012 |
| $t_{0.5\lambda z}$ (min)[d] | 55.62 | 33.50 | 88.04 | 117.99 | 69.50 | 88.73 | 97.52 | 88.19 | 112.02 | 56.82 |
| $V_z$/F (L/kg)[e] | 0.39 | 0.57 | 0.19 | 0.34 | 0.52 | 0.72 | 0.43 | 0.35 | 0.88 | 0.38 |
| CL/F (L/min/kg)[f] | 0.005 | 0.01 | 0.002 | 0.002 | 0.005 | 0.01 | 0.00 | 0.00 | 0.01 | 0.005 |
| $AUC_{0-t}$ (μg · min/mL)[g] | 8172.95 | 3361.93 | 26473.86 | 19973.31 | 7780.40 | 6737.80 | 13178.86 | 14442.43 | 6524.33 | 8142.85 |
| $AUC_{inf}$ (μg · min/mL)[h] | 8174.16 | 3363.98 | 26640.04 | 20299.55 | 7785.46 | 7183.46 | 13179.30 | 14442.69 | 7347.14 | 8144.18 |
| MRT (min)[i] | 93.47 | 52.83 | 181.79 | 183.07 | 95.18 | 133.32 | 158.36 | 171.57 | 163.84 | 94.14 |

Pharmacokinetic parameters - see Table 1. The substances were dissolved in a mixture of DMSO, PEG400 and water for injection (1:4:5, v/v/v).

TABLE 3

Pharmacokinetic parameters of the parent compounds 1 and 2 and their deuterated analogues following i.p. administration of a dose of 20 mg/kg, in murine brain, calculated using the non-compartmental analysis.

| | Parent compounds | | Deuterium-containing compounds | | | | | | | |
|---|---|---|---|---|---|---|---|---|---|---|
| Parameter | 1 | 2 | $d_4$-(R)-1 | $d_9$-(R)-2 | $d_5$-(R)-3* | $d_4$-(R)-4 | $d_6$-(R)-5 | $d_{11}$-(R)-6 | $d_6$-(R)-7 | $d_3$-(R)-8* |
| $t_{max}$ (min)[a] | 30 | 15 | 120 | 30 | NT | 120 | 30 | 60 | 120 | NT |
| $C_{max}$ (μg/mL)[b] | 12.55 | 7.58 | 14.61 | 11.89 | NT | 13.45 | 15.75 | 15.08 | 12.28 | NT |
| $\lambda_z$ ($min^{-1}$)[c] | 0.012 | 0.020 | 0.008 | 0.007 | NT | 0.005 | 0.006 | 0.007 | 0.004 | NT |
| $t_{0.5\lambda z}$ (min)[d] | 57.26 | 34.50 | 87.82 | 103.84 | NT | 140.03 | 124.93 | 103.67 | 157.83 | NT |
| $AUC_{0-t}$ (μg · min/mL)[g] | 2130.28 | 564.48 | 3626.38 | 3703.00 | NT | 3322.35 | 2829.45 | 2879.95 | 3346.33 | NT |

TABLE 3-continued

Pharmacokinetic parameters of the parent compounds 1 and 2 and their deuterated analogues following i.p. administration of a dose of 20 mg/kg, in murine brain, calculated using the non-compartmental analysis.

| | Parent compounds | | Deuterium-containing compounds | | | | | | | |
|---|---|---|---|---|---|---|---|---|---|---|
| Parameter | 1 | 2 | $d_4$-(R)-1 | $d_9$-(R)-2 | $d_5$-(R)-3* | $d_4$-(R)-4 | $d_6$-(R)-5 | $d_{11}$-(R)-6 | $d_6$-(R)-7 | $d_3$-(R)-8* |
| $AUC_{inf}$ (μg · min/mL)$^h$ | 2130.83 | 564.97 | 3626.44 | 3703.37 | NT | 4240.97 | 3305.98 | 3193.55 | 4454.18 | NT |
| MRT (min)$^i$ | 123.75 | 62.21 | 183.97 | 208.09 | NT | 253.32 | 184.25 | 165.04 | 273.39 | NT |

Pharmacokinetic parameters - see Table 1.

*Compound not tested (NT) at a dose of 20 mg/kg. The substance was tested at a dose of 40 mg/kg (Table 4). The substances were dissolved in a mixture of DMSO, PEG400 and water for injection (1:4:5, v/v/v).

TABLE 4

Pharmacokinetic parameters of the parent compounds 1 and 2 and their deuterated analogues following i.p. administration of a dose of 40 mg/kg, in murine brain, calculated using the non-compartmental analysis.

| | Parent compounds | | Deuterium-containing compounds | | | | | | | |
|---|---|---|---|---|---|---|---|---|---|---|
| Parameter | 1 | 2 | $d_4$-(R)-1 | $d_9$-(R)-2 | $d_5$-(R)-3 | $d_4$-(R)-4 | $d_6$-(R)-5 | $d_{11}$-(R)-6 | $d_6$-(R)-7 | $d_3$-(R)-8 |
| $t_{max}$ (min)$^a$ | 15 | 30 | 30 | 60 | 30 | 30 | 60 | 30 | 30 | 15 |
| $C_{max}$ (μg/mL)$^b$ | 21.87 | 16.23 | 27.93 | 29.36 | 25.72 | 26.57 | 33.08 | 59.50 | 20.78 | 22.00 |
| $\lambda_z$ ($min^{-1}$)$^c$ | 0.016 | 0.018 | 0.007 | 0.005 | 0.009 | 0.007 | 0.006 | 0.006 | 0.006 | 0.015 |
| $t_{0.5\lambda z}$ (min)$^d$ | 75.11 | 38.53 | 103.39 | 140.00 | 74.38 | 95.78 | 111.98 | 119.42 | 113.19 | 74.40 |
| $AUC_{0-t}$ (μg · min/mL)$^g$ | 3011.26 | 1368.32 | 7761.75 | 7367.63 | 3252.46 | 4335.42 | 8189.80 | 16670.98 | 3629.96 | 3054.20 |
| $AUC_{inf}$ (μg · min/mL)$^h$ | 3014.90 | 1370.46 | 7762.42 | 7368.22 | 3256.03 | 4703.70 | 8190.85 | 16674.91 | 4122.65 | 3056.85 |
| MRT (min)$^i$ | 105.34 | 58.60 | 192.77 | 189.95 | 103.55 | 148.65 | 185.06 | 189.41 | 172.05 | 105.14 |

Pharmacokinetic parameters - see Table 1. The substances were dissolved in a mixture of DMSO, PEG400 and water for injection (1:4:5, v/v/v).

TABLE 5

Pharmacokinetic parameters of the parent compound 2 and the deuterated analogue $d_6$-(R)-7 following p.o. administration of a dose of 40 mg/kg in mice, calculated using the non-compartmental analysis.

| Parameter | 2 | $d_6$-(R)-7 |
|---|---|---|
| | Plasma | |
| $t_{max}$ (min)$^a$ | 30 | 60 |
| $C_{max}$ (μg/mL)$^b$ | 17.37 | 19.20 |
| $\lambda_z$ ($min^{-1}$)$^c$ | 0.006 | 0.006 |
| $t_{0.5\lambda z}$ (min)$^d$ | 122.56 | 122.55 |
| $V_z$/F (L/kg)$^e$ | 2.91 | 1.45 |
| CL/F (L/min/kg)$^f$ | 0.02 | 0.01 |
| $AUC_{0-t}$ (μg · min/mL)$^g$ | 2108.53 | 4154.50 |
| $AUC_{inf}$ (μg · min/mL)$^h$ | 2393.00 | 4835.00 |
| MRT (min)$^i$ | 155.31 | 186.54 |
| | Brain | |
| $t_{max}$ (min)$^a$ | 30 | 120 |
| $C_{max}$ (μg/g)$^b$ | 4.10 | 5.47 |
| $\lambda_z$ ($min^{-1}$)$^c$ | 0.01 | 0.005 |
| $t_{0.5\lambda z}$ (min)$^d$ | 109.50 | 130.12 |
| $AUC_{0-t}$ (μg · min/mL)$^g$ | 407.05 | 1110.93 |
| $AUC_{inf}$ (μg · min/mL)$^h$ | 448.57 | 1308.37 |
| MRT (min)$^i$ | 135.32 | 193.88 |

Pharmacokinetic parameters - see Table 1. The substances were dissolved in a mixture of DMSO, PEG400 and water for injection (1:4:5, v/v/v).

TABLE 6

The structure of compounds (R)-6 and $d_4$-(R)-KA-104 and the pharmacokinetic parameters of the tested compounds following i.p. administration of a dose of 40 mg/kg, in murine serum, calculated using the non-compartmental analysis.

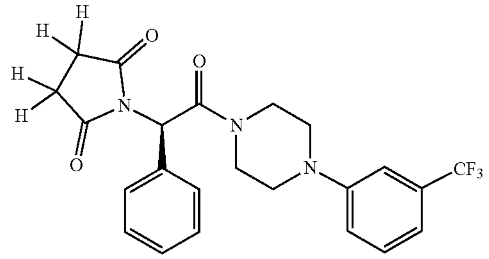 [SMILES: O=C([C@@H](c1ccccc1)N1C(=O)CCC1=O)N1CCN(c2cccc(C(F)(F)F)c2)CC1]

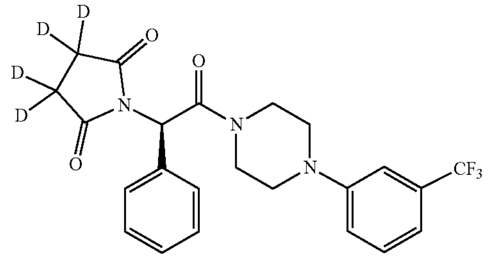 [SMILES: [2H]C1([2H])C(=O)N([C@@H](C(=O)N2CCN(c3cccc(C(F)(F)F)c3)CC2)c2ccccc2)C(=O)C1([2H])[2H]]

| Parameter | (R)-6* | $d_4$-(R)-KA-104 |
|---|---|---|
| $t_{max}$ (min)$^a$ | 15 | 5 |
| $C_{max}$ (μg/mL)$^b$ | 16.32 | 28.60 |
| $\lambda_z$ ($min^{-1}$)$^c$ | 0.014 | 0.011 |
| $t_{0.5\lambda}$ (min)$^d$ | 50.42 | 60.74 |
| $V_z$/F (L/kg)$^e$ | 2.82 | 2.48 |

TABLE 6-continued

The structure of compounds (R)-6 and $d_4$-(R)-KA-104 and the pharmacokinetic parameters of the tested compounds following i.p. administration of a dose of 40 mg/kg, in murine serum, calculated using the non-compartmental analysis.

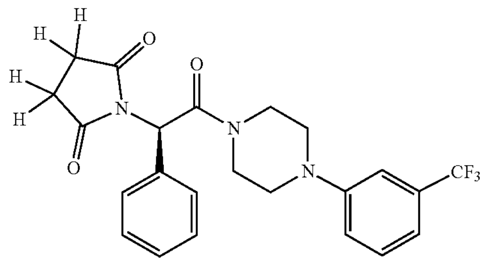

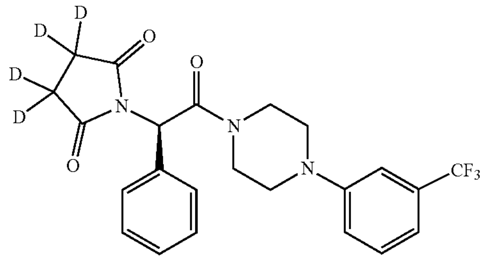

| Parameter | (R)-6* | $d_4$-(R)-KA-104 |
|---|---|---|
| CL/F (L/min/kg)[f] | 0.039 | 0.028 |
| $AUC_{0-t}$ (μg · min/mL)[g] | 1028.76 | 1411.11 |
| $AUC_{inf}$ (μg · min/mL)[h] | 1029.76 | 1415.52 |
| MRT (min)[i] | 58.35 | 68.37 |

*The structure of compound (R)-6 has been disclosed in patent applications P.428485 and PCT/PL2020/050001.
Pharmacokinetic parameters - see Table 1. The substances were dissolved in a mixture of DMSO, PEG400 and water for injection (1:4:5, v/v/v).

The Methodology section describes the synthetic procedure and physicochemical data for the newly obtained derivative $d_4$-(R)-KA-104, which has not been previously disclosed. This compound, which is a selectively deuterated analogue of compound (R)-6, disclosed in patent applications P.428485 and PCT/PL2020/050001, is also the object of the present invention.

Anticonvulsant Activity:

Another object of the invention is the application of compounds described by the formula (I), in particular $d_4$-(R)-1, $d_9$-(R)-2, $d_4$-(R)-4, $d_6$-(R)-5, $d_{11}$-(R)-6, and $d_6$-(R)-7, being a preferred embodiment of the invention, as an active substance in pharmaceutical formulations, especially for the treatment of epilepsy or neuropathic pain or migraine or depression or anxiety or neurodegenerative diseases (Alzheimer's disease, Parkinson's disease, amyotrophic lateral sclerosis, etc.). The deuterated compounds according to the invention, as well as their hydrogen bioisosteres disclosed in patent applications P.429656, PCT/PL2020/050028, and patent Pat.240297, show anticonvulsant activity in a wide range of animal models and can be used as active ingredients of various drug forms for the treatment of epilepsy. Based on biological data for individual stereoisomers of parent compounds 1 and 2 which are disclosed in patent applications P.429656, PCT/PL2020/050028, and patent Pat.240297, it can be expected that the S-enantiomers and racemic mixtures (R,S) of compounds containing deuterium disclosed in present application will have wide-spectrum, nevertheless weaker anticonvulsant activity compared to R-eutomers.

Compounds $d_4$-(R)-1, $d_9$-(R)-2, $d_4$-(R)-4, $d_6$-(R)-5, $d_{11}$-(R)-6, and $d_6$-(R)-7 being a particularly preferred embodiment of the invention exhibit broad spectrum anticonvulsant activity, namely they are effective in the maximal electroshock seizure test (MES), 6 Hz (32 mA and 44 mA) seizure test, and the subsutaneous pentylenetetrazole seizure test (scPTZ, this test discloses data for compounds $d_4$-(R)-1 i $d_9$-(R)-2) when administered intraperitoneally to mice (Table 6). Substances with such pharmacological profile may be potentially effective in broad spectrum of human seizures, namely tonic-clonic seizures with or without secondary generalization, myoclonic seizures, generalized absence seizures, focal onset seizures, and drug-resistant epilepsy. In time point of 0.5 h after intraperitoneal administration, all deuterium-containing derivatives were effective in MES, 6 Hz (32 mA), and 6 Hz (44 mA) tests/models. Compounds $d_4$-(R)-1 and $d_9$-(R)-2 were also effective in the scPTZ test, and the potency was comparable to the activity observed for the parent substance 1. Surprisingly, in a preferred embodiment of the invention, compared to the parent compounds 1 and 2, the deuterated derivatives are characterized by stronger activity in the MES test, which is invariably one of the most important animal models of seizures used to identify candidates for new antiepileptic drugs (Castel-Branco, M. M. et al. *Methods Find. Exp. Clin. Pharmacol.* 2009, 31, 101-106). In addition, the deuterated compounds $d_4$-(R)-1, $d_9$-(R)-2, $d_4$-(R)-4, $d_6$-(R)-5, $d_{11}$-(R)-6, and $d_6$-(R)-7, being a particularly preferred embodiment of the invention, are effective in all epileptic seizure assays/models at an additional time point of 2 h after i.p. administration, while parent molecules 1 (in particular) and 2 were less active or inactive in this time interval. This undoubtedly proves that the incorporation of deuterium, in particular to the pyrrolidine-2,5-dione ring (position A, formula I), but also to the methylene bridge (position Y, formula 1), has a positive effect on the pharmacokinetic profile and allows for a significant extension of the biological half-life ($t_{0.5}$), which results in the extension of the effective anticonvulsant protection of deuterated compounds vs. parent substances 1 and 2. PK/PD analysis of the obtained pharmacokinetic profiles in relation to data from seizure tests/models indicates that the most favorable PK/PD properties are offered in particular by compounds $d_4$-(R)-4 and $d_4$-(R)-7, which are deuterated derivatives of compound 2. Particularly noteworthy is the fact that all the disclosed compounds, in particular $d_4$-(R)-4 and $d_6$-(R)-7, have a strong protective effect in the 6 Hz (44 mA) test, which is considered as one of the most important animal models for identifying substances potentially effective in the treatment of drug-resistant epilepsy (Metcalf, C. et. al. *Epilepsia* 2017, 1073-1084; Barton, M. E. et al. *Epilepsy Res.* 2001, 47, 217-227). Furthermore, almost identical physicochemical properties of hydrogen and deuterium suggest that the bioisosteric replacement applied herein, as in the case of anticonvulsant activity, will at least maintain the antidepressant, anxiolytic, analgesic, neuroprotective, and neurotrophic activity of the parent molecule 1, which was disclosed in patent applications P.429656, PCT/PL2020/050028, and patent Pat.240297. Considering the above facts, it is also suggested that the disclosed deuterium-containing derivatives have the same mechanism of action as their chemical precursors 1 and 2, i.e. they are positive and selective allosteric modulators of the EAAT2 glutamate transporter (Abram, M. et. *J. Med. Chem.* 2022, 65, 11703-11725). It is worth noting that, according to literature data, compounds which increase EAAT2 activity directly or indirectly by increasing its expression on glial cells are promising candidates for the treatment of neurological (including neurodegenerative) and psychiatric diseases, i.e. amyotrophic lateral sclerosis, multiple sclerosis, Parkinson's disease, Alzheimer's disease, Huntington's disease, schizophrenia, neuropathic pain, anxiety, depression, ischemic stroke, epilepsy, etc. (Fontana, A. C. K. *J. Neurochem.* 2015, 134, 982-1007; Pajarillo, E. et al. *Neuropharmacology* 2019, 161, 107559; Rosenblum, L. T.; Trotti, D. *Adv. Neurobiol.* 2017, 16, 117-136; John, C. S. et al. *Neuropsychopharmacology* 2015, 40, 1700-1708; Zaitsev, A. V. et al. *CNS Drugs* 2020, 34, 1089-1103; Green, J. L. et al. *Biochem. Pharmacol.* 2021, 193, 114786; Temmermand, R. et al. *Pharmacol. Res.* 2022, 185, 106492).

Equally important, all compounds $d_4$-(R)-1, $d_9$-(R)-2, $d_4$-(R)-4, $d_6$-(R)-5, $d_{11}$-(R)-6, and $d_6$-(R)-7 showed significantly higher activity in given seizure tests/models than valproic acid (VPA, Table 6), which is a model antiepileptic drug with a wide range of therapeutic indications, including: generalized seizures (myoclonic seizures, tonic-clonic seizures, atonic seizures, absence seizure), focal onset seizures (simple or complex seizures, secondary generalized seizures), Lennox-Gastaut syndrome, treatment of manic episodes in bipolar disorder and migraine.

FIG. 13 shows the effect of selected compounds, i.e. $d_4$-(R)-1 and $d_9$-(R)-2, on the latency of the first episode of clonic seizures in the scPTZ test. Compounds $d_4$-(R)-1 and $d_9$-(R)-2 in a dose-dependent manner increased the latency time of the first onset of the clonic seizure compared to the control group. Statistically significant results were obtained for compound $d_4$-(R)-1 at doses of 40 and 60 mg/kg (extension of latency time: from 740±212.5 seconds to 1399±207.5 seconds, $p<0.05$ and 1789±11.2 seconds, $p<0.01$, respectively), and for compound $d_9$-(R)-2 at dose of 60 mg/kg (from 740±212.5 seconds to 1632±167.8 seconds, $p<0.05$). Parent compound 1 statistically significantly increased latency at doses of 40 and 60 mg/kg (from 740±212.5 seconds to 1568+150.9 seconds, $p<0.05$ and 1467±210.8 seconds, $p<0.05$, respectively). Unlike compounds $d_4$-(R)-1 and $d_9$-(R)-2, the observed effect for parent derivative 1 was not dose-dependent.

TABLE 6

$ED_{50}$ and $TD_{50}$ values of parent compounds 1 and 2 and their deuterated analogues.

| | Test | | | | |
|---|---|---|---|---|---|
| | $ED_{50}$ MES[a] | | $ED_{50}$ 6 Hz (32 mA)[b] | | $ED_{50}$ 6 Hz (44 mA)[c] |
| | Time | | | | |
| | 0.5 h | 2.0 h | 0.5 h | 2.0 h | 0.5 h |
| $d_4$-(R)-1 | 43.7 (38.3-50.0) | 50.1 (44.4-73.1) | 18.6 (11.5-30.2) | 46.4 (40.5-53.3) | 79.2 (62.9-99.8) |
| $d_9$-(R)-2 | 45.0 (29.2-69.5) | 57.7 (45.5-73.1) | 18.2 (12.4-26.5) | 68.0 (61.8-74.9) | 78.3 (53.1-115.5) |
| $d_5$-(R)-3* | NT | NT | NT | NT | NT |
| $d_4$-(R)-4 | 20.5 (16.8-25.0) | 25.3 (20.8-30.8) | 12.8 (10.5-16.0) | 19.8 (13.3-29.4) | 51.6 (31.3-85.2) |
| $d_6$-(R)-5 | 33.4 (29.5-37.7) | 28.7 (17.3-47.8) | 27.4 (21.7-34.5) | 33.0 (22.6-48.3) | 85.6 (57.0-128.4) |
| $d_{11}$-(R)-6 | 29.5 (24.48-35.7) | 33.8 (24.1-47.3) | 15.7 (9.1-26.9) | 41.6 (32.8-52.7) | 57.6 (34.3-96.9) |
| $d_6$-(R)-7 | 13.4 (10.7-16.7) | 14.1 (8.4-23.6) | 12.5 (7.7-20.3) | 13.4 (10.7-16.7) | 25.1 (15.4-40.6) |
| $d_3$-(R)-8* | NT | NT | NT | NT | NT |
| 1[f] | 57.7 (45.5-73.1) | 95.3 (79.6-114.1) | 16.8 (11.6-24.2) | >130 | 77.3 (60.2-99.3) |
| 2[f] | 23.6 (13.8-40.4) | 73.3 (57.4-93.5) | 16.7 (11.6-24.1) | 38.1 (27.7-52.5) | 78.3 (85.8-93.1) |
| VPA[g] | 252.7 (220.1-290.2) | NT | 130.6 (117.6-145.2) | NT | 183.1 (143.5-233.7) |

| | Test | | | | |
|---|---|---|---|---|---|
| | $ED_{50}$ 6 Hz (44 mA)[c] | $ED^{50}$ scPTZ[d] | | $TD_{50}$ Rotarod[e] | |
| | Time | | | | |
| | 2.0 h | 0.5 h | 2.0 h | 0.5 h | 2.0 h |
| $d_4$-(R)-1 | 125.3 (98.9-158.6) | 33.5 (23.3-48.3) | 83.51 (65.9-105.7) | 176.7 (126.8-246.0) | >300 |
| $d_9$-(R)-2 | 109.8 (86.1-140.2) | 36.3 (24.7-53.1) | 85.6 (57.1-128.4) | 165.4 (131.4-208.2) | >300 |
| $d_5$-(R)-3* | NT | NT | NT | NT | NT |
| $d_4$-(R)-4 | 36.3 (24.8-53.1) | NT | NT | 127.2 (112.6-143.5) | >300 |
| $d_6$-(R)-5 | 50.8 (45.3-57.1) | NT | NT | >100 | >300 |
| $d_{11}$-(R)-6 | 70.4 (62.1-79.8) | NT | NT | >100 | >300 |
| $d_6$-(R)-7 | 33.5 (23.3-48.3) | NT | NT | >100 | >300 |
| $d_3$-(R)-8* | NT | NT | NT | NT | NT |
| 1[f] | >200 | 30.6 | >130 | 236.2 (225.7-247.1) | >300 |

TABLE 6-continued

| ED$_{50}$ and TD$_{50}$ values of parent compounds 1 and 2 and their deuterated analogues. | | | | | |
|---|---|---|---|---|---|
| 2[f] | 86.8 (79.3-95.2) | (14.0-66.8) | | >100 | >300 |
| VPA[g] | NT | 239.4 (209.2-274.1) | NT | 430.7 (407.9-454.9) | NT |

Compounds were tested 0.5 h and 2 h after i.p. administration. The substances were dissolved in a mixture of DMSO, PEG400 and water for injection (1:4:5, v/v/v). VPA (valproic acid), which is a model antiepileptic drug, was tested for 0.5 h.

[a]MES—maximal electroshock test.

[b]6 Hz (32 mA)—test of psychomotor seizures induced by a 32 mA electrical stimulus of a low frequency (6 Hz).

[c]6 Hz (44 mA)—test of psychomotor seizures induced by a 44 mA electrical stimulus of a low frequency (6 Hz).

[d]scPTZ—subsutaneous pentylenetetrazole-induced (scPTZ) seizure test.

[e]Rotarod test, a measure of acute neurotoxicity.

[f]Compound 1 and 2 - structures are disclosed in patent applications P.429656 and PCT/PL2020/050028 and patent Pat. 240297. Biological data obtained for formulation: DMSO/PEG400/water for injection (1:4:5, v/v/v).

[g]VPA (valproic acid)—a reference antiepileptic drug with a broad spectrum of activity in preclinical studies. Own data disclosed in Abram, M. et al. *Bioorg. Chem.* 2021, 109, 104751.

*Compounds d$_5$-(R)-3 and d$_3$-(R)-8 have not been studied due to the identical pharmacokinetic profile compared to the parent compound 1.

Abbreviations:

NT—not tested.

Antinociceptive Activity:

Compound d$_4$-(R)-1, which is a particularly preferred embodiment of the invention, in addition to anticonvulsant activity, exhibits antinociceptive activity in a number of pain tests/models, i.e. the formalin-induced tonic pain test, the capsaicin-induced pain test and models of neuropathic pain, i.e. oxaliplatin (OXPT)-induced peripheral neuropathy and t streptozotocin (STZ)-induced diabetic neuropathy model.

Evaluation of Analgesic Activity in the Formalin Test

Pain was induced with a chemical agent by intraplantar injection of 2.5% formalin solution in mice in a constant volume of 20 μL. The animals were placed in separate, transparent observation chambers for a period of 30 minutes. The measured value was the total licking and biting time of the formalin-treated paw. The nociceptive response was counted in two time intervals: 0-5 minutes from formalin injection (phase I of the test—acute pain) and 15-30 minutes from its administration (phase II of the test—inflammatory pain). The observed inhibition of the nociceptive response—shortening the time of licking and biting the paw, was interpreted as an analgesic effect of the tested compound.

In the formalin test, d$_4$-(R)-1 administered intraperitoneally showed potent analgesic activity in both phases of the test (FIG. 14). The mean nociceptive response in the control group was 66.72±6.56 seconds and 191.40±20.46 seconds for the first and second phase of the test, respectively. Compound d$_4$-(R)-1 at all tested doses reduced the nociceptive response in the first phase of the formalin test to 46.80% (dose of 30 mg/kg), 49.85% (dose of 60 mg/kg), 64.40% (dose of 90 mg/kg), and 39.68% (dose of 120 mg/kg) of the baseline (i.e. control), with a statistically significant effect observed for three doses—30, 60 and 120 mg/kg. In the second phase of the test corresponding to tonic inflammatory pain, compound d$_4$-(R)-1 reduced the nociceptive response to 46.04% (30 dose of mg/kg), 56.06% (dose of 60 mg/kg), 43.36% (dose of 90 mg/kg), and 30.24% (dose of 120 mg/kg) of baseline (i.e., control). Based on the obtained results, the ED$_{50}$ dose was calculated (the dose reducing the nociceptive response by 50%). The ED$_{50}$ values were 97.9 mg/kg (phase I) and 71.5 mg/kg (phase II), respectively.

Evaluation of Analgesic Activity in a Capsaicin-Induced Pain Model

This test evaluated the licking and/or biting time of the hind paw after intraplantar injection of 1.6 μg of capsaicin in a constant volume of 20 μL. Observation was carried out in the period of 5 minutes after capsaicin administration. Inhibition of the nociceptive response—shortening the time of licking and biting the paw, was a measure of the antinociceptive activity of the tested compound.

The nociceptive response in the control group was 66.50±3.94 seconds. Compound d$_4$-(R)-1 administered intraperitoneally statistically significantly decreased nociceptive response at all doses to 31.77% (dose of 30 mg/kg), 38.72% (dose of 60 mg/kg), 10.90% (dose of 90 mg/kg), respectively, of the initial value (i.e. control). Its ED$_{50}$ value was 17.5 mg/kg (FIG. 15).

Oxaliplatin (OXPT)-Induced Peripheral Neuropathy Model—Von Frey Test

A single administration of OXPT resulted in a lowered pain threshold in animals in response to a mechanical stimulus as measured by the von Frey method (Frey instrument/fiber, Bioseb, France). The reaction was observed before administration and 3 hours (early phase) and 7 days (late phase) after administration of OXPT.

The mean force that triggered the paw withdrawal reaction (pain threshold) in healthy mice (i.e. before OXPT administration) was 5.15±0.24 g (first group), 6.16±0.26 g (second group) and 6.37±0.40 g (third group). In the first group, a significant decrease in pain threshold to 3.97±0.23 g (77.1% of the baseline) was observed three hours after OXPT administration. Administration of d$_4$-(R)-1 at a dose of 30 mg/kg increased the pain threshold to 5.73±0.40 g (111.3% of baseline). Seven days after OXPT administration, the pain threshold was 4.46±0.20 g (86.6% of baseline) and d$_4$-(R)-1 at a dose of 30 mg/kg increased it to 6.38±0.50 g (123.9% of baseline). In the second group, a significant decrease in the pain threshold to 3.93±0.40 g (63.8% of the baseline) was observed three hours after OXPT administration. Administration of d$_4$-(R)-1 at 60 mg/kg resulted in an increase in pain threshold to 5.33±0.427 g (86.5% of baseline). Seven days after OXPT administration, the pain threshold was 3.57±0.31 g (57.9% of baseline) and d$_4$-(R)-1 at 60 mg/kg increased the value to 7.34±0.42 g (119.2% of baseline). In the third group, a significant decrease in pain threshold to 3.30±0.27 g (51.2% of baseline) was observed three hours after OXPT administration. Administration of d$_4$-(R)-1 at a dose of 90 mg/kg increased the pain threshold to 7.23±0.42 g (113.5% of baseline). Seven days after OXPT administration, the pain threshold was 4.78±0.34 g (75.0% of baseline) and d$_4$-(R)-1 at 90 mg/kg raised the value to 7.04±0.31 g (110.5% of baseline) (FIG. 16).

Streptozotocin-Induced Diabetic Neuropathic Pain Model—Von Frey's Test

A single administration of streptozotocin resulted in the development of hyperglycemia (plasma glucose concentration exceeded 300 mg/dIL) and a decrease in the pain threshold in animals in response to a mechanical stimulus (mechanical allodynia, von Frey test). The response was tested 3 weeks after the streptozotocin injection. Compound $d_4$-(R)-1 administered intraperitoneally at doses of 30, 60, and 90 mg/kg in a statistically significant and dose-dependent manner led to an increase in pain threshold compared to the measurement made before administration of the compound. Importantly, $d_4$-(R)-1 completely abolished the symptoms of developing sensory neuropathy at all doses.

The average force that triggered the paw withdrawal reaction (pain threshold) in the group of healthy mice (before STZ administration) was 5.89±0.20 g. In the first group, three weeks after STZ administration, a slight decrease in pain threshold was observed to 5.22±0.45 g (88.6% of baseline). Administration of $d_4$-(R)-1 at dose of 30 mg/kg resulted in an increase in pain threshold to 6.80±0.54 g (115.4% of baseline). In the second group, a significant decrease in pain threshold to 4.53±0.45 g (76.9% of the baseline) was observed three weeks after the administration of STZ. Administration of $d_4$-(R)-1 at dose of 60 mg/kg resulted in an increase in pain threshold to 8.64±0.72 g (146.6% of baseline). In the third group, a significant decrease in pain threshold to 4.99±0.29 g (84.7% of the baseline) was observed three weeks after the administration of STZ. Administration of $d_4$-(R)-1 at a dose of 90 mg/kg resulted in an increase in the pain threshold to 9.40±0.61 g (159.6% of baseline) (FIG. 17).

Due to the fact that the other derivatives containing deuterium atoms in the structure are close analogues (bioisosteres) of compound $d_4$-(R)-1, which, similarly to $d_4$-(R)-1, showed strong anticonvulsant activity in the in vivo studies, it should be expected that these substances, like $d_4$-(R)-1, also have a strong and broad-spectrum antinociceptive activity, resulting from bioisosteric H/D replacement.

Influence on the Spontaneous Locomotor Activity in Animals

The influence of $d_4$-(R)-1 on spontaneous locomotor activity was also studied to evaluate its potential sedative properties. Strong sedative activity is an undesirable property that may lead to misinterpretation or inconclusive interpretation of antinociceptive tests results. For this purpose, the number of light beam crossings in the cages was counted in each group of animals during a 30-minute observation. The number of light beam crossings for mice treated with vehicle (i.e. 1% aqueous Tween 80) was 1678.0±150.0. It was significantly reduced to a value corresponding to 46.90% of the initial value after administration of the compound only at a dose of 30 mg/kg. Administration of $d_4$-(R)-1 at doses of 60 mg/kg, 90 mg/kg, and 120 mg/kg resulted in an increase of locomotor activity to 106.30%, 115.73%, and 118.95% of baseline, respectively, but these results were not statistically significant (FIG. 18). Thus, the disclosed data prove that $d_4$-(R)-1 is devoid of sedative effects, and the results obtained in pain models are reliable and clearly indicate the antinociceptive potential of this compound.

In Vitro Metabolic Stability

The metabolic stability of the deuterated compound $d_4$-(R)-1, which is an example of particularly preferred embodiment of the invention, and the parent molecule, i.e. 1, were tested in vitro by their 120-minute incubation with mouse liver microsomes (MLMs) in the presence of the NADPH as cofactor. Based on the obtained UPLC chromatograms frm the reaction mixture, no metabolites appeared in both cases, which proves the very high metabolic stability of both tested substances (FIG. 19). Compounds 1 and 2 and their deuterated analogues $d_4$-(R)-1, $d_9$-(R)-2, $d_4$-(R)-4, $d_6$-(R)-5, $d_{11}$-(R)-6, and $d_6$-(R)-7 have similar high metabolic stability after their 120-minute incubation with human liver microsomes (HLMs).

The excellent metabolic stability of the deuterated compound $d_4$-(R)-1 and the parent molecule 1 in MLMs proves that the beneficial isotope effect observed in vivo (i.e. improvement of pharmacokinetic parameters, including $t_{0.5}$ extension) for the deuterated derivatives being the object of the present invention is completely non-obvious in terms of the results obtained from in vitro metabolic stability studies.

Methodology

Chemical Research

Analytical Methods

Proton nuclear magnetic resonance ($^1$H NMR) and carbon nuclear magnetic resonance ($^{13}$C NMR) spectra were recorded using a JEOL-500 spectrometer (JEOL USA, Inc. MA, USA) at 500 MHz and 126 MHz, respectively. Chemical shifts are given in δ (ppm) values relative to TMS 67=0 (1H) as an internal standard. J values are expressed in hertz (Hz). Deuterated chloroform ($CDCl_3$) was used as the solvent. The following signal abbreviations were used in the description of the spectra: br s (broad singlet), d (doublet), dd (doublet of doublets), t (triplet), td (triplet of doublets), q(quartet), qd (quartet of doublets), m (multiplet). The UPLC/MS analysis system consisted of a Waters ACQUITY® UPLC® instrument (Waters Corporation, Milford, MA, USA) coupled to a Waters TQD mass spectrometer operating in electrospray ionization (ESI) mode. Chromatographic separations were carried out using an Acquity UPLC BEH C18 column with dimensions of 2.1×100 mm and a grain diameter of 1.7 μm. The column was kept at 40° C. and eluted with a gradient from 95% to 0% of eluent A over 10 min at a flow rate of 0.3 mL $min^{-1}$. Eluent A: water/formic acid (0.1%, v/v); eluent B: acetonitrile/formic acid (0.1%, v/v). Chromatograms were recorded using a PDA Waters eλ detector. Spectra were analyzed in the range of 200-700 nm with a resolution of 1.2 nm and a sampling rate of 20 points/s. Thin layer chromatography (TLC) was performed on aluminum plates coated with silica gel 60 $F_{254}$ (Macherey-Nagel, Düren, Germany) using developing systems with the following composition: DCM:MeOH (9:0.3; v/v), DCM:MeOH (9:0.5; v/v), spot detection—UV light (λ=254 nm). Melting points (m.p.) were determined using open capillaries in a Büchi 353 apparatus (Büchi Labortechnik, Flawil, Switzerland). Enantiomeric purity for compounds $d_4$-(R)-1, $d_9$-(R)-2, $d_5$-(R)-3, $d_4$-(R)-4, $d_6$-(R)-5, $d_{11}$-(R)-6, $d_6$-(R)-7, $d_4$-(S)-1, $d_9$-(S)-2, $d_5$-(S)-3, $d_4$-(S)-4, $d_6$-(S)-5, $d_{11}$-(S)-6, $d_6$-(S)-7 were determined by chiral HPLC spectral analysis using a Shimadzu Prominence i Ic 2030c plus apparatus (Shimadzu Corporation, Kyoto, Japan) equipped with an Amylose-C chiral column (250×4.6 mm). The analysis was performed under the following conditions: column temperature: 20° C., eluent mixture: hexane/i-PrOH=85/15 (v/v), flow: 0.7 mL/min, detection at λ=209 nm. Chemical names for compounds representing exemplary embodiments of the invention were generated using the ChemBioDraw Ultra 12.0 program. The presented syntheses of intermediates and final products were not optimized in terms of yield, the amount of reagents used, and the final form of the compounds obtained.

The method of obtaining parent compounds 1 and 2 is disclosed in patent applications P.429656, PCT/PL2020/050028 and patent Pat.240297.

Abbreviations used:

AcOEt—ethyl acetate

DCC—N,N'-dicyclohexylcarbodiimide

DCM—dichloromethane $Et_2O$—diethyl ether

HCl—hydrochloric acid

HMDS—hexamethyldisilazane

MeOH—methanol

NaCl—sodium chloride $NH_4OH$—ammonium hydroxide $Na_2SO_4$—sodium sulfate

TFA—trifluoroacetic acid $ZnCl_2$—zinc chloride

Examples of Synthesis and Physicochemical and Spectral Data of Intermediate Products (II, Ill and IV According to Scheme 1):

Scheme 1. Synthesis of compounds described by formula (I) according to the invention.

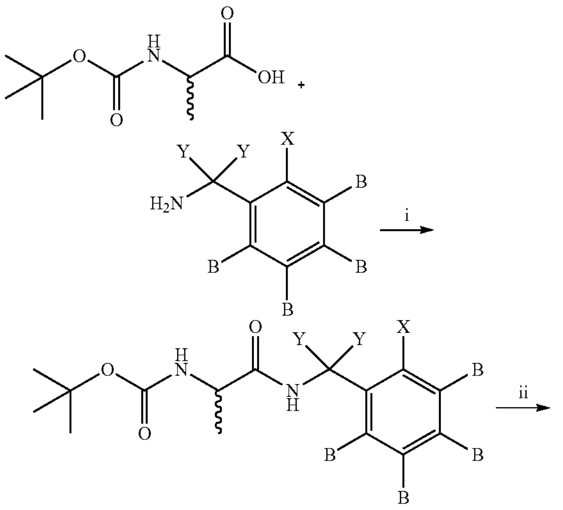

(IV)

(R)-IV: B = H, X = H, Y = H
(R)-IV: B = D, X = D, Y = H
(R)-IV: B = H, X = F, Y = H
(R)-IV: B = H, X = H, Y = D
(R)-IV: B = D, X = D, Y = D
(R)-IV: B = H, X = F, Y = D (S)-IV: B = H, X = H, Y = H
(S)-IV: B = D, X = D, Y = H
(S)-IV: B = H, X = F, Y = H
(S)-IV: B = H, X = H, Y = D
(S)-IV: B = D, X = D, Y = D
(S)-IV: B = H, X = F, Y = D (R,S)-IV: B = H, X = H, Y = H
(R,S)-IV: B = D, X = D, Y = H
(R,S)-IV: B = H, X = F, Y = H
(R,S)-IV: B = H, X = H, Y = D
(R,S)-IV: B = D, X = D, Y = D
(R,S)-IV: B = H, X = F, Y = D

-continued

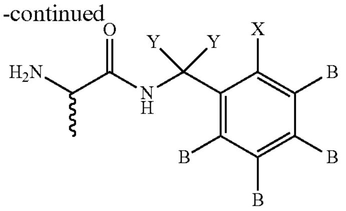

(III)

(R)-III: B = H, X = H, Y = H
(R)-III: B = D, X = D, Y = H
(R)-III: B = H, X = F, Y = H
(R)-III: B = H, X = H, Y = D
(R)-III: B = D, X = D, Y = D
(R)-III: B = H, X = F, Y = D (S)-III: B = H, X = H, Y = H
(S)-III: B = D, X = D, Y = H
(S)-III: B = H, X = F, Y = H
(S)-III: B = H, X = H, Y = D
(S)-III: B = D, X = D, Y = D
(S)-III: B = H, X = F, Y = D (R,S)-III: B = H, X = H, Y = H
(R,S)-III: B = D, X = D, Y = H
(R,S)-III: B = H, X = F, Y = H
(R,S)-III: B = H, X = H, Y = D
(R,S)-III: B = D, X = D, Y = D
(R,S)-III: B = H, X = F, Y = D

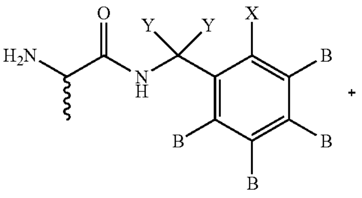

(III)

(R)-III: B = H, X = H, Y = H
(R)-III: B = D, X = D, Y = H
(R)-III: B = H, X = F, Y = H
(R)-III: B = H, X = H, Y = D
(R)-III: B = D, X = D, Y = D
(R)-III: B = H, X = F, Y = D (S)-III: B = H, X = H, Y = H
(S)-III: B = D, X = D, Y = H
(S)-III: B = H, X = F, Y = H
(S)-III: B = H, X = H, Y = D
(S)-III: B = D, X = D, Y = D
(S)-III: B = H, X = F, Y = D (R,S)-III: B = H, X = H, Y = H
(R,S)-III: B = D, X = D, Y = H
(R,S)-III: B = H, X = F, Y = H
(R,S)-III: B = H, X = H, Y = D
(R,S)-III: B = D, X = D, Y = D
(R,S)-III: B = H, X = F, Y = D

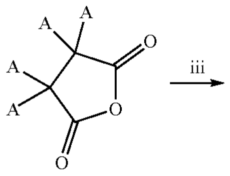

-continued

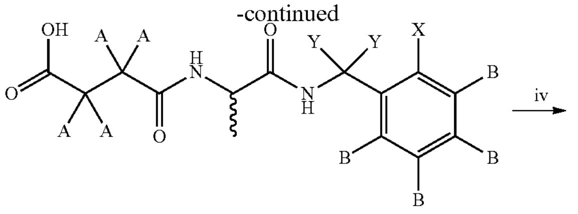

(II)

(R)-II: A = D, B = H, X = H, Y = H
(R)-II: A = H, B = D, X = D, Y = H
(R)-II: A = D, B = D, X = D, Y = H
(R)-II: A = D, B = H, X = F, Y = H
(R)-II: A = D, B = H, X = H, Y = D
(R)-II: A = D, B = D, X = D, Y = D
(R)-II: A = D, B = H, X = F, Y = D (S)-II: A = D, B = H, X = H, Y = H
(S)-II: A = H, B = D, X = D, Y = H
(S)-II: A = D, B = D, X = D, Y = H
(S)-II: A = D, B = H, X = F, Y = H
(S)-II: A = D, B = H, X = H, Y = D
(S)-II: A = D, B = D, X = D, Y = D
(S)-II: A = D, B = H, X = F, Y = D (R,S)-II: A = D, B = H, X = H, Y = H
(R,S)-II: A = H, B = D, X = D, Y = H
(R,S)-II: A = D, B = D, X = D, Y = H
(R,S)-II: A = D, B = H, X = F, Y = H
(R,S)-II: A = D, B = H, X = H, Y = D
(R,S)-II: A = D, B = D, X = D, Y = D
(R,S)-II: A = D, B = H, X = F, Y = D

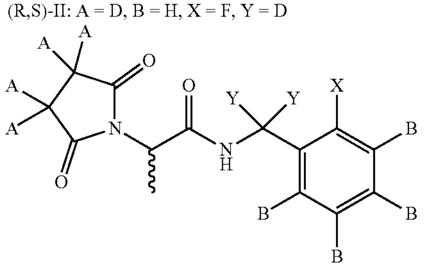

(I)

$d_4$-(R)-1: A = D, B = H, X = H, Y = H
$d_9$-(R)-2: A = D, B = D, X = D, Y = H
$d_5$-(R)-3: A = H, B = D, X = D, Y = H
$d_4$-(R)-4: A = D, B = H, X = F, Y = H
$d_6$-(R)-5: A = D, B = H, X = H, Y = D
$d_{11}$-(R)-6: A = D, B = D, X = D, Y = D
$d_6$-(R)-7: A = D, B = H, X = F, Y = D $d_4$-(S)-1: A = D, B = H, X = H, Y = H
$d_9$-(S)-2: A = D, B = D, X = D, Y = H
$d_5$-(S)-3: A = H, B = D, X = D, Y = H
$d_4$-(S)-4: A = D, B = H, X = F, Y = H
$d_6$-(S)-5: A = D, B = H, X = H, Y = D
$d_{11}$-(S)-6: A = D, B = D, X = D, Y = D
$d_6$-(S)-7: A = D, B = H, X = F, Y = D $d_4$-(R,S)-1: A = D, B = H, X = H, Y = H
$d_9$-(R,S)-2: A = D, B = D, X = D, Y = H
$d_5$-(R,S)-3: A = H, B = D, X = D, Y = H
$d_4$-(R,S)-4: A = D, B = H, X = F, Y = H
$d_6$-(R,S)-5: A = D, B = H, X = H, Y = D
$d_{11}$-(R,S)-6: A = D, B = D, X = D, Y = D
$d_6$-(R,S)-7: A = D, B = H, X = F, Y = D

Reaction conditions:
i - DCC, DCM, rt, 4 h
ii - TFA, rt, 2 h
iii - AcOEt, rt, 30 min
iv - HMDS, $ZnCl_2$,1,4-dioxane,reflux, 24 h Example 1. Intermediate (R)-IV (where B=H, X=H, Y=H); tert-butyl (R)-(1-(benzylamino)-1-oxopropan-2-yl)carbamate Boc-D-alanine (5.0 g, 27 mmol, 1 eq) was dissolved in 20 mL of dichloromethane (DCM), then DCC (6.81 g, 1.2 eq) was added, and after 30 minutes benzylamine (2.95 g, 1 eq) was added, dropwise. The reaction was continued with stirring at room temperature for 4 hours. After this time, DCM was distilled off to dryness. The intermediate was purified by column chromatography with DCM:MeOH (9:0.3; v/v) eluents system. The compound was obtained as a colorless, clear oil.

Yield: 91% (6.95 g); TLC: $R_f$=0.43 (DCM:MeOH (9:0.3; v/v)); $C_{15}H_{22}N_2O_3$ (278.35), Monoisotopic mass: 279.16. UPLC (purity>99%): $t_R$=5.44 min. $(M+H)^+$ 279.3.

Example 2. Intermediate (R)-IV (where B=D, X=D, Y=H); tert-butyl (R)-(1-oxo-1-(((phenyl-$d_5$)methyl) amino)propan-2-yl)carbamate The compound was obtained using an analogous procedure to that described above. Boc-D-alanine (5.0 g, 27 mmol, 1 eq) and DCC (6.81 g, 1.2 eq) and benzylamine-$d_5$ (3.09 g, 1 eq) were used in the reaction. The crude product was purified by column chromatography with DCM:MeOH (9:0.3; v/v) eluents system. The compound was obtained as a colorless, clear oil.

Yield: 92% (7.08 g); TLC: $R_f$=0.43 (DCM:MeOH (9:0.3; v/v)); $C_{15}H_{17}D_5N_2O_3$ (283.38), Monoisotope mass: 284.19. UPLC (purity>99%): $t_R$=5.41 min. $(M+H)^+$ 284.1.

Example 3. Intermediate (R)-IV (where B=H, X=F, Y=H); tert-butyl (R)-(1-((2-fluorobenzyl)amino)-1-oxopropan-2-yl)carbamate The compound was obtained using an analogous procedure to that described above. Boc-D-alanine (5.0 g, 27 mmol, 1 eq) and DCC (6.81 g, 1.2 eq) and 2-fluorobenzylamine (3.31 g, 1 eq) were used in the reaction. The crude product was purified by column chromatography with DCM MeOH (9:0.3; v/v) eluents system. The compound was obtained as a colorless, clear oil.

Yield: 93% (7.28 g); TLC: $R_f$=0.45 (DCM:MeOH (9:0.3; v/v)); $C_{15}H_{21}FN_2O_3$ (296.34), Monoisotopic mass: 297.15. UPLC (purity>99%): $t_R$=5.54 min. $(M+H)^+$ 297.2.

Example 4. Intermediate (R)-IV (where B=H, X=H, Y=D); tert-butyl (R)-(1-oxo-1-((phenylmethyl-$d_2$) amino)propan-2-yl)carbamate The compound was obtained using an analogous procedure to that described above. Boc-D-alanine (5.0 g, 27 mmol, 1 eq) and DCC (6.81 g, 1.2 eq) and benzylamine-$d_2$ (3.01 g, 1 eq) were used in the reaction. The crude product was purified by column chromatography with DCM:MeOH (9:0.3; v/v) eluents system. The compound was obtained as a colorless, clear oil.

Yield: 93% (7.18 g); TLC: $R_f$=0.43 (DCM:MeOH (9:0.3; v/v)); $C_{15}H_{20}D_2N_2O_3$ (280.36), Monoisotope mass: 281.18. UPLC (purity>99%): $t_R$=5.43 min. $(M+H)^+$ 281.2.

Example 5. Intermediate (R)-IV (where B=D, X=D, Y=D); tert-butyl (R)-(1-oxo-1-(((phenyl-$d_5$) methyl-$d_2$)amino)propan-2-yl)carbamate The compound was obtained using an analogous procedure to that described above. Boc-D-alanine (5.0 g, 27 mmol, 1 eq) and DCC (6.81 g, 1.2 eq) and benzylamine-$d_7$ (3.15 g, 1 eq) were used in the reaction. The crude product was purified by column chromatography with DCM:MeOH (9:0.3; v/v) eluents system. The compound was obtained as a colorless, clear oil.

Yield: 94% (7.39 g); TLC: $R_f$=0.43 (DCM:MeOH (9:0.3; v/v)); $C_{15}H_{15}D_7N_2O_3$ (285.39), Monoisotope mass: 286.21. UPLC (purity>99%): $t_R$=5.42 min. $(M+H)^+$ 286.3.

Example 6. Intermediate (R)-IV (where B=H, X=F, Y=D); tert-butyl (R)-(1-(((2-fluorophenyl)methyl-$d_2$)amino)-1-oxopropan-2-yl)carbamate The compound was obtained using an analogous procedure to that described above. Boc-D-alanine (5.0 g, 27 mmol, 1 eq) and DCC (6.81 g, 1.2 eq) and 2-fluorobenzylamine-$d_2$ (3.36 g, 1 eq) were used in the reaction. The crude product was purified by column chromatography with DCM:MeOH (9:0.3; v/v) eluents system. The compound was obtained as a colorless, clear oil.

Yield: 93% (7.33 g); TLC: $R_f$=0.45 (DCM:MeOH (9:0.3; v/v)); $C_{15}H_{19}D_2FN_2O_3$ (298.35), Monoisotopic mass: 299.17. UPLC (purity>99%): $t_R$=5.53 min. $(M+H)^+$ 299.2.

Example 7. Intermediate(S)-IV (where B=H, X=H, Y=H); tert-butyl(S)-(1-(benzylamino)-1-oxopropan-2-yl)carbamate The compound was obtained using an analogous procedure to that described above. Boc-L-alanine (5.0 g, 27 mmol, 1 eq) and DCC (6.81 g, 1.2 eq) and benzylamine (2.95 g, 1 eq) were used in the reaction. The crude product was purified by column chromatography with DCM:MeOH (9:0.3; v/v) eluents system. The compound was obtained as a colorless, clear oil.

Yield: 90% (6.86 g); TLC: $R_f$=0.43 (DCM:MeOH (9:0.3; v/v)); $C_{15}H_{22}N_2O_3$ (278.35), Monoisotopic mass: 279.16. UPLC (purity>99%): $t_R$=5.43 min. $(M+H)^+$ 279.3.

Example 8. Intermediate(S)-IV (where B=D, X=D, Y=H); tert-butyl(S)-(1-oxo-1-(((phenyl-$d_5$)methyl)amino)propan-2-yl)carbamate The compound was obtained using an analogous procedure to that described above. Boc-L-alanine (5.0 g, 27 mmol, 1 eq) and DCC (6.81 g, 1.2 eq), and benzylamine-$d_5$ (3.09 g, 1 eq) were used in the reaction. The crude product was purified by column chromatography with DCM:MeOH (9:0.3; v/v) eluents system. The compound was obtained as a colorless, clear oil.

Yield: 90% (6.92 g); TLC: $R_f$=0.43 (DCM:MeOH (9:0.3; v/v)); $C_{15}H_{17}D_5N_2O_3$ (283.38), Monoisotope mass: 284.19. UPLC (purity>99%): $t_R$=5.40 min. $(M+H)^+$ 284.2.

Example 9. Intermediate(S)-IV (where B=H, X=F, Y=H); tert-butyl(S)-(1-((2-fluorobenzyl)amino)-1-oxopropan-2-yl)carbamate The compound was obtained using an analogous procedure to that described above. Boc-L-alanine (5.0 g, 27 mmol, 1 eq) and DCC (6.81 g, 1.2 eq) and 2-fluorobenzylamine (3.31 g, 1 eq) were used in the reaction. The crude product was purified by column chromatography with DCM:MeOH (9:0.3; v/v) eluents system. The compound was obtained as a colorless, clear oil.

Yield: 92% (7.20 g); TLC: $R_f$=0.45 (DCM:MeOH (9:0.3; v/v)); $C_{15}H_{21}FN_2O_3$ (296.34), Monoisotopic mass: 297.15. UPLC (purity>99%): $t_R$=5.55 min. $(M+H)^+$ 297.2.

Example 10. Intermediate(S)-IV (where B=H, X=H, Y=D); tert-butyl(S)-(1-oxo-1-((phenylmethyl-$d_2$)amino)propan-2-yl)carbamate The compound was obtained using an analogous procedure to that described above. Boc-L-alanine (5.0 g, 27 mmol, 1 eq) and DCC (6.81 g, 1.2 eq) and benzylamine-$d_2$ (3.01 g, 1 eq) were used in the reaction. The crude product was purified by column chromatography with DCM:MeOH (9:0.3; v/v) eluents system. The compound was obtained as a colorless, clear oil.

Yield: 91% (7.03 g); TLC: $R_f$=0.43 (DCM:MeOH (9:0.3; v/v)); $C_{15}H_{20}D_2N_2O_3$ (280.36), Monoisotope mass: 281.18. UPLC (purity>99%): $t_R$=5.43 min. $(M+H)^+$ 281.1.

Example 11. Intermediate(S)-IV (where B=D, X=D, Y=D); tert-butyl(S)-(1-oxo-1-(((phenyl-$d_5$)methyl-$d_2$)amino)propan-2-yl)carbamate The compound was obtained using an analogous procedure to that described above. Boc-L-alanine (5.0 g, 27 mmol, 1 eq) and DCC (6.81 g, 1.2 eq) and benzylamine-$d_7$ (3.15 g, 1 eq) were used in the reaction. The crude product was purified by column chromatography with DCM:MeOH (9:0.3; v/v) eluents system. The compound was obtained as a colorless, clear oil.

Yield: 91% (7.14 g); TLC: $R_f$=0.43 (DCM:MeOH (9:0.3; v/v)); $C_{15}H_{15}D_7N_2O_3$ (285.39), Monoisotope mass: 286.21. UPLC (purity>99%): $t_R$=5.42 min. $(M+H)^+$ 286.3.

Example 12. Intermediate(S)-IV (where B=H, X=F, Y=D); tert-butyl(S)-(1-(((2-fluorophenyl)methyl-$d_2$)amino)-1-oxopropan-2-yl)carbamate The compound was obtained using an analogous procedure to that described above. Boc-L-alanine (5.0 g, 27 mmol, 1 eq) and DCC (6.81 g, 1.2 eq) and 2-fluorobenzylamine-$d_2$ (3.36 g, 1 eq) were used in the reaction. The crude product was purified by column chromatography with DCM:MeOH (9:0.3; v/v) eluents system. The compound was obtained as a colorless, clear oil.

Yield: 89% (7.01 g); TLC: $R_f$=0.45 (DCM:MeOH (9:0.3; v/v)); $C_{15}H_{19}D_2FN_2O_3$ (298.35), Monoisotopic mass: 299.17. UPLC (purity>99%): $t_R$=5.53 min. $(M+H)^+$ 299.3.

Example 13. Intermediate (R,S)-IV (where B=H, X=H, Y=H); tert-butyl (R,S)-(1-(benzylamino)-1-oxopropan-2-yl)carbamate The compound was obtained using an analogous procedure to that described above. Boc-D,L-alanine (5.0 g, 27 mmol, 1 eq) and DCC (6.81 g, 1.2 eq) and benzylamine (2.95 g, 1 eq) were used in the reaction. The crude product was purified by column chromatography with DCM:MeOH (9:0.3; v/v) eluents system. The compound was obtained as a colorless, clear oil.

Yield: 93% (7.16 g); TLC: $R_f$=0.43 (DCM:MeOH (9:0.3; v/v)); $C_{15}H_{22}N_2O_3$ (278.35), Monoisotopic mass: 279.16. UPLC (purity>99%): $t_R$=5.42 min. $(M+H)^+$ 279.1.

Example 14. Intermediate (R,S)-IV (where B=D, X=D, Y=H); tert-butyl (R,S)-(1-oxo-1-(((phenyl-$d_5$)methyl)amino)propan-2-yl)carbamate The compound was obtained using an analogous procedure to that described above. Boc-D,L-alanine (5.0 g, 27 mmol, 1 eq) and DCC (6.81 g, 1.2 eq) and benzylamine-$d_5$ (3.09 g, 1 eq) were used in the reaction. The crude product was purified by column chromatography with DCM:MeOH (9:0.3; v/v) eluents system. The compound was obtained as a colorless, clear oil.

Yield: 89% (6.85 g); TLC: $R_f$=0.43 (DCM:MeOH (9:0.3; v/v)); $C_{15}H_{17}D_5N_2O_3$ (283.38), Monoisotope mass: 284.19. UPLC (purity>99%): $t_R$=5.43 min. $(M+H)^+$ 284.2.

Example 15. Intermediate (R,S)-IV (where B=H, X=F, Y=H); tert-butyl (R,S)-(1-((2-fluorobenzyl) amino)-1-oxopropan-2-yl)carbamate The compound was obtained using an analogous procedure to that described above. Boc-D,L-alanine (5.0 g, 27 mmol, 1 eq) and DCC (6.81 g, 1.2 eq) and 2-fluorobenzylamine (3.31 g, 1 eq) were used in the reaction. The crude product was purified by column chromatography with DCM:MeOH (9:0.3; v/v) eluents system. The compound was obtained as Yield: 90% (7.05 g); TLC: $R_f$=0.45 (DCM:MeOH (9:0.3; v/v)); $C_{15}H_{21}FN_2O_3$ (296.34), Monoisotopic mass: 297.15. UPLC (>99% purity): $t_R$=5.56 min. $(M+H)^+$ 297.1.

Example 16. Intermediate (R,S)-IV (where B=H, X=H, Y=D); tert-butyl (R,S)-(1-oxo-1-((phenylmethyl-$d_2$)amino)propan-2-yl)carbamate The compound was obtained using an analogous procedure to that described above. Boc-D,L-alanine (5.0 g, 27 mmol, 1 eq) and DCC (6.81 g, 1.2 eq) and benzylamine-$d_2$ (3.01 g, 1 eq) were used in the reaction. The crude product was purified by column chromatography with DCM:MeOH (9:0.3; v/v) eluents system. The compound was obtained as a colorless, clear oil.

Yield: 92% (7.10 g); TLC: $R_f$=0.43 (DCM:MeOH (9:0.3; v/v)); $C_{15}H_{20}D_2N_2O_3$ (280.36), Monoisotope mass: 281.18. UPLC (purity>99%): $t_R$=5.43 min. $(M+H)^+$ 281.2.

Example 17. Intermediate (R,S)-IV (where B=D, X=D, Y=D); tert-butyl (R,S)-(1-oxo-1-(((phenyl-$d_5$) methyl-$d_2$)amino)propan-2-yl)carbamate The compound was obtained using an analogous procedure to that described above. Boc-D,L-alanine (5.0 g, 27 mmol, 1 eq) and DCC (6.81 g, 1.2 eq) and benzylamine-$d_7$ (3.15 g, 1 eq) were used in the reaction. The crude product was purified by column chromatography with DCM:MeOH (9:0.3; v/v) eluents system. The compound was obtained as a colorless, clear oil.

Yield: 91% (7.15 g); TLC: $R_f$=0.43 (DCM:MeOH (9:0.3; v/v)); $C_{15}H_{15}D_7N_2O_3$ (285.39), Monoisotope mass: 286.21. UPLC (purity>99%): $t_R$=5.41 min. $(M+H)^+$ 286.3.

Example 18. Intermediate (R,S)-IV (where B=H, X=F, Y=D); tert-butyl (R,S)-(1-(((2-fluorophenyl) methyl-$d_2$)amino)-1-oxopropan-2-yl)carbamate The compound was obtained using an analogous procedure to that described above. Boc-D,L-alanine (5.0 g, 27 mmol, 1 eq) and DCC (6.81 g, 1.2 eq) and 2-fluorobenzylamine-$d_2$ (3.36 g, 1 eq) were used in the reaction. The crude product was purified by column chromatography with DCM:MeOH (9:0.3; v/v) eluents system. The compound was obtained as a colorless, clear oil.

Yield: 90% (7.09 g); TLC: $R_f$=0.45 (DCM:MeOH (9:0.3; v/v)); $C_{15}H_{19}D_2FN_2O_3$ (298.35), Monoisotopic mass: 299.17. UPLC (purity>99%): $t_R$=5.54 min. $(M+H)^+$ 299.2.

Example 19. Intermediate (R)-III (where B=H, X=H, Y=H); (R)-2-amino-N-benzylpropanamide 10 mL of TFA was added to a solution of tert-butyl-(R)-(1-(benzylamino)-1-oxopropan-2-yl) carbamate (6.95 g, 25 mmol, 1 eq) in DCM (100 mL), the mixture was stirred for 2 hours, then neutralized with 25% $NH_4OH$ solution, and next extracted with DCM (3×50 mL). The organic layer was dried over anhydrous $Na_2SO_4$ and then evaporated to dryness. The compound was obtained as a colorless, clear oil.

Yield: 89% (3.9 g); TLC: $R_f$=0.21 (DCM:MeOH (9:0.5; v/v)); $C_{10}H_{14}N_2O$ (178.24), Monoisotopic mass: 179.11. UPLC (purity 96.8%): $t_R$=2.11 min. $(M+H)^+$ 179.2.

Example 20. Intermediate (R)-III (where B=D, X=D, Y=H); (R)-2-amino-N-((phenyl-$d_5$)methyl) propanamide The compound was obtained using an analogous procedure to that described above. Tert-butyl (R)-(1-oxo-1-(((phenyl-$d_5$)methyl)amino)propan-2-yl)carbamate (7.08 g, 25 mmol, 1 eq) and 10 mL of TFA were used in the reaction. The compound was obtained as a colorless, clear oil.

Yield: 94% (4.3 g); TLC: $R_f$=0.21 (DCM:MeOH (9:0.5; v/v)); $C_{10}H_9D_5N_2O$ (183.27), Monoisotope mass: 184.14. UPLC (purity 96.3%): $t_R$=2.16 min. $(M+H)^+$ 184.1.

Example 21. Intermediate (R)-III (where B=H, X=F, Y=H); (R)-2-amino-N-(2-fluorobenzyl)propanamide The compound was obtained using an analogous procedure to that described above. Tert-butyl (R)-(1-((2-fluorobenzyl)amino)-1-oxopropan-2-yl)carbamate (7.08 g, 25 mmol, 1 eq) and 10 ml of TFA were used in the reaction. The compound was obtained as a colorless, clear oil.

Yield: 92% (4.4 g); TLC: $R_f$=0.23 (DCM:MeOH (9:0.5; v/v)); $C_{10}H_{13}FN_2O$ (196.23), Monoisotopic mass: 197.10. UPLC (purity 97.4%): $t_R$=2.29 min. $(M+H)^+$ 197.2.

Example 22. Intermediate (R)-III (where B=H, X=H, Y=D); (R)-2-amino-N-(phenylmethyl-$d_2$)propanamide The compound was obtained using an analogous procedure to that described above. Tert-butyl (R)-(1-oxo-1-((phenylmethyl-$d_2$)amino)propan-2-yl)carbamate (7.01 g, 25 mmol, 1 eq) and 10 mL of TFA were used in the reaction. The compound was obtained as a colorless, clear oil.

Yield: 95% (4.3 g); TLC: $R_f$=0.21 (DCM:MeOH (9:0.5; v/v)); $C_{10}H_{12}D_2N_2O$ (180.25), Monoisotope mass: 181.12. UPLC (purity>99%): $t_R$=2.12 min. $(M+H)^+$ 181.3.

Example 23. Intermediate (R)-III (where B=D, X=D, Y=D); (R)-2-amino-N-((phenyl-$d_5$)methyl-$d_2$) propanamide The compound was obtained using an analogous procedure to that described above. Tert-butyl (R)-(1-oxo-1-(((phenyl-$d_5$)methyl-$d_2$)amino)propan-2-yl)carbamate (7.13 g, 25 mmol, 1 eq) and 10 ml of TFA were used in the reaction. The compound was obtained as a colorless, clear oil.

Yield: 95% (4.4 g); TLC: $R_f$=0.21 (DCM:MeOH (9:0.5; v/v)); $C_{10}H_7D_7N_2O$ (185.28), Monoisotope mass: 186.15. UPLC (purity>99%): $t_R$=2.14 min. $(M+H)^+$ 186.2.

Example 24. Intermediate (R)-III (where B=H, X=F, Y=D); (R)-2-amino-N-((2-fluorophenyl)methyl-$d_2$)propanamide The compound was obtained using an analogous procedure to that described above. Tert-butyl (R)-(1-(((2-fluorophenyl)methyl-$d_2$)amino)-1-oxopropan-2-yl)carbamate (6.86 g, 23 mmol, 1 eq) and 10 ml of TFA were used in the reaction. The compound was obtained as a colorless, clear oil.

Yield: 95% (4.3 g); TLC: $R_f$=0.23 (DCM:MeOH (9:0.5; v/v)); $C_{10}H_{11}D_2FN_2O$ (198.24), Monoisotopic mass: 199.11. UPLC (purity>99%): $t_R$=2.28 min. $(M+H)^+$ 199.2.

Example 25. Intermediate(S)-III (where B=H, X=H, Y=H); (S)-2-amino-N-benzylpropanamide The compound was obtained using an analogous procedure to that described above. Tert-butyl (S)-(1-(benzylamino)-1-oxopropan-2-yl)carbamate (6.50 g, 23 mmol, 1 eq) and 10 ml of TFA were used in the reaction. The compound was obtained as a colorless, clear oil.

Yield: 87% (3.67 g); TLC: $R_f$=0.21 (DCM:MeOH (9:0.5; v/v)); $C_{10}H_{14}N_2O$ (178.24), Monoisotopic mass: 179.11. UPLC (purity 96.8%): $t_R$=2.12 min. $(M+H)^+$ 179.2.

Example 26. Intermediate(S)-III (where B=D, X=D, Y=H); (S)-2-amino-N-((phenyl-$d_5$)methyl)propanamide The compound was obtained using an analogous procedure to that described above. Tert-butyl (S)-(1-oxo-1-(((phenyl-$d_5$)methyl)amino)propan-2-yl)carbamate (6.51 g, 23 mmol, 1 eq) and 10 mL of TFA were used in the reaction. The compound was obtained as a colorless, clear oil.

Yield: 95% (4.0 g); TLC: $R_f$=0.21 (DCM:MeOH (9:0.5; v/v)); $C_{10}H_9D_5N_2O$ (183.27), Monoisotope mass: 184.14. UPLC (purity 96.3%): $t_R$=2.15 min. $(M+H)^+$ 184.2.

Example 27. Intermediate(S)-III (where B=H, X=F, Y=H); (S)-2-amino-N-(2-fluorobenzyl)propanamide The compound was obtained using an analogous procedure to that described above. Tert-butyl (S)-(1-((2-fluorobenzyl)amino)-1-oxopropan-2-yl)carbamate (6.82 g, 23 mmol, 1 eq) and 10 ml of TFA were used in the reaction. The compound was obtained as a colorless, clear oil.

Yield: 93% (4.3 g); TLC: $R_f$=0.23 (DCM:MeOH (9:0.5; v/v)); $C_{10}H_{13}FN_2O$ (196.23), Monoisotopic mass: 197.10. UPLC (purity 98.2%): $t_R$=2.30 min. $(M+H)^+$ 197.1.

Example 28. Intermediate(S)-III (where B=H, X=H, Y=D); (S)-2-amino-N-(phenylmethyl-$d_2$)propanamide The compound was obtained using an analogous procedure to that described above. Tert-butyl (S)-(1-oxo-1-((phenylmethyl-$d_2$)amino)propan-2-yl)carbamate (7.01 g, 25 mmol, 1 eq) and 10 mL of TFA were used in the reaction. The compound was obtained as a colorless, clear oil.

Yield: 94% (4.2 g); TLC: $R_f$=0.21 (DCM:MeOH (9:0.5; v/v)); $C_{10}H_{12}D_2N_2O$ (180.25), Monoisotope mass: 181.12. UPLC (purity>99%): $t_R$=2.13 min. $(M+H)^+$ 181.2.

Example 29. Intermediate(S)-III (where B=D, X=D, Y=D); (S)-2-amino-N-((phenyl-$d_5$)methyl-$d_2$)propanamide The compound was obtained using an analogous procedure to that described above. Tert-butyl (S)-(1-oxo-1-(((phenyl-$d_5$)methyl-$d_2$)amino)propan-2-yl)carbamate (7.13 g, 25 mmol, 1 eq) and 10 mL of TFA were used in the reaction. The compound was obtained as a colorless, clear oil.

Yield: 91% (4.2 g); TLC: $R_f$=0.21 (DCM:MeOH (9:0.5; v/v)); $C_{10}H_7D_7N_2O$ (185.28), Monoisotope mass: 186.15. UPLC (purity>99%): $t_R$=2.14 min. $(M+H)^+$ 186.1.

Example 30. Intermediate(S)-III (where B=H, X=F, Y=D); (S)-2-amino-N-((2-fluorophenyl)methyl-$d_2$)propanamide The compound was obtained using an analogous procedure to that described above. Tert-butyl (S)-(1-(((2-fluorophenyl)methyl-$d_2$)amino)-1-oxopropan-2-yl)carbamate (6.86 g, 23 mmol, 1 eq) and 10 ml of TFA were used in the reaction. The compound was obtained as a colorless, clear oil.

Yield: 93% (4.2 g); TLC: $R_f$=0.23 (DCM:MeOH (9:0.5; v/v)); $C_{10}H_{11}D_2FN_2O$ (198.24), Monoisotopic mass: 199.11. UPLC (purity>99%): $t_R$=2.28 min. $(M+H)^+$ 199.2.

Example 31. Intermediate (R,S)-III (where B=H, X=H, Y=H); (R,S)-2-amino-N-benzylpropanamide The compound was obtained using an analogous procedure to that described above. Tert-butyl (R,S)-(1-(benzylamino)-1-oxopropan-2-yl)carbamate (6.50 g, 23 mmol, 1 eq) and 10 ml of TFA were used in the reaction. The compound was obtained as a colorless, clear oil.

Yield: 96% (3.9 g); TLC: $R_f$=0.21 (DCM:MeOH (9:0.5; v/v)); $C_{10}H_{14}N_2O$ (178.24), Monoisotopic mass: 179.11. UPLC (purity 98.2%): $t_R$=2.12 min. $(M+H)^+$ 179.3.

Example 32. Intermediate (R,S)-III (where B=D, X=D, Y=H); (R,S)-2-amino-N-((phenyl-$d_5$)methyl)propanamide The compound was obtained using an analogous procedure to that described above. Tert-butyl (R,S)-(1-oxo-1-(((phenyl-$d_5$)methyl)amino)propan-2-yl)carbamate (6.51 g, 23 mmol, 1 eq) and 10 ml of TFA were used in the reaction. The compound was obtained as a colorless, clear oil.

Yield: 93% (3.9 g); TLC: $R_f$=0.21 (DCM:MeOH (9:0.5; v/v)); $C_{10}H_9D_5N_2O$ (183.27), Monoisotope mass: 184.14. UPLC (purity 96.3%): $t_R$=2.14 min. $(M+H)^+$ 184.2.

Example 33. Intermediate (R,S)-III (where B=H, X=F, Y=H); (R,S)-2-amino-N-(2-fluorobenzyl)propanamide The compound was obtained using an analogous procedure to that described above. Tert-butyl (R,S)-(1-((2-fluorobenzyl)amino)-1-oxopropan-2-yl)carbamate (6.82 g, 23 mmol, 1 eq) and 10 ml of TFA were used in the reaction. The compound was obtained as a colorless, clear oil.

Yield: 94% (4.2 g); TLC: $R_f$=0.23 (DCM:MeOH (9:0.5; v/v)); $C_{10}H_{13}FN_2O$ (196.23), Monoisotopic mass: 197.10. UPLC (purity 98.2%): $t_R$=2.31 min. $(M+H)^+$ 197.1.

Example 34. Intermediate (R,S)-III (where B=H, X=H, Y=D); (R,S)-2-amino-N-(phenylmethyl-$d_2$) propanamide The compound was obtained using an analogous procedure to that described above. Tert-butyl (R,S)-(1-oxo-1-((phenylmethyl-$d_2$)amino)propan-2-yl)carbamate (7.01 g, 25 mmol, 1 eq) and 10 ml of TFA were used in the reaction. The compound was obtained as a colorless, clear oil.

Yield: 93% (4.2 g); TLC: $R_f$=0.21 (DCM:MeOH (9:0.5; v/v)); $C_{10}H_{12}D_2N_2O$ (180.25), Monoisotope mass: 181.12. UPLC (purity>99%): $t_R$=2.12 min. $(M+H)^+$ 181.2.

Example 35. Intermediate (R,S)-III (where B=D, X=D, Y=D); (R,S)-2-amino-N-((phenyl-$d_5$)methyl-$d_2$)propanamide The compound was obtained using an analogous procedure to that described above. Tert-butyl (R,S)-(1-oxo-1-(((phenyl-$d_5$)methyl-$d_2$)amino)propan-2-yl)carbamate (7.13 g, 25 mmol, 1 eq) and 10 mL of TFA were used in the reaction. The compound was obtained as a colorless, clear oil.

Yield: 94% (4.3 g); TLC: $R_f$=0.21 (DCM:MeOH (9:0.5; v/v)); $C_{10}H_7D_7N_2O$ (185.28), Monoisotope mass: 186.15. UPLC (purity>99%): $t_R$=2.14 min. $(M+H)^+$ 186.2.

Example 36. Intermediate (R,S)-III (where B=H, X=F, Y=D); (R,S)-2-amino-N-((2-fluorophenyl) methyl-$d_2$)propanamide The compound was obtained using an analogous procedure to that described above. Tert-butyl (R,S)-(1-(((2-fluorophenyl)methyl-$d_2$)amino)-1-oxopropan-2-yl)carbamate (6.86 g, 23 mmol, 1 eq) and 10 ml of TFA were used in the reaction. The compound was obtained as a colorless, clear oil.

Yield: 94% (4.3 g); TLC: $R_f$=0.23 (DCM:MeOH (9:0.5; v/v)); $C_{10}H_{11}D_2FN_2O$ (198.24), Monoisotopic mass: 199.11. UPLC (purity>99%): $t_R$=2.28 min. $(M+H)^+$ 199.2.

Example 37. Intermediate (R)-II (where, A=D, B=H, X=H, Y=H); (R)-4-((1-(benzylamino)-1-oxopropan-2-yl)amino)-4-oxobutanoic acid-2,2,3,3-$d_4$ Succinic anhydride-2,2,3,3-$d_4$ (2.18 g, 21 mmol, 1 eq) was added to a solution of (R)-2-amino-N-benzylpropanamide (3.9 g, 21 mmol, 1 eq) in ethyl acetate (50 mL), the mixture was stirred for 30 minutes. After this time, ethyl acetate was distilled off to dryness. The compound was obtained as a solid after washing with diethyl ether ($Et_2O$).

White solid. Yield: 94% (5.81 g); m.p. 129.5-131.6° C.; TLC: $R_f$=0.34 (DCM:MeOH (9:0.5; v/v)); $C_{14}H_{14}D_4N_2O_4$ (282.33), Monoisotope mass: 283.15. UPLC (purity 91.2%): $t_R$=3.12 min. $(M+H)^+$ 283.4.

Example 38. Intermediate (R)-II (where, A=H, B=D, X=D, Y=H); (R)-4-oxo-4-((1-oxo-1-(((phenyl-$d_5$)methyl)amino)propan-2-yl)amino)butanoic acid The compound was obtained using an analogous procedure to that described above. A solution of (R)-2-amino-N-((phenyl-$d_5$)methyl)propanamide (2.18 g, 12 mmol, 1 eq) in ethyl acetate (50 mL) and succinic anhydride (1.22 g, 12 mmol, 1 eq) were used in the reaction. The compound was obtained as a solid after washing with $Et_2O$.

White solid. Yield: 95% (3.20 g); m.p. 129.9-131.8° C.; TLC: $R_f$=0.35 (DCM:MeOH (9:0.5; v/v)); $C_{14}H_{13}D_5N_2O_4$ (283.34), Monoisotope mass: 284.15. UPLC (purity>99%): $t_R$=3.12 min. $(M+H)^+$ 284.1.

Example 39. Intermediate (R)-II (where, A=D, B=D, X=D, Y=H); (R)-4-oxo-4-((1-oxo-1-(((phenyl-$d_5$)methyl)amino)propan-2-yl)amino)butanoic acid-2,2,3,3-$d_4$ The compound was obtained using an analogous procedure to that described above. A solution of (R)-2-amino-N-((phenyl-$d_5$)methyl)propanamide (2.18 g, 12 mmol, 1 eq) in ethyl acetate (50 mL) and succinic anhydride-2,2,3,3-$d_4$ (1.26 g, 12 mmol, 1 eq) were used in the reaction. The compound was obtained as a solid after washing with $Et_2O$.

White solid. Yield: 96% (3.28 g); m.p. 129.7-131.3° C.; TLC: $R_f$=0.34 (DCM: MeOH (9:0.5; v/v)); $C_{14}H_9D_9N_2O_4$ (287.36), Monoisotope mass: 288.18. UPLC (purity>99%): $t_R$=3.12 min. $(M+H)^+$ 288.2.

Example 40. Intermediate (R)-II (where, A=D, B=H, X=F, Y=H); (R)-4-((1-((2-fluorobenzyl) amino)-1-oxopropan-2-yl)amino)-4-oxobutanoic acid-2,2,3,3-$d_4$ The compound was obtained using an analogous procedure to that described above. A solution of (R)-2-amino-N-(2-fluorobenzyl)propanamide (4.12 g, 21 mmol, 1 eq) in ethyl acetate (50 mL) and succinic anhydride-2,2,3,3-$d_4$ (2.18 g, 21 mmol, 1 eq) were used in the reaction. The compound was obtained as a solid after washing with $Et_2O$.

White solid. Yield: 95% (5.99 g); m.p. 131.2-132.6° C.; TLC: $R_f$=0.36 (DCM:MeOH (9:0.5; v/v)); $C_{14}H_{13}D_4FN_2O_4$ (300.32), Monoisotopic mass: 301.14. UPLC (purity 95.70%): $t_R$=3.32 min. $(M+H)^+$ 301.2.

Example 41. Intermediate (R)-II (where, A=D, B=H, X=H, Y=D); (R)-4-oxo-4-((1-oxo-1-((phenylmethyl-$d_2$)amino)propan-2-yl)amino)butanoic acid-2,2,3,3-$d_4$ The compound was obtained using an analogous procedure to that described above. A solution of (R)-2-amino-N-((phenyl-$d_2$)methyl)propanamide (2.16 g, 12 mmol, 1 eq) in ethyl acetate (50 mL) and succinic anhydride-2,2,3,3-$d_4$ (1.26 g, 12 mmol, 1 eq) were used in the reaction. The compound was obtained as a solid after washing with $Et_2O$.

White solid. Yield: 95% (3.23 g); m.p. 129.5-131.8° C.; TLC: $R_f$=0.34 (DCM:MeOH (9:0.5; v/v)); $C_{14}H_{12}D_6N_2O_4$ (284.34), Monoisotope mass: 285.16. UPLC (purity>99%): $t_R$=3.13 min. $(M+H)^+$ 285.2.

Example 42. Intermediate (R)-II (where A=D, B=D, X=D, Y=D); (R)-4-oxo-4-((1-oxo-1-(((phenyl-$d_5$)methyl-$d_2$)amino)propan-2-yl)amino)butanoic acid-2,2,3,3-$d_4$ The compound was obtained using an analogous procedure to that described above. A solution of (R)-2-amino-N-((phenyl-$d_5$) methyl-$d_2$)propanamide (2.22 g, 12 mmol, 1 eq) in ethyl acetate (50 mL) and succinic anhydride-2,2,3,3-$d_4$ (1.26 g, 12 mmol, 1 eq) were used in the reaction. The compound was obtained as a solid after washing with Et2O.

White solid. Yield: 94% (3.26 g); m.p. 129.1-131.2° C.; TLC: $R_f$=0.34 (DCM:MeOH (9:0.5; v/v)); $C_{14}H_7D_{11}N_2O_4$ (289.38), Monoisotope mass: 290.20. UPLC (purity>99%): $t_R$=3.12 min. $(M+H)^+$ 290.2.

Example 43. Intermediate (R)-II (where, A=D, B=H, X=F, Y=D); (R)-4-((1-(((2-fluorophenyl) methyl-$d_2$)amino)-1-oxopropan-2-yl)amino)-4-oxobutanoic acid-2,2,3,3-$d_4$ The compound was obtained using an analogous procedure to that described above. A solution of (R)-2-amino-N-((2-fluorophenyl)methyl-$d_2$)propanamide (2.37 g, 12 mmol, 1 eq) in ethyl acetate (50 mL) and succinic anhydride-2,2,3,3-$d_4$ (1.26 g, 12 mmol, 1 eq) were used in the reaction. The compound was obtained as a solid after washing with $Et_2O$.

White solid. Yield: 95% (3.44 g); m.p. 131.3-132.5° C.; TLC: $R_f$=0.36 (DCM:MeOH (9:0.5; v/v)); $C_{14}H_{11}D_6FN_2O_4$ (303.15), Monoisotope mass: 304.34. UPLC (purity>99%): $t_R$=3.34 min. $(M+H)^+$ 304.3.

Example 44. Intermediate(S)-II (where, A=D, B=H, X=H, Y=H); (S)-4-((1-(benzylamino)-1-oxopropan-2-yl)amino)-4-oxobutanoic acid-2,2,3,3-$d_4$ The compound was obtained using an analogous procedure to that described above. A solution of(S)-2-amino-N-benzylpropanamide (2.18 g, 12 mmol, 1 eq) in ethyl acetate (50 mL) and succinic anhydride-2,2,3,3-$d_4$ (1.26 g, 12 mmol, 1 eq) were used in the reaction. The compound was obtained as a solid after washing with $Et_2O$.

White solid. Yield: 92% (5.69 g); m.p. 129.3-131.9° C.; TLC: $R_f$=0.34 (DCM:MeOH (9:0.5; v/v)); $C_{14}H_{14}D_4N_2O_4$ (282.33), Monoisotope mass: 283.15. UPLC (purity 93.5%): $t_R$=3.13 min. $(M+H)^+$ 283.1.

Example 45. Intermediate(S)-II (where A=H, B=D, X=D, Y=H); (S)-4-oxo-4-((1-oxo-1-(((phenyl-$d_5$) methyl)amino)propan-2-yl)amino)butanoic acid The compound was obtained using an analogous procedure to that described above. A solution of(S)-2-amino-N-((phenyl-$d_5$)methyl)propanamide (2.18 g, 12 mmol, 1 eq) in ethyl acetate (50 mL) and succinic anhydride (1.22 g, 12 mmol, 1 eq) were used in the reaction. The compound was obtained as a solid after washing with $Et_2O$.

White solid. Yield: 96% (3.23 g); m.p. 129.5-131.4° C.; TLC: $R_f$=0.35 (DCM:MeOH (9:0.5; v/v)); $C_{14}H_{13}D_5N_2O_4$ (283.34), Monoisotope mass: 284.15. UPLC (purity>99%): $t_R$=3.11 min. $(M+H)^+$ 284.2.

Example 46. Intermediate(S)-II (where, A=D, B=D, X=D, Y=H); (S)-4-oxo-4-((1-oxo-1-(((phenyl-$d_5$) methyl)amino)propan-2-yl)amino)butanoic acid-2,2,3,3-$d_4$ The compound was obtained using an analogous procedure to that described above. A solution of(S)-2-amino-N-((phenyl-$d_5$)methyl)propanamide (2.18 g, 12 mmol, 1 eq) in ethyl acetate (50 mL) and succinic anhydride-2,2,3,3-$d_4$ were used in the reaction (1.22 g, 12 mmol, 1 eq). The compound was obtained as a solid after washing with $Et_2O$.

White solid. Yield: 95% (3.24 g); m.p. 129.5-131.2° C.; TLC: $R_f$=0.34 (DCM:MeOH (9:0.5; v/v)); $C_{14}H_9D_9N_2O_4$ (287.36), Monoisotope mass: 288.18. UPLC (purity>99%): $t_R$=3.11 min. $(M+H)^+$ 288.2.

Example 47. Intermediate(S)-II (where, A=D, B=H, X=F, Y=H); (S)-4-((1-((2-fluorobenzyl)amino)-1-oxopropan-2-yl)amino)-4-oxobutanoic acid-2,2,3,3-$d_4$ The compound was obtained using an analogous procedure to that described above. A solution of(S)-2-amino-N-(2-fluorobenzyl)propanamide (4.12 g, 21 mmol, 1 eq) in ethyl acetate (50 mL) and succinic anhydrid$_4$-2,2,3,3-$d_4$ (2.18 g, 21 mmol, 1 eq) were used in the reaction. The compound was obtained as a solid after washing with $Et_2O$.

White solid. Yield: 93% (5.86 g); m.p. 131.5-132.4° C.; TLC: $R_f$=0.36 (DCM:MeOH (9:0.5; v/v)); $C_{14}H_{13}D_4FN_2O_4$ (300.32), Monoisotopic mass: 301.14. UPLC (purity 99.20%): $t_R$=3.31 min. $(M+H)^+$ 301.2.

Example 48. Intermediate(S)-II (where, A=D, B=H, X=H, Y=D); (S)-4-oxo-4-((1-oxo-1-((phenylmethyl-$d_2$)amino)propan-2-yl)amino)butanoic acid-2,2,3,3-$d_4$ The compound was obtained using an analogous procedure to that described above. A solution of (S)-2-amino-N-((phenyl-$d_2$)methyl)propanamide (2.16 g, 12 mmol, 1 eq) in ethyl acetate (50 mL) and succinic anhydride-2,2,3,3-$d_4$ (1.26 g, 12 mmol, 1 eq) were used in the reaction. The compound was obtained as a solid after washing with $Et_2O$.

White solid. Yield: 96% (3.26 g); m.p. 129.5-131.7° C.; TLC: $R_f$=0.34 (DCM:MeOH (9:0.5; v/v)); $C_{14}H_{12}D_6N_2O_4$ (284.34), Monoisotope mass: 285.16. UPLC (purity>99%): $t_R$=3.12 min. $(M+H)^+$ 285.2.

Example 49. Intermediate(S)-II (where, A=D, B=D, X=D, Y=D); (S)-4-oxo-4-((1-oxo-1-(((phenyl-$d_5$) methyl-$d_2$)amino)propan-2-yl)amino)butanoic acid-2,2,3,3-$d_4$ The compound was obtained using an analogous procedure to that described above. A solution of(S)-2-amino-N-((phenyl-$d_5$)methyl-$d_2$)propanamide (2.22 g, 12 mmol, 1 eq) in ethyl acetate (50 mL) and succinic anhydride-2,2,3,3-$d_4$ (1.26 g 12 mmol, 1 eq) were used in the reaction. The compound was obtained as a solid after washing with $Et_2O$.

White solid. Yield: 93% (3.23 g); m.p. 129.1-131.4° C.; TLC: $R_f$=0.34 (DCM:MeOH (9:0.5; v/v)); $C_{14}H_7D_{11}N_2O_4$ (289.38), Monoisotope mass: 290.20. UPLC (purity>99%): $t_R$=3.13 min. $(M+H)^+$ 290.1.

Example 50. Intermediate(S)-II (where A=D, B=H, X=F, Y=D); (S)-4-((1-(((2-fluorophenyl)methyl-$d_2$) amino)-1-oxopropan-2-yl)amino)-4-oxobutanoic acid-2,2,3,3-$d_4$ The compound was obtained using an analogous procedure to that described above. A solution of (S)-2-amino-N-((2-fluorophenyl)methyl-$d_2$)propanamide (2.37 g, 12 mmol, 1 eq) in ethyl acetate (50 mL) and succinic anhydride-2,2,3,3-$d_4$ (1.26 g, 12 mmol, 1 eq) were used in the reaction. The compound was obtained as a solid after washing with $Et_2O$.

White solid. Yield: 94% (3.40 g); m.p. 131.2-132.4° C.; TLC: $R_f$=0.36 (DCM:MeOH (9:0.5; v/v)); $C_{14}H_{11}D_6FN_{204}$ (303.15), Monoisotope mass: 304.34. UPLC (purity>99%): $t_R$=3.35 min. $(M+H)^+$ 304.2.

Example 51. Intermediate (R,S)-II (where, A=D, B=H, X=H, Y=H); (R,S)-4-((1-(benzylamino)-1-oxopropan-2-yl)amino)-4-oxobutanoic acid-2,2,3,3-$d_4$ The compound was obtained using an analogous procedure to that described above. A solution of (R,S)-2-amino- N-benzylpropanamide (2.18 g, 12 mmol, 1 eq) in ethyl acetate (50 mL) and succinic anhydride-2,2,3,3-$d_4$ (1.26 g, 12 mmol, 1 eq) were used in the reaction. The compound was obtained as a solid after washing with $Et_2O$.

White solid. Yield: 95% (3.22 g); m.p. 89.3-90.9° C.; TLC: $R_f$=0.34 (DCM:MeOH (9:0.5; v/v)); $C_{14}H_{14}D_4N_2O_4$ (282.33), Monoisotope mass: 283.15. UPLC (purity>99%): $t_R$=3.12 min. $(M+H)^+$ 283.2.

Example 52. Intermediate (R,S)-II (where, A=H, B=D, X=D, Y=H); (R,S)-4-oxo-4-((1-oxo-1-(((phenyl-$d_5$)methyl)amino)propan-2-yl)amino)butanoic acid The compound was obtained using an analogous procedure to that described above. A solution of (R,S)-2-amino-N-((phenyl-$d_5$)methyl)propanamide (2.18 g, 12 mmol, 1 eq) in ethyl acetate (50 mL) and succinic anhydride (1.22 g, 12 mmol, 1 eq) were used in the reaction. The compound was obtained as a solid after washing with $Et_2O$.

White solid. Yield: 97% (3.26 g); m.p. 89.4-91.4° C.; TLC: $R_f$=0.35 (DCM: MeOH (9:0.5; v/v)); $C_{14}H_{13}D_5N_2O_4$ (283.34), Monoisotope mass: 284.15. UPLC (purity >99%): $t_R$=3.13 min. $(M+H)^+$ 284.2.

Example 53. Intermediate (R,S)-II (where, A=D, B=D, X=D, Y=H); (R,S)-4-oxo-4-((1-oxo-1-(((phenyl-$d_5$)methyl)amino)propan-2-yl)amino)butanoic acid-2,2,3,3-$d_4$ The compound was obtained using an analogous procedure to that described above. A solution of (R,S)-2-amino-N-((phenyl-$d_5$)methyl)propanamide (2.18 g, 12 mmol, 1 eq) in ethyl acetate (50 mL) and succinic anhydride-2,2,3,3-$d_4$ (1.26 g, 12 mmol, 1 eq) were used in the reaction. The compound was obtained as a solid after washing with $Et_2O$.

White solid. Yield: 92% (3.14 g); m.p. 89.1-90.6° C.; TLC: $R_f$=0.34 (DCM:MeOH (9:0.5; v/v)); $C_{14}H_9D_9N_2O_4$ (287.36), Monoisotope mass: 288.18. UPLC (purity>99%): $t_R$=3.12 min. $(M+H)^+$ 288.2.

Example 54. Intermediate (R,S)-II (where, A=D, B=H, X=F, Y=H); (R,S)-4-((1-((2-fluorobenzyl)amino)-1-oxopropan-2-yl)amino)-4-oxobutanoic acid-2,2,3,3-$d_4$ The compound was obtained using an analogous procedure to that described above. A solution of (R,S)-2-amino-N-(2-fluorobenzyl)propanamide (4.12 g, 21 mmol, 1 eq) in ethyl acetate (50 mL) and succinic anhydride-2,2,3,3-$d_4$ (2.18 g, 21 mmol, 1 eq) were used in the reaction. The compound was obtained as a solid after washing with $Et_2O$.

White solid. Yield: 93% (5.84 g); m.p. 89.3-90.5° C.; TLC: $R_f$=0.36 (DCM:MeOH (9:0.5; v/v)); $C_{14}H_{13}D_4FN_2O_4$ (300.32), Monoisotopic mass: 301.14. UPLC (purity>99%): $t_R$=3.32 min. $(M+H)^+$ 301.2.

Example 55. Intermediate (R,S)-II (where, A=D, B=H, X=H, Y=D); (R,S)-4-oxo-4-((1-oxo-1-((phenylmethyl-$d_2$)amino)propan-2-yl)amino)butanoic acid-2,2,3,3-$d_4$ The compound was obtained using an analogous procedure to that described above. A solution of (R,S)-2-amino-N-((phenyl-$d_2$)methyl)propanamide (2.16 g, 12 mmol, 1 eq) in ethyl acetate (50 mL) and succinic anhydride-2,2,3,3-$d_4$ (1.26 g, 12 mmol, 1 eq) were used in the reaction. The compound was obtained as a solid after washing with $Et_2O$.

White solid. Yield: 94% (3.19 g); m.p. 89.1-90.6° C.; TLC: $R_f$=0.34 (DCM:MeOH (9:0.5; v/v)); $C_{14}H_{12}D_6N_2O_4$ (284.34), Monoisotope mass: 285.16. UPLC (purity>99%): $t_R$=3.12 min. $(M+H)^+$ 285.1.

Example 56. Intermediate (R,S)-II (where, A=D, B=D, X=D, Y=D); (R,S)-4-oxo-4-((1-oxo-1-(((phenyl-$d_5$)methyl-$d_2$)amino)propan-2-yl)amino)butanoic acid-2,2,3,3-$d_4$ The compound was obtained using an analogous procedure to that described above. A solution of (R,S)-2-amino-N-((phenyl-$d_5$)methyl-$d_2$)propanamide (2.22 g, 12 mmol, 1 eq) in ethyl acetate (50 mL) and succinic anhydride-2,2,3,3-$d_4$ (1.26 g, 12 mmol, 1 eq) were used in the reaction. The compound was obtained as a solid after washing with $Et_2O$.

White solid. Yield: 95% (3.29 g); m.p. 89.4-90.7° C.; TLC: $R_f$=0.34 (DCM:MeOH (9:0.5; v/v)); $C_{14}H_7D_{11}N_2O_4$ (289.38), Monoisotope mass: 290.20. UPLC (purity>99%): $t_R$=3.13 min. $(M+H)^+$ 290.3.

Example 57. Intermediate (R,S)-II (where, A=D, B=H, X=F, Y=D); (R,S)-4-((1-(((2-fluorophenyl)methyl-$d_2$)amino)-1-oxopropan-2-yl)amino)-4-oxobutanoic acid-2,2,3,3-$d_4$ The compound was obtained using an analogous procedure to that described above. A solution of (R,S)-2-amino-N-((2-fluorophenyl)methyl-$d_2$)propanamide (2.37 g, 12 mmol, 1 eq) in ethyl acetate (50 mL) and succinic anhydrid$_4$-2,2,3,3-$d_4$ (1.26 g, 12 mmol, 1 eq) were used in the reaction. The compound was obtained as a solid after washing with $Et_2O$.

White solid. Yield: 96% (3.47 g); m.p. 89.4-90.6° C.; TLC: $R_f$=0.36 (DCM:MeOH (9:0.5; v/v)); $C_{14}H_{11}D_6FN_2O_4$ (303.15), Monoisotope mass: 304.34. UPLC (purity>99%): $t_R$=3.33 min. $(M+H)^+$ 304.2.

Examples of Synthesis and Physicochemical and Spectral Data of the Final Products According to the Formula (I):

Example 58. Compound $d_4$-(R)-1 (where, A=D, B=H, X=H, Y=H); (R)—N-benzyl-2-(2,5-dioxopyrrolidin-1-yl-3,3,4,4-$d_4$)propanamide $ZnCl_2$ (1.36 g, 10 mmol, 1 eq) was added to a suspension of (R)-4-((1-(benzylamino)-1-oxopropan-2-yl)amino)-4-oxobutanoic acid-2,2,3,3-$d_4$ (2.82 g, 10 mmol, 1 eq) in anhydrous 1,4-dioxane (100 mL), the whole mixture was heated to 110° C. A solution of HMDS (2.42 g, 3.14 mL, 15 mmol, 1.5 eq) in anhydrous 1,4-dioxane (15 mL) was then added dropwise over 30 minutes. The reaction was continued with stirring at reflux for about 24 hours, then concentrated under reduced pressure. After distilling off the solvent, the oily residue was dissolved in DCM and extracted with 0.1 M HCl (3×50 mL), water (3×50 mL) and saturated NaCl solution (3×50 mL). The organic layer was dried over anhydrous $Na_2SO_4$ and then evaporated to dryness. The crude product was purified by column chromatography with DCM:MeOH (9:0.3; v/v) eluents system. The compound was obtained as a solid after washing with $Et_2O$.

White solid. Yield: 89% (2.34 g); m.p. 138.2-138.9° C.; TLC: $R_f$=0.39 (DCM:MeOH (9:0.3; v/v)); $C_{14}H_{12}D_4N_2O_3$ (264.32), Monoisotopic mass: 265.14. UPLC (purity>99%): $t_R$=3.79 min. $(M+H)^+$ 265.2. Chiral HPLC>99% ee ($t_R$=24.566 min). $^1H$ NMR (500 MHz, $CDCl_3$) δ 1.57 (d, J=7.2 Hz, 3H), 4.39 (d, J=5.7 Hz, 2H), 4.77 (q, J=7.2 Hz, 1H), 6.40 (br s, 1H), 7.22-7.26 (m, 3H), 7.29-7.32 (m, 2H). $^{13}$C NMR (126 MHz, $CDCl_3$) δ 14.5, 28.3, 33.7, 49.8, 127.7, 128.8, 137.9, 168.6, 177.0.

Example 59. Compound $d_4$-(S)-1 (where, A=D, B=H, X=H, Y=H); (S)—N-benzyl-2-(2,5-dioxopyrrolidin-1-yl-3,3,4,4-$d_4$)propanamide The compound was obtained using an analogous procedure to that described above. (S)-4-((1-(benzylamino)-1-oxopropan-2-yl)amino)-4-oxobutanoic acid-2,2,3,3-$d_4$ (2.87 g, 10 mmol, 1 eq) and $ZnCl_2$ (1.36 g, 20 mmol, 1 eq), and HMDS (2.42 g, 3.14 mL, 15 mmol, 1.5 eq) were used in the reaction. The crude product was purified by column chromatography with DCM:MeOH (9:0.3; v/v) eluents system. The compound was obtained as a solid after washing with $Et_2O$.

White solid. Yield: 87% (2.29 g); m.p. 137.9-138.8° C.; TLC: $R_f$=0.39 (DCM:MeOH (9:0.3; v/v)); $C_{14}H_{12}D_4N_2O_3$ (264.32), Monoisotopic mass: 265.14. UPLC (purity>99%): $t_R$=3.76 min. $(M+H)^+$ 265.3. Chiral HPLC>99% ee ($t_R$=26.484 min). $^1$H NMR (500 MHz, $CDCl_3$) δ 1.59 (d, J=7.5 Hz, 3H), 4.43 (d, J=5.7 Hz, 2H), 4.79 (q, J=7.4 Hz, 1H), 6.33 (br s, 1H), 7.24-7.28 (m, 3H), 7.31 (d, J=6.9 Hz, 2H). $^{13}$C NMR (126 MHz, $CDCl_3$) δ 14.5, 25.7, 34.0, 49.8, 127.7, 128.8, 137.9, 168.6, 177.0.

Example 60. Compound $d_4$-(R,S)-1 (where, A=D, B=H, X=H, Y=H); (R,S)—N-benzyl-2-(2,5-dioxopyrrolidin-1-yl-3,3,4,4-$d_4$)propanamide The compound was obtained using an analogous procedure to that described above. (R,S)-4-((1-(benzylamino)-1-oxopropan-2-yl)amino)-4-oxobutanoic acid-2,2,3,3-$d_4$ (2.87 g, 10 mmol, 1 eq) and $ZnCl_2$ (1.36 g, 20 mmol, 1 eq), and HMDS (2.42 g, 3.14 mL, 15 mmol, 1.5 eq) were used in the reaction. The crude product was purified by column chromatography with DCM:MeOH (9:0.3; v/v) eluents system. The compound was obtained as a solid after washing with $Et_2O$.

White solid. Yield: 85% (2.23 g); mp 83.4-84.2° C.; TLC: $R_f$=0.39 (DCM:MeOH (9:0.3; v/v)); $C_{14}H_{12}D_4N_2O_3$ (264.32), Monoisotopic mass: 265.14. UPLC (purity>99%): $t_R$=3.78 min. $(M+H)^+$ 265.2. $^1$H NMR (500 MHz, $CDCl_3$) δ 1.55-1.59 (m, 3H), 4.40 (d, J=5.4 Hz, 2H), 4.76 (qd, J=7.4, 1.7 Hz, 1H), 6.41 (br s, 1H), 7.22-7.27 (m, 3H), 7.29-7.33 (m, 2H). $^{13}$C NMR (126 MHz, $CDCl_3$) δ 14.5, 25.7, 34.0, 49.8, 129.4, 129.4, 130.2, 130.2, 168.8, 177.0.

Example 61. Compound $d_9$-(R)-2 (where, A=D, B=D, X=D, Y=H); (2R)-2-(2,5-dioxopyrrolidin-1-yl-3,3,4,4-$d_4$)-N-((phenyl-$d_5$)methyl)propanamide The compound was obtained using an analogous procedure to that described above. (R)-4-oxo-4-((1-oxo-1-(((phenyl-$d_5$)methyl)amino)propan-2-yl)amino)butanoic acid-2,2,3,3-$d_4$ (2.87 g, 10 mmol, 1 eq) and $ZnCl_2$ (1.36 g, 20 mmol, 1 eq), and HMDS (2.42 g, 3.14 mL, 15 mmol, 1.5 eq) were used in the reaction. The crude product was purified by column chromatography with DCM:MeOH (9:0.3; v/v) eluents system. The compound was obtained as a solid after washing with $Et_2O$.

White solid. Yield: 85% (2.29 g); m.p. 139.3-140.7° C.; TLC: $R_f$=0.44 (DCM:MeOH (9:0.3; v/v)); $C_{14}H_7D_9N_2O_3$ (269.35), Monoisotopic mass: 270.17. UPLC (purity>99%): $t_R$=3.82 min, $(M+H)^+$ 270.1. Chiral HPLC>99% ee ($t_R$=24.539 min). $^1$H NMR (500 MHz, $CDCl_3$) δ 1.58 (d, J=7.2 Hz, 3H), 4.43 (d, J=5.7 Hz, 2H), 4.79 (q, J=7.2 Hz, 1H), 6.31 (br s, 1H). $^{13}$C NMR (126 MHz, $CDCl_3$) δ 14.6, 34.0, 43.8, 49.9, 127.1, 127.3, 128.3, 137.7, 168.6, 176.9.

Example 62. Compound $d_9$-(S)-2 (where A=D, B=D, X=D, Y=H); (2S)-2-(2,5-dioxopyrrolidin-1-yl-3,3,4,4-$d_4$)-N-((phenyl-$d_5$)methyl)propanamide The compound was obtained using an analogous procedure to that described above. (S)-4-oxo-4-((1-oxo-1-(((phenyl-$d_5$)methyl)amino)propan-2-yl)amino)butanoic acid-2,2,3,3-$d_4$ (2.87 g, 10 mmol, 1 eq) and $ZnCl_2$ (1.36 g, 20 mmol, 1 eq), and HMDS (2.42 g, 3.14 mL, 15 mmol, 1.5 eq) were used in the reaction. The crude product was purified by column chromatography with DCM:MeOH (9:0.3; v/v) eluents system. The compound was obtained as a solid after washing with $Et_2O$.

White solid. Yield: 84% (2.26 g); m.p. 138.9-140.2° C.; TLC: $R_f$=0.44 (DCM:MeOH (9:0.3; v/v)); $C_{14}H_7D_9N_2O_3$ (269.35), Monoisotopic mass: 270.17. UPLC (purity>99%): $t_R$=3.81 min, $(M+H)^+$ 270.2. Chiral HPLC>99% ee ($t_R$=26.476 min). $^1$H NMR (500 MHz, $CDCl_3$) δ 1.57 (d, J=7.2 Hz, 3H), 4.40 (d, J=5.7 Hz, 2H), 4.77 (q, J=7.5 Hz, 1H), 6.42 (br s, 1H). $^{13}$C NMR (126 MHz, $CDCl_3$) δ 14.5, 34.0, 43.8, 49.8, 127.3, 128.1, 128.3, 137.7, 168.7, 177.0.

Example 63. Compound $d_9$-(R,S)-2 (where, A=D, B=D, X=D, Y=H); (2R,S)-2-(2,5-dioxopyrrolidin-1-yl-3,3,4,4-$d_4$)-N-((phenyl-$d_5$)methyl)propanamide The compound was obtained using an analogous procedure to that described above. (R,S)-4-oxo-4-((1-oxo-1-(((phenyl-$d_5$)methyl)amino)propan-2-yl)amino)butanoic acid-2,2,3,3-$d_4$ (2.87 g, 10 mmol, 1 eq) and $ZnCl_2$ (1.36 g, 20 mmol, 1 eq), and HMDS (2.42 g, 3.14 mL, 15 mmol, 1.5 eq) were used in the reaction. The crude product was purified by column chromatography with DCM:MeOH (9:0.3; v/v) eluents system. The compound was obtained as a solid after washing with $Et_2O$.

White solid. Yield: 87% (2.34 g); m.p. 84.1-85.5° C.; TLC: $R_f$=0.4 (DCM:MeOH (9:0.3; v/v)); $C_{14}H_7D_9N_2O_3$ (269.35), Monoisotopic mass: 270.17. UPLC (purity>99%): $t_R$=3.80 min, $(M+H)^+$ 270.1. $^1$H NMR (500 MHz, $CDCl_3$) δ 1.57 (d, J=7.2 Hz, 3H), 4.40 (d, J=5.7 Hz, 2H), 4.77 (q, J=7.2 Hz, 1H), 6.40 (br s, 1H). $^{13}$C NMR (126 MHz, $CDCl_3$) δ 14.5, 34.0, 43.8, 49.8, 127.1, 127.3, 128.1, 137.7, 168.6, 177.0.

Example 64. Compound $d_5$-(R)-3 (where, A=H, B=D, X=D, Y=H); (2R)-2-(2,5-dioxopyrrolidin-1-yl)-N-((phenyl-$d_5$)methyl)propanamide The compound was obtained using an analogous procedure to that described above. (R)-4-oxo-4-((1-oxo-1-(((phenyl-$d_5$)methyl)amino)propan-2-yl)amino)butanoic acid (2.83 g, 10 mmol, 1 eq) and $ZnCl_2$ (1.36 g, 10 mmol, 1 eq), and HMDS (2.42 g, 3.14 mL, 15 mmol, 1.5 eq) were used in the reaction. The crude product was purified by column chromatography with DCM:MeOH (9:0.3; v/v) eluents system. The compound was obtained as a solid after washing with $Et_2O$.

White solid. Yield: 87% (2.30 g); m.p. 138.9-140.2° C.; TLC: $R_f$=0.43 (DCM:MeOH (9:0.3; v/v)); $C_{14}H_{11}D_5N_2O_3$ (265.32), Monoisotopic mass: 266.15. UPLC (purity>99%): $t_R$=3.80 min, $(M+H)^+$ 266.2. Chiral HPLC>99% ee ($t_R$=24.447 min). $^1$H NMR (500 MHz, $CDCl_3$) δ 1.58 (d, J=7.2 Hz, 3H), 2.67-2.71 (m, 4H), 4.42 (d, J=5.4 Hz, 2H), 4.76-4.79 (m, 1H), 6.37 (br s, 1H). $^{13}$C NMR (126 MHz, $CDCl_3$) δ 14.6, 34.0, 43.8, 49.9, 127.1, 127.3, 128.3, 137.7, 168.6, 176.9.

Example 65. Compound $d_5$-(S)-3 (where, A=H, B=D, X=D, Y=H); (2S)-2-(2,5-dioxopyrrolidin-1-yl)-N-((phenyl-$d_5$)methyl)propanamide The compound was obtained using an analogous procedure to that described above. (S)-4-oxo-4-((1-oxo-1-(((phenyl-$d_5$)methyl)amino)propan-2-yl)amino)butanoic acid (2.83 g, 10 mmol, 1 eq) and $ZnCl_2$ (1.36 g, 10 mmol, 1 eq), and HMDS (2.42 g, 3.14 mL, 15 mmol, 1.5 eq) were used in the reaction. The crude product was purified by column chromatography with DCM:MeOH (9:0.3; v/v) eluents system. The compound was obtained as a solid after washing with $Et_2O$.

White solid. Yield: 85% (2.25 g); m.p. 138.4-139.8° C.; TLC: $R_f$=0.43 (DCM:MeOH (9:0.3; v/v)); $C_{14}H_{11}D_5N_2O_3$ (265.32), Monoisotopic mass: 266.15. UPLC (purity>99%): $t_R$=3.81 min, $(M+H)^+$ 266.2. Chiral HPLC>99% ee ($t_R$=26.484 min). $^1$H NMR (500 MHz, $CDCl_3$) δ 1.58 (d, J=7.2 Hz, 3H), 2.69 (s, 4H), 4.42 (d, J=5.7 Hz, 2H), 4.79 (q, J=7.5 Hz, 1H), 6.38 (br s, 1H). $^{13}$C NMR (126 MHz, $CDCl_3$) δ 14.5, 28.3, 34.0, 43.9, 49.8, 127.1, 128.1, 137.7, 168.7, 175.6.

Example 66. Compound $d_5$-(R,S)-3 (where, A=H, B=D, X=D, Y=H); (2R,S)-2-(2,5-dioxopyrrolidin-1-yl)-N-((phenyl-$d_5$)methyl)propanamide The compound was obtained using an analogous procedure to that described above. (R,S)-4-oxo-4-((1-oxo-1-(((phenyl-$d_5$)methyl)amino)propan-2-yl)amino)butanoic acid (2.83 g, 10 mmol, 1 eq) and $ZnCl_2$ (1.36 g, 10 mmol, 1 eq), and HMDS (2.42 g, 3.14 mL, 15 mmol, 1.5 eq) were used in the reaction. The crude product was purified by column chromatography with DCM:MeOH (9:0.3; v/v) eluents system. The compound was obtained as a solid after washing with $Et_2O$.

White solid. Yield: 84% (2.22 g); m.p. 84.4-86.1° C.; TLC: $R_f$=0.43 (DCM:MeOH (9:0.3; v/v)); $C_{14}H_{11}D_5N_2O_3$ (265.32), Monoisotopic mass: 266.15. UPLC (purity>99%): $t_R$=3.82 min, $(M+H)^+$ 266.2. $^1$H NMR (500 MHz, $CDCl_3$) δ 1.57 (d, J=7.5 Hz, 3H), 2.68 (s, 4H), 4.40 (d, J=5.7 Hz, 2H), 4.77 (q, J=7.2 Hz, 1H), 6.42 (br s, 1H). $^{13}$C NMR (126 MHz, $CDCl_3$) δ 14.5, 28.3, 33.9, 43.8, 49.8, 127.1, 128.1, 137.7, 168.7, 177.0.

Example 67. Compound $d_4$-(R)-4 (where, A=D, B=H, X=F, Y=H); (R)—N-(2-fluorobenzyl)-2-(2,5-dioxopyrrolidin-1-yl-3,3,4,4-$d_4$)propanamide The compound was obtained using an analogous procedure to that described above. (R)-4-((1-((2-fluorobenzyl)amino)-1-oxopropan-2-yl)amino)-4-oxobutanoic acid-2,2,3,3-$d_4$ (3.00 g, 10 mmol, 1 eq) and $ZnCl_2$ (1.36 g, 20 mmol, 1 eq), and HMDS (2.42 g, 3.14 mL, 15 mmol, 1.5 eq) were used in the reaction. The crude product was purified by column chromatography with DCM:MeOH (9:0.3; v/v) eluents system. The compound was obtained as a solid after washing with $Et_2O$.

White solid. Yield: 84% (2.36 g); m.p. 157.2-157.3° C.; TLC: $R_f$=0.44 (DCM:MeOH (9:0.3; v/v)); $C_{14}H_{11}D_4FN_2O_3$ (282.31), Monoisotopic mass: 283.13. UPLC (purity>99%): $t_R$=4.01 min, $(M+H)^+$ 283.2. Chiral HPLC>99% ee ($t_R$=18.863 min). $^1$H NMR (500 MHz, $CDCl_3$) δ 1.57 (d, J=7.3 Hz, 3H), 4.38-4.52 (m, 2H), 4.76 (q, J=7.3 Hz, 1H), 6.48 (br s, 1H), 6.98-7.04 (m, 1H), 7.08-7.11 (m, 1H), 7.20-7.24 (1H), 7.30-7.31 (m, 1H). $^{13}$C NMR (126 MHz, $CDCl_3$) δ 14.5, 37.9, 38.0, 49.8 115.4, 124.5 (J=3.6 Hz), 124.8, 124.9, 129, 4 (J=8.5 Hz), 130.2 (J=4.2 Hz), 168.7, 177.0.

Example 68. Compound $d_4$-(S)-4 (where, A=D, B=H, X=F, Y=H); (S)—N-(2-fluorobenzyl)-2-(2,5-dioxopyrrolidin-1-yl-3,3,4,4-$d_4$)propanamide The compound was obtained using an analogous procedure to that described above. (S)-4-((1-((2-fluorobenzyl)amino)-1-oxopropan-2-yl)amino)-4-oxobutanoic acid-2,2,3,3-$d_4$ (3.00 g, 10 mmol, 1 eq) and $ZnCl_2$ (1.36 g, 20 mmol, 1 eq), and HMDS (2.42 g, 3.14 mL, 15 mmol, 1.5 eq) were used in the reaction. The crude product was purified by column chromatography with DCM:MeOH (9:0.3; v/v) eluents system. The compound was obtained as a solid after washing with $Et_2O$.

White solid. Yield: 86% (2.41 g); m.p. 157.4-157.8° C.; TLC: $R_f$=0.44 (DCM:MeOH (9:0.3; v/v)); $C_{14}H_{11}D_4FN_2O_3$ (282.31), Monoisotopic mass: 283.13. UPLC (purity>99%): $t_R$=3.90 min, $(M+H)^+$ 283.3. Chiral HPLC>99% ee ($t_R$=21.383 min). $^1$H NMR (500 MHz, $CDCl_3$) δ 1.57 (d, J=7.5 Hz, 3H), 4.40-4.51 (m, 2H), 4.77 (q, J=7.5 Hz, 1H), 6.49 (br s, 1H), 7.01 (t, J=9.3 Hz, 1H), 7.09 (td, J=7.5, 0.9 Hz, 1H), 7.21-7.25 (m, 1H), 7.31 (td, J=7.6, 1.4 Hz, 1H). $^{13}$C NMR (126 MHz, $CDCl_3$) δ 14.5, 37.9 (d, J=4.2 Hz), 49.8, 115.5, 124.5 (d, J=3.6 Hz), 124.8, 124.9, 129.4 (d, J=7.8 Hz), 130.2 (d, J=3.6 Hz), 168.7, 176.9.

Example 69. Compound $d_4$-(R,S)-4 (where, A=D, B=H, X=F, Y=H); (R,S)—N-(2-fluorobenzyl)-2-(2,5-dioxopyrrolidin-1-yl-3,3,4,4-$d_4$)propanamide The compound was obtained using an analogous procedure to that described above. (R,S)-4-((1-((2-fluorobenzyl)amino)-1-oxopropan-2-yl)amino)-4-oxobutanoic acid-2,2,3,3-$d_4$ (3.00 g, 10 mmol, 1 eq) and $ZnCl_2$ (1.36 g, 20 mmol, 1 eq), and HMDS (2.42 g, 3.14 mL, 15 mmol, 1.5 eq) were used in the reaction. The crude product was purified by column chromatography with DCM:MeOH (9:0.3; v/v) eluents system. The compound was obtained as a solid after washing with $Et_2O$.

White solid. Yield: 85% (2.38 g); m.p. 98.4-99.7° C.; TLC: $R_f$=0.44 (DCM:MeOH (9:0.3; v/v)); $C_{14}H_{11}D_4FN_2O_3$ (282.31), Monoisotopic mass: 283.13. UPLC (purity>99%): $t_R$=3.95 min, $(M+H)^+$ 283.2. $^1$H NMR (500 MHz, $CDCl_3$) δ 1.57 (d, J=7.5 Hz, 3H), 4.40-4.50 (m, 2H), 4.76 (q, J=7.2 Hz, 1H), 6.52 (br s, 1H), 6.98-7.03 (m, 1H), 7.08 (td, J=7.5, 1.0 Hz, 1H), 7.20-7.24 (m, 1H), 7.30 (td, J=7.6, 1.7 Hz, 1H). $^{13}$C NMR (126 MHz, $CDCl_3$) δ 14.5, 34.0, 37.9 (d, J=3.6 Hz), 49.8, 115.5, 124.5 (d, J=3.6 Hz), 129.4 (d, J=8.5 Hz), 130.2 (d, J=4.2 Hz), 168.8, 177.0.

Example 70. Compound $d_6$-(R)-5 (where, A=D, B=H, X=H, Y=D); (R)-2-(2,5-dioxopyrrolidin-1-yl-3,3,4,4-$d_4$)-N-(phenylmethyl-$d_2$)propanamide The compound was obtained using an analogous procedure to that described above. (R)-4-oxo-4-((1-oxo-1-((phenylmethyl-$d_2$)amino)propan-2-yl)amino)butanoic acid-2,2,3,3-$d_4$ (2.84 g, 10 mmol, 1 eq) and $ZnCl_2$ (1.36 g, 20 mmol, 1 eq), and HMDS (2.42 g, 3.14 mL, 15 mmol, 1.5 eq) were used in the reaction. The crude product was purified by column chromatography with DCM:MeOH (9:0.3; v/v) eluents system. The compound was obtained as a solid after washing with $Et_2O$.

White solid. Yield: 86% (2.28 g); m.p. 138.3-139.1° C.; TLC: $R_f$=0.39 (DCM:MeOH (9:0.3; v/v)); $C_{14}H_{10}D_6N_2O_3$ (266.33), Monoisotopic mass: 267.15. UPLC (purity>99%): $t_R$=3.78 min $(M+H)^+$ 267.2. Chiral HPLC>99% ee ($t_R$=23.945 min). $^1$H NMR (500 MHz, $CDCl_3$) δ 1.58 (d, J=7.5 Hz, 3H), 4.78 (q, J=7.5 Hz, 1H), 6.35 (br s, 1H), 7.22-7.28 (m, 3H), 7.30-7.33 (m, 2H). $^{13}$C NMR (126 MHz, $CDCl_3$) δ 14.6, 25.7, 34.0, 49.8, 127.8, 128.8, 137.8, 168.6, 177.0.

Example 71. Compound $d_6$-(S)-5 (where, A=D, B=H, X=H, Y=D); (S)-2-(2,5-dioxopyrrolidin-1-yl-3,3,4,4-$d_4$)-N-(phenylmethyl-$d_2$)propanamide The compound was obtained using an analogous procedure to that described above. (S)-4-oxo-4-((1-oxo-1-((phenylmethyl-$d_2$)amino)propan-2-yl)amino)butanoic acid-2,2,3,3-$d_4$ (2.84 g, 10 mmol, 1 eq) and $ZnCl_2$ (1.36 g, 20 mmol, 1 eq), and HMDS (2.42 g, 3.14 mL, 15 mmol, 1.5 eq) were used in the reaction. The crude product was purified by column chromatography with DCM:MeOH (9:0.3; v/v) eluents system. The compound was obtained as a solid after washing with $Et_2O$.

White solid. Yield: 84% (2.23 g); m.p. 138.3-139.0° C.; TLC: $R_f$=0.39 (DCM:MeOH (9:0.3; v/v)); $C_{14}H_{10}D_6N_2O_3$ (266.33), Monoisotopic mass: 267.15. UPLC (purity>99%): $t_R$=3.78 min $(M+H)^+$ 267.2. Chiral HPLC>99% ee ($t_R$=25.872 min). $^1$H NMR (500 MHz, $CDCl_3$) δ 1.58 (d, J=7.5 Hz, 3H), 4.78 (q, J=7.5 Hz, 1H), 6.35 (br s, 1H), 7.23-7.28 (m, 3H), 7.30-7.34 (m, 2H). $^{13}$C NMR (126 MHz, $CDCl_3$) δ 14.6, 25.7, 34.0, 49.8, 127.8, 128.8, 137.8, 168.6, 177.0.

Example 72. Compound $d_6$-(R,S)-5 (where, A=D, B=H, X=H, Y=D); (R,S)-2-(2,5-dioxopyrrolidin-1-yl-3,3,4,4-$d_4$)-N-(phenylmethyl-$d_2$)propanamide The compound was obtained using an analogous procedure to that described above. (R,S)-4-oxo-4-((1-oxo-1-((phenylmethyl-$d_2$)amino)propan-2-yl)amino)butanoic acid-2,2,3,3-$d_4$ (2.84 g, 10 mmol, 1 eq) and $ZnCl_2$ (1.36 g, 20 mmol, 1 eq), and HMDS (2.42 g, 3.14 mL, 15 mmol, 1.5 eq) were used in the reaction. The crude product was purified by column chromatography with DCM:MeOH (9:0.3; v/v) eluents system. The compound was obtained as a solid after washing with $Et_2O$.

White solid. Yield: 82% (2.18 g); m.p. 84.5-86.2° C.; TLC: $R_f$=0.39 (DCM:MeOH (9:0.3; v/v)); $C_{14}H_{10}D_6N_2O_3$ (266.33), Monoisotopic mass: 267.15. UPLC (purity>99%): $t_R$=3.78 min $(M+H)^+$ 267.3. $^1$H NMR (500 MHz, $CDCl_3$) δ 1.58 (d, J=7.2 Hz, 3H), 4.77 (q, J=7.5 Hz, 1H), 6.35 (br s, 1H), 7.23-7.27 (m, 3H), 7.30-7.33 (m, 2H). $^{13}$C NMR (126 MHz, $CDCl_3$) δ 14.5, 25.7, 34.0, 49.8, 127.5, 128.5, 137.7, 168.6, 177.0.

Example 73. Compound $d_6$-(R)-7 (where, A=D, B=H, X=F, Y=D); (R)-2-(2,5-dioxopyrrolidin-1-yl-3,3,4,4-$d_4$)-N-((2-fluorophenyl)methyl-$d_2$)propanamide The compound was obtained using an analogous procedure to that described above. (R)-4-((1-(((2-fluorophenyl)methyl-$d_2$)amino)-1-oxopropan-2-yl)amino)-4-oxobutanoic acid-2,2,3,3-$d_4$ (3.03 g, 10 mmol, 1 eq) and $ZnCl_2$ (1.36 g, 20 mmol, 1 eq), and HMDS (2.42 g, 3.14 mL, 15 mmol, 1.5 eq) were used in the reaction. The crude product was purified by column chromatography with DCM:MeOH (9:0.3; v/v) eluents system. The compound was obtained as a solid after washing with $Et_2O$.

White solid. Yield: 84% (2.39 g); m.p. 157.2-157.7° C.; TLC: $R_f$=0.44 (DCM:MeOH (9:0.3; v/v)); $C_{14}H_9D_6FN_2O_3$ (284.32), Monoisotope mass: 284.14. UPLC (purity>99%): $t_R$=3.98 min $(M+H)^+$ 285.2. Chiral HPLC>99% ee ($t_R$=18.011 min). $^1$H NMR (500 MHz, $CDCl_3$) δ 1.57 (d, J=7.2 Hz, 3H), 4.76 (q, J=7.3 Hz, 1H), 6.44 (br s, 1H) 7.01 (ddd, J=10.2, 8.2, 1.0 Hz, 1H), 7.09 (td, J=7.6, 1.2 Hz, 1H), 7.21-7.26 (m, 1H), 7.31 (td, J=7.6, 1.7 Hz, 1H). $^{13}$C NMR (126 MHz, $CDCl_3$) δ 14.5, 25.7, 34.0, 49.8, 115.5, 124.5 (d, J=3.6 Hz), 129.4 (d, J=8.5 Hz), 130.2 (d, J=4.2 Hz), 168.8, 177.0.

Example 74. Compound $d_6$-(S)-7 (where, A=D, B=H, X=F, Y=D); (S)-2-(2,5-dioxopyrrolidin-1-yl-3,3,4,4-$d_4$)-N-((2-fluorophenyl)methyl-$d_2$)propanamide The compound was obtained using an analogous procedure to that described above. (S)-4-((1-(((2-fluorophenyl)methyl-$d_2$)amino)-1-oxopropan-2-yl)amino)-4-oxobutanoic acid-2,2,3,3-$d_4$ (3.03 g, 10 mmol, 1 eq) and $ZnCl_2$ (1.36 g, 20 mmol, 1 eq), and HMDS (2.42 g, 3.14 mL, 15 mmol, 1.5 eq) were used in the reaction. The crude product was purified by column chromatography with DCM:MeOH (9:0.3; v/v) eluents system. The compound was obtained as a solid after washing with $Et_2O$.

White solid. Yield: 86% (2.44 g); m.p. 157.3-157.7° C.; TLC: $R_f$=0.44 (DCM:MeOH (9:0.3; v/v)); $C_{14}H_9D_6FN_2O_3$ (284.32), Monoisotope mass: 284.14. UPLC (purity>99%): $t_R$=3.98 min $(M+H)^+$ 285.2. Chiral HPLC>99% ee ($t_R$=20.145 min). $^1$H NMR (500 MHz, $CDCl_3$) δ 1.57 (d, J=7.2 Hz, 3H), 4.76 (q, J=7.3 Hz, 1H), 6.44 (br s, 1H) 7.01 (ddd, J=10.2, 8.2, 1.0 Hz, 1H), 7.09 (td, J=7.6, 1.2 Hz, 1H), 7.21-7.26 (m, 1H), 7.31 (td, J=7.6, 1.7 Hz, 1H). $^{13}$C NMR (126 MHz, $CDCl_3$) δ 14.5, 25.7, 34.0, 49.8, 115.5, 124.5 (d, J=3.6 Hz), 129.4 (d, J=8.5 Hz), 130.2 (d, J=4.2 Hz), 168.8, 177.0.

Example 75. Compound $d_6$-(R,S)-7 (where, A=D, B=H, X=F, Y=D); (R,S)-2-(2,5-dioxopyrrolidin-1-yl-3,3,4,4-$d_4$)-N-(2-fluorophenyl)methyl-$d_2$)propanamide The compound was obtained using an analogous procedure to that described above. (R,S)-4-((1-(((2-fluorophenyl)methyl-$d_2$)amino)-1-oxopropan-2-yl)amino)-4-oxobutanoic acid-2,2,3,3-$d_4$ (3.03 g, 10 mmol, 1 eq) and $ZnCl_2$ (1.36 g, 20 mmol, 1 eq), and HMDS (2.42 g, 3.14 mL, 15 mmol, 1.5 eq) were used in the reaction. The crude product was purified by column chromatography with DCM:MeOH (9:0.3; v/v) eluents system. The compound was obtained as a solid after washing with $Et_2O$.

White solid. Yield: 84% (2.35 g); m.p. 98.3-99.8° C.; TLC: $R_f$=0.44 (DCM:MeOH (9:0.3; v/v)); $C_{14}H_9D_6FN_2O_3$ (284.32), Monoisotopic weight: 284.14 UPLC (>99% purity): $t_R$=3.98 min $(M+H)^+$ 285.2. $^1$H NMR (500 MHz, $CDCl_3$) δ 1.57 (d, J=7.2 Hz, 3H), 4.76 (q, J=7.3 Hz, 1H), 6.44 (br s, 1H) 7.01 (ddd, J=10.2, 8.2, 1.0 Hz, 1H), 7.09 (td, J=7.6, 1.2 Hz, 1H), 7.22-7.26 (m, 1H), 7.31 (td, J=7.6, 1.7 Hz, 1H). $^{13}$C NMR (126 MHz, $CDCl_3$) δ 14.5, 25.7, 34.0, 49.8, 115.5, 124.5 (d, J=3.6 Hz), 129.4 (d, J=8.5 Hz), 130.2 (d, J=4.2 Hz), 168.8, 177.0.

Example 76. Compound $d_{11}$-(R)-6 (where, A=D, B=D, X=D, Y=D); (R)-2-(2,5-dioxopyrrolidin-1-yl-3,3,4,4-$d_4$)-N-((phenyl-$d_5$)methyl-$d_2$)propanamide The compound was obtained using an analogous procedure to that described above. (R)-4-oxo-4-((1-oxo-1-(((phenyl-$d_5$) methyl-$d_2$)amino)propan-2-yl)amino)butanoic acid-2,2,3,3-$d_4$ (2.89 g, 10 mmol, 1 eq) and $ZnCl_2$ (1.36 g, 20 mmol, 1 eq), and HMDS (2.42 g, 3.14 mL, 15 mmol, 1.5 eq) were used in the reaction. The crude product was purified by column chromatography with DCM:MeOH (9:0.3; v/v) eluents system. The compound was obtained as a solid after washing with $Et_2O$.

White solid. Yield: 83% (2.40 g); m.p. 138.1-139.0° C.; TLC: $R_f$=0.39 (DCM:MeOH (9:0.3; v/v)); $C_{14}H_5D_{11}N_2O_3$ (271.36), Monoisotope mass: 271.19. UPLC (purity>99%): $t_R$=3.80 min $(M+H)^+$ 272.2. Chiral HPLC>99% ee ($t_R$=24.017 min). $^1H$ NMR (500 MHz, $CDCl_3$) δ 1.58 (d, J=7.5 Hz, 3H), 4.79 (q, J=7.5 Hz, 1H), 6.32 (br s, 1H). $^{13}C$ NMR (126 MHz, $CDCl_3$) δ 14.5, 25.7, 34.0, 49.8, 127.5, 128.5, 137.7, 168.6, 177.0.

Example 77. Compound $d_{11}$-(S)-6 (where, A=D, B=D, X=D, Y=D); (S)-2-(2,5-dioxopyrrolidin-1-yl-3,3,4,4-$d_4$)-N-((phenyl-$d_5$)methyl-$d_2$)propanamide The compound was obtained using an analogous procedure to that described above. (S)-4-oxo-4-((1-oxo-1-(((phenyl-$d_5$)methyl-$d_2$)amino)propan-2-yl)amino)butanoic acid-2,2,3,3-$d_4$ (2.89 g, 10 mmol, 1 eq) and $ZnCl_2$ (1.36 g, 20 mmol, 1 eq), and HMDS (2.42 g, 3.14 mL, 15 mmol, 1.5 eq) were used in the reaction. The crude product was purified by column chromatography with DCM:MeOH (9:0.3; v/v) eluents system. The compound was obtained as a solid after washing with $Et_2O$.

White solid. Yield: 85% (2.45 g); m.p. 138.1-139.1° C.; TLC: $R_f$=0.39 (DCM:MeOH (9:0.3; v/v)); $C_{14}H_5D_{11}N_2O_3$ (271.36), Monoisotope mass: 271.19. UPLC (purity>99%): $t_R$=3.80 min $(M+H)^+$ 272.2. Chiral HPLC>99% ee ($t_R$=26.128 min). $^1H$ NMR (500 MHz, $CDCl_3$) δ 1.58 (d, J=7.5 Hz, 3H), 4.79 (q, J=7.5 Hz, 1H), 6.32 (br s, 1H). $^{13}C$ NMR (126 MHz, $CDCl_3$) δ 14.5, 25.7, 34.0, 49.8, 127.5, 128.5, 137.7, 168.6, 177.0.

Example 78. Compound $d_{11}$-(R,S)-6 (where, A=D, B=D, X=D, Y=D); (R,S)-2-(2,5-dioxopyrrolidin-1-yl-3,3,4,4-$d_4$)-N-((phenyl-$d_5$)methyl-$d_2$)propanamide The compound was obtained using an analogous procedure to that described above. (R,S)-4-oxo-4-((1-oxo-1-(((phenyl-$d_5$)methyl-$d_2$)amino)propan-2-yl)amino)butanoic acid-2,2,3,3-$d_4$ (2.89 g, 10 mmol, 1 eq) and $ZnCl_2$ (1.36 g, 20 mmol, 1 eq), and HMDS (2.42 g, 3.14 mL, 15 mmol, 1.5 eq) were used in the reaction. The crude product was purified by column chromatography with DCM:MeOH (9:0.3; v/v) eluents system. The compound was obtained as a solid after washing with $Et_2O$.

White solid. Yield: 82% (2.37 g); m.p. 84.2-86.3° C.; TLC: $R_f$=0.39 (DCM:MeOH (9:0.3; v/v)); $C_{14}H_5D_{11}N_2O_3$ (271.36), Monoisotope mass: 271.19. UPLC (purity>99%): $t_R$=3.80 min $(M+H)^+$ 272.2. $^1H$ NMR (500 MHz, $CDCl_3$) δ 1.58 (d, J=7.5 Hz, 3H), 4.79 (q, J=7.5 Hz, 1H), 6.32 (br s, 1H). $^{13}C$ NMR (126 MHz, $CDCl_3$) δ 14.5, 25.7, 34.0, 49.8, 127.5, 128.5, 137.7, 168.6, 177.0.

Synthetic Procedure for Compound $d_4$-(R)-KA-104

The title compound was prepared according to the synthetic procedure illustrated in Scheme 2.

Scheme 2. Method for obtaining compound $d_4$-(R)-KA-104.

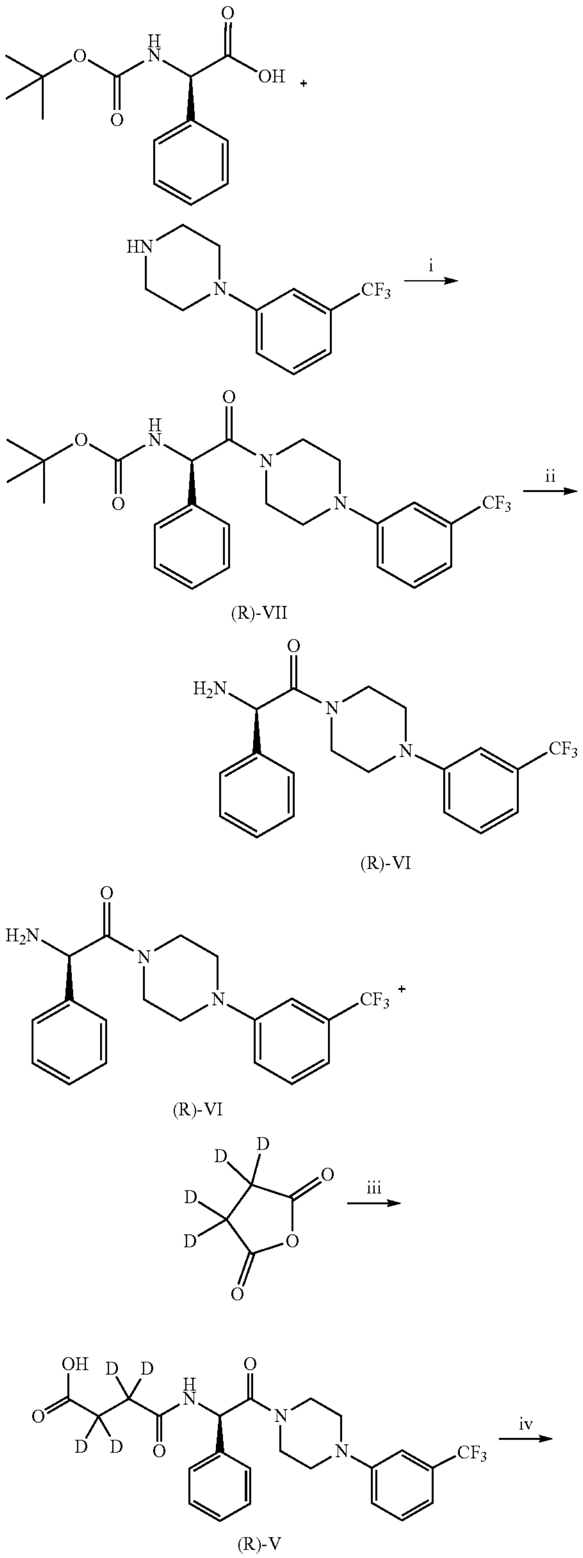

(R)-VII (R)-VI (R)-VI (R)-V

-continued

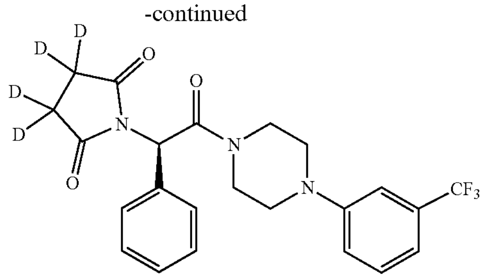

$d_4$-(R)-KA-104

Reaction conditions:
i - DCC, DCM, rt, 4 h
ii - TFA, rt, 2 h
iii - AcOEt, rt, 30 min
iv - HMDS, $ZnCl_2$, 1,4-dioxane, reflux, 24 h Example 79 Intermediate (R)-VII; tert-butyl (R)-(2-oxo-1-phenyl-2-(4-(3-(trifluoromethyl)phenyl)piperazin-1-yl)ethyl)carbamate Boc-D-phenylglycine (1.25 g, 5 mmol, 1 eq) was dissolved in 20 ml of DCM followed by the addition of DCC (1.55 g, 7.5 mmol 1.5 eq) and, after 30 minutes, 1-(3-(trifluoromethyl)phenyl)piperazine (1.15 g, 5 mmol, 1 eq). The reaction was continued with stirring at room temperature for 4 hours. After this time, DCM was distilled off to dryness. Intermediate (R)-VII was purified by column chromatography with DCM:MeOH (9:0.5; v/v) eluents system.

Colorless, clear oil. Yield: 78% (1.81 g); TLC: $R_f$=0.62 (DCM:MeOH (9:0.5; v/v)); $C_{24}H_{28}F_3N_3O_3$ (463.50), Monoisotope mass: 464.21. UPLC (purity>99%): $t_R$=8.40 min. $(M+H)^+$ 464.2.

Example 80 Intermediate (R)-VI; (R)-2-amino-2-phenyl-1-(4-(3-(trifluoromethyl)-phenyl)piperazin-1-yl)ethan-1-one 5 mL of TFA was added to the solution of tert-butyl (R)-(2-oxo-1-phenyl-2-(4-(3-(trifluoromethyl)phenyl)piperazin-1-yl)ethyl)carbamate ((R)-VI) (1.39 g, 3 mmol, 1 eq) in DCM (50 mL), and the mixture was stirred for 2 hours. Next, the reaction mixture was neutralized with a 25% $NH_4OH$ solution and then extracted with DCM (3×50 mL). The organic layer was dried over anhydrous $Na_2SO_4$ and then evaporated to dryness. (R)-2-amino-2-phenyl-1-(4-(3-(trifluoromethyl)phenyl)piperazin-1-yl)ethan-1-one was obtained as a yellow oil.

Yellow oil. Yield: 95% (1.03 g); $C_{19}H_{20}F_3N_3O$ (363.38). Monoisotope mass: 364.16. UPLC (>99% purity): $t_R$=4.96 min. $(M+H)^+$ 364.3.

Example 81 Intermediate (R)-V; (R)-4-oxo-4-((2-oxo-1-phenyl-2-(4-(3-(trifluoromethyl)phenyl)piperazin-1-yl)ethyl)amino)butanoic acid-2,2,3,3-$d_4$ Succinic anhydride-2,2,3,3-$d_4$ (0.28 g, 2.8 mmol, 1 eq) was added to the solution of (R)-2-amino-2-phenyl-1-(4-(3-(trifluoromethyl)phenyl)piperazin-1-yl)ethan-1-one ((R)-VI) (1.02 g, 2.8 mmol, 1 eq) in AcOEt (50 mL) and the reaction mixture was stirred for 30 minutes. After this time, AcOEt was distilled to dryness. The compound was obtained as a solid after washing with $Et_2O$ ether.

White solid. Yield: 87% (1.13 g); $C_{23}H_{20}D_4F_3N_3O_4$ (467.48), Monoisotope mass: 468.20. UPLC (purity>99%): $t_R$=6.40 min. $(M+H)^+$ 468.2.

Example 82 Compound $d_4$-(R)-KA-104; (R)-1-(2-oxo-1-phenyl-2-(4-(3-(trifluoromethyl)phenyl)piperazin-1-yl)ethyl)pyrrolidine-2,5-dione-3,3,4,4-$d_4$ $ZnCl_2$ (0.27 g, 2.0 mmol, 1 eq) was added to the suspension of (R)-4-oxo-4-((2-oxo-1-phenyl-2-(4-(3-(trifluoromethyl)phenyl)piperazin-1-yl)ethyl)amino)butanoic acid-2,2,3,3-$d_4$ ((R)-V) (0.93 g, 2.0 m mol, 1 eq) in anhydrous 1,4-dioxane (50 mL), the mixture was heated to 110° C. A solution of HMDS (0.48 g, 0.62 mL, 3.0 mmol, 1.5 eq) in anhydrous 1,4-dioxane (5 mL) was then added dropwise over 30 minutes. The reaction was continued with stirring at reflux for ca. 24 hours, then concentrated under reduced pressure. After distilling off the solvent, the oily residue was dissolved in DCM and extracted with 0.1 M HCl (3×50 mL), water (3×50 mL) and saturated NaCl solution (3×50 mL). The organic layer was dried over anhydrous $Na_2SO_4$ and then evaporated to dryness. The crude product was purified by column chromatography with DCM:MeOH (9:0.5; v/v) eluents system. The compound was obtained as a solid after washing with $Et_2O$ ether.

White solid. Yield: 80% (0.71 g); m.p. 189.2-190.6° C.; TLC: $R_f$=0.35 (DCM:MeOH (9:0.5; v/v)); $C_{23}H_{18}D_4F_3N_3O_3$ (449.47), Monoisotope mass: 449.19. UPLC (purity:>99%): $t_R$=6.94 min, $(M+H)^+$ 449.3. $^1H$ NMR (500 MHz, $CDCl_3$) δ 2.79 (br s, 2H), 3.02-3.18 (m, 2H), 3.24-3.41 (m, 4H), 6.11 (s, 1H), 6.97 (dd, J=8.3, 2.3 Hz, 1H), 7.01 (s, 1H), 7.09 (d, J=7.7 Hz, 1H), 7.30-7.39 (m, 5H), 7.41-7.46 (m, 1H). $^{13}C$ NMR (126 MHz, $CDCl_3$) δ 42.4, 45.6, 48.5, 48.7, 56.9, 67.2, 112.8 (d, J=3.4 Hz), 116.7 (d, J=3.4 Hz), 119.2, 124.1 (q, J=272.9 Hz), 128.7, 128.9, 129.7, 129.8, 130.9, 131.5 (q, J=32.2 Hz), 132.8, 150.8, 165.1, 176.4.

In Vivo Pharmacokinetic Studies in Mice

General Information

The experiments were carried out on male albino mice (CD-1) weighing 27-32 g, provided by an accredited animal facility. The animals were housed at a temperature of 22-24° C., humidity of 50% (+/−10%), in a room providing 15 air changes per hour, with 12:12 hours light-dark cycle. In addition, they had constant access to food and water. All procedures were performed in accordance with the applicable Polish and European guidelines on the ethics of research on animals, after obtaining the appropriate approval. Compounds tested containing deuterium ($d_4$-(R)-1, $d_9$-(R)-2, $d_4$-(R)-4, $d_6$-(R)-5, $d_{11}$-(R)-6 and $d_6$-(R)-7), and parent hydrogen-containing derivatives 1 and 2 disclosed in patent applications P.429656, PCT/PL2020/050028, and patent Pat.240297, were dissolved in a mixture of DMSO, PEG400 and water for injection (1:4:5, v/v/v) and administered i.p. to mice at two doses of 20 and 40 mg/kg. Compounds $d_5$-(R)-3, $d_3$-(R)-8, (R)-KA-104, and $d_4$-(R)-KA-104 were only administered at dose of 40 mg/kg. Compounds 2 and $d_6$-(R)-7 were also tested after intragastric administration at a dose of 40 mg/kg, as solutions in a mixture of DMSO/PEG400/water for injection (1:4:5, v/v/v). Animals were sacrificed by decapitation under isoflurane deep anesthesia at different time points, i.e. 5, 15 and 30 min. and 1, 2, 4, 6, 8, 12 and 24 hours from administration of tested compounds (n=3-4) for blood and brain collection. Blood was allowed to clot at room temperature for 20 min, then centrifuged for 5 min, 10,000×g (Eppendorf miniSpin centrifuge, Germany) to obtain serum. The obtained biological material was stored at −70° C. until analysis.

Analytical Method

Concentrations of the tested compounds in murine serum and brain homogenates were determined by high-performance liquid chromatography-tandem mass spectrometry (HPLC-MS/MS). Analyzes were performed on a Sciex QTRAP 4500 triple quad mass spectrometer coupled to an Exion LC AC HPLC (Danaher Corporation, USA). The chromatographic separation was carried out on a Hypersil Gold™ C18 column (3×50 mm, 5 μm, Thermo Scientific, USA), using a mixture of acetonitrile and water with 0.1% formic acid as the mobile phase. Analyzes were performed at 40° C. and the gradient shown in Table 7 was used to obtain optimal retention time. Valsartan was used as an internal standard. Positive ionization mode (ESI+) was used for maximum sensitivity. Ion path parameters were optimized by continuous infusion (7 μL/min) of a solution of the tested compound directly to the mass spectrometer using a syringe pump. The optimal parameters of the ion source were: ion spray voltage set at 5500 V and gas temperature set at 500° C. The curtain gas pressure was set at 20 psi and the collision gas was set to a medium. Analyst version 1.7 software was used to collect and integrate data. The calibration curves were prepared in appropriate matrices (serum or brain homogenate) in the range of 0.001 to 5 μg/mL and 0.1 to 40 μg/ml of serum and in the range of 0.004 to 20 μg/g and 0.4 to 80 μg/g of brain tissue. The calibration curves were generated by weighted (1/x·x) linear regression analysis. The calculated precision and accuracy values were within the range recommended by the FDA guidelines for the validation of bioanalytical methods. No matrix effect was observed that could significantly affect the accuracy of the assay. The determined compounds were stable during the sample preparation process and under autosampler conditions.

TABLE 7

Phase composition gradient used for determination of tested compounds in murine serum and brain homogenates.

| Time [min] | phase A [%] | phase B [%] | Flow rate [μL/min] |
|---|---|---|---|
| 0 | 5 | 95 | 400 |
| 2 | 5 | 95 | 400 |
| 4 | 95 | 5 | 400 |
| 6 | 95 | 5 | 400 |
| 6.1 | 5 | 95 | 400 |
| 10 | 5 | 95 | 400 |

phase A - 0.1% formic acid in acetonitrile;
phase B - 0.1% formic acid in water.

Preparation of Standard Solutions

Stock solutions of tested compounds were prepared in methanol at a concentration of 1 mg/mL. Working standard solutions with concentrations of 0.01 were then prepared by serial dilution of stock solutions; 0.1; 0.25; 0.5; 1; 2.5; 5; 10; 50; 100; 200 and 400 μg/ml (the effective concentrations of the calibration samples were 0.001, 0.01, 0.025, 0.05, 0.1, 0.25, 0.5, 1, 5, 10, 20 and 40 μg/mL). In order to prepare calibration curves, 5 μl of a working standard solution with specific concentration of the tested compound was added to 45 μl of the appropriate matrix (serum or brain homogenate) and mixed for 10 s. Then the samples were deproteinized with a 0.1% formic acid in acetonitrile with the addition of an internal standard (1:3 v/v), shaken for 10 min (IKA Vibrax VXR, Germany), and centrifuged for 5 min at 8000×g (Eppendorf miniSpin centrifuge, Germany). In order to determine the concentrations of the tested compounds, two calibration curves were prepared. For calibration curves ranging from 0.001 to 5 μg/mL, the supernatant was directly transferred to the chromatographic vials. In the case of the calibration curve ranging from 0.1 to 40 μg/mL, the supernatant was additionally diluted 10 times with the deproteinizing reagent before being transferred to the chromatographic vials.

Sample Preparation

The brains were homogenized in 1:4 (w/v) distilled water using a LabGen 125 tissue homogenizer (Cole Parmer, UK). Brain or serum homogenate samples (50 μL) were deproteinized with 0.1% formic acid in acetonitrile with an addition of an internal standard (1:3, v/v). The samples were then shaken for 10 min (IKA Vibrax VXR, Germany) and centrifuged for 5 min at 8000×g (Eppendorf miniSpin centrifuge, Germany). The supernatant was transferred directly to the chromatographic vials or diluted 10 times with the deproteinizing reagent. Serum samples in which the concentration of the test compound was above 40 μg/mL before deproteinization were diluted with pure matrix. The temperature of the autosampler was set to 15° C. and 1 μL was injected into the analytical column.

Pharmacokinetic Analysis

Non-compartmental analysis was used to estimate the pharmacokinetic parameters. Maximum concentration ($C_{max}$) and time necessary to reach maximum blood concentration—$t_{max}$ were evaluated directly from the concentration-time plot. The area under the concentration-time curve plotted to the last measured concentration ($AUC_{0\text{-}t}$) and to infinity ($AUC_{inf}$) was calculated using the linear trapezoid rule. The terminal slope of the concentration-time curve ($\lambda_z$) was calculated using linear regression in Excel (Microsoft Office). The terminal half-life ($t_{0.5\lambda z}$) was calculated from the relationship: $\ln 2/\lambda_z$. The volume of distribution ($V_z/F$) was calculated as: dose/($\lambda_z \cdot AUC_{0\text{-}\infty}$) and clearance (CL/F) was obtained from equation: dose/$AUC_{0\text{-}\infty}$. In these equations, F is the fraction of the absorbed dose. The mean residence time of the compound in the body (MRT) was estimated based on the equation: $AUMC_{0\text{-}\infty}/AUC_{0\text{-}\infty}$, where AUMC is the area under the first moment curve.

Evaluation of Anticonvulsant Activity and Effects on Motor Coordination in the In Vivo Studies in Mice General Information The experiments were carried out on male albino mice (CD-1) weighing 25-30 g, provided by an accredited animal facility. All procedures were performed in accordance with the applicable Polish and European guidelines on the ethics of research on animals, after obtaining the appropriate approval. The substances were administered intraperitoneally after prior dissolution in a mixture of DMSO, PEG400 and water for injection (1:4:5, v/v/v) as single injections of 0.1 mL/10 g b.w., 30 minutes and 2 h before the given test. Initial screening was performed on groups of 4 mice. The mean effective dose ($ED_{50}$) in a given test and the neurotoxic dose in the rotarod test ($TD_{50}$) were estimated on the basis of the results obtained on 3-4 groups of animals consisting of 6 animals.

Maximal Electroshock Seizure Test

In the maximal electroshock seizure test (MES), the seizures were induced by 500 V, 25 mA electrical stimulus of 0.2 s in duration. The electrical pulse was generated using an electric shock generator (Rodent shocker, Type 221, Hugo Sachs Elektronik, Germany) and delivered to the animal using electrodes placed on the auricles. The study was conducted 30 minutes/2 hours after intraperitoneal administration of the compounds at various doses. During the experiment, the number of animals that experienced a seizure episode in the form of hindlimb tonic extension was counted (Łuszczki, J.J. et al. *Fundam. Clin. Pharmacol.* 2008, 22, 69-74).

Psychomotor Seizure Test (6 Hz Test)

In the psychomotor seizure test (6 Hz test), seizures were induced by a 32 mA and/or 44 mA electrical stimulus of a frequency of 6 pulses per second. An electrical pulse was generated using an electric shock generator (ECT Unit 57800; Ugo Basile, Gemonio, Italy) and delivered to the animal using corneal electrodes. Before starting the test, the eye surface was gently moistened with a solution of local anesthetic (1% lidocaine solution). The study was conducted 30 minutes/2 hours after intraperitoneal administration of the compounds at various doses. An electrical stimulus was delivered continuously for a period of 3 seconds, followed by observation of the animal for a period of 10 seconds. During the experiment, the number of animals with an episode of psychomotor convulsions was counted: motor inhibition, staggering, maintaining a sitting posture, forelimb clonus, twitching of the vibrissae and Straub-tail were observed (Leclercq, K.; Kaminski, R. M. *Epilepsia* 2015, 56, 310-318).

Subsutaneous Pentylenetetrazole (scPTZ) Seizure Test

In the subsutaneous pentylenetetrazole seizure test, the animals received pentylenetetrazole at a dose of 100 mg/kg. Test compounds were administered 30 minutes and 2 hours before the experiment. After PTZ administration, the animals were placed individually in transparent cages and observed for a period of 30 minutes/2 hours. During the experiment, the number of animals with a clonic seizure lasting at least 3 s with loss of balance was counted. In addition, the latency of the onset of the first clonic seizure was measured and compared with the control group (Ferreri, G. et al. *Pharmacol. Biochem. Behav.* 2004, 77, 859-894; Łączkowski, K. et. al. *J. Enzym Inhib. Med. Chem.* 2016, 31, 1576-1582).

Influence on Mouse Coordination in the Rotarod Test

The effect of the tested compounds on motor coordination was assessed in the rotarod test (May Commat, RR 0711 RotaRod, Turkey). The day before the actual experiment, the mice were trained on a rod rotating at 10 revolutions per minute (rpm) for 3 minutes. The experiment was performed 30 minutes and 2 hours after administration of the compounds. The motor coordination of the animals was tested at the speed of the rotating rod: 10 rpm for 60 seconds. The measure of neurotoxicity was the inability to stay on the rod for a given time (Łuszczki, J.J. et al. *Eur. Neuropsychopharmacol.* 2005, 6, 609-616).

Statistical Analysis

The $ED_{50}$ (effective dose) and $TD_{50}$ (toxic dose) values along with the corresponding 95% confidence limits were calculated based on the Litchfield and Wilcoxon method (Litchfield, J. T.; Wilcoxon, F. J. *Pharmacol. Exp. Ther.* 1949, 96, 99-113). To perform a statistical evaluation of the results in the scPTZ test, one-way ANOVA variance analysis followed by Dunnett's post hoc test were used. The values were considered statistically significant if $p<0.05$.

Evaluation of Antinociceptive Activity and the Effect on Spontaneous Locomotor Activity in In Vivo Studies on Mice General Information The experiments were carried out on male albino mice (CD-1) weighing 25-30 g, provided by an accredited animal facility. All procedures were performed in accordance with the applicable Polish and European guidelines on the ethics of research on animals, after obtaining the appropriate approval. The substance was administered intraperitoneally after suspension in a 1% Tween 80 solution, as single injections of 0.1 mL/10 g b.w., 30 minutes before a given test.

Anti-Nociceptive Activity

All tests/models were performed based on procedures described in the specialist literature: formalin test (Beirith et al. *Eur. J. Pharmacol.* 1998, 345, 233-245), capsaicin-induced pain model (Mogilski et al. *Pharmacol. Biochem. Behav.* 2015, 133, 99-110), oxaliplatin-induced neuropathic pain model—von Frey's test (Sałat et al. *Pharmacol. Biochem. Behav.* 2014, 122, 173-181), streptozotocin-induced diabetic neuropathic pain model—von Frey's test (Sałat et al. *Neuropharmacology* 2017, 125, 181-188; Tanabe et al. *J. Pharmacol. Sci.* 2008, 107, 213-220). The test group consisted of 8-10 animals.

Spontanouus Locomotor Activity Test in Mice

The assessment of the influence of the tested compound on the spontaneous locomotor activity of animals (assessment of the sedative or activating effect) was carried out in accordance with the methodology described in the scientific literature (Mogilski et al. Inflamm. Res. 2017, 66, 79-95), using a cage with dimensions 40×40×31 cm (Activity Cage; Ugo Basile, Gemonio VA, Italy). The compound was administered 30 minutes before the experiment. The number of light beam crossings was counted in each group during the next 30 min at 10-minute intervals. The study group consisted of 10 animals.

Evaluation of Metabolic Stability on Mouse Microsomes

Metabolic stability assessment was performed using mouse (MLMs) and human (HLMs) liver microsomes purchased from Sigma-Aldrich (St. Louis, MO, USA). The detailed methodology is described in the literature (Kamiński et al. *J. Med. Chem.* 2015, 58, 5274-5286). The reaction mixture was prepared by mixing 50 mM of the tested compound with mouse or human microsomes (1 mg/mL) in 10 mM TRIS-HCl buffer. The reaction mixture was pre-incubated for 5 min at 37° C. After the initial incubation, 50 μL of the NADPH Regeneration System (Promega, Madison, WI, USA) was added to initiate the reaction. The reaction mixture was then incubated for 120 min at 37° C. 200 μL of cold extra pure methanol was added to complete the reaction. The mixture was then centrifuged at 14,000 g for 15 min and the supernatants were analyzed using a Waters ACQUITY™ TQD LC/MS system with a TQ detector (Waters, Milford, USA). Each experiment was performed in triplicate.

The invention claimed is:

1. Compound of formula (I):

(I)

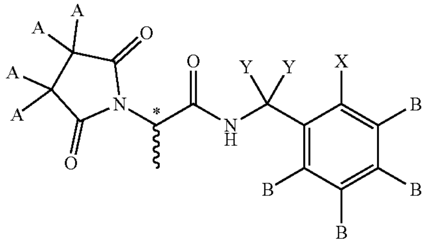

where:

A is hydrogen or deuterium, wherein at least one A is deuterium,

B is hydrogen or deuterium,

X is hydrogen or deuterium or fluorine, and

Y is hydrogen or deuterium.

2. The compound according to claim 1, characterized in that it is selected from the group consisting of:

(R)—N-benzyl-2-(2,5-dioxopyrrolidin-1-yl-3,3,4,4-$d_4$) propanamide, (R)-2-(2,5-dioxopyrrolidin-1-yl-3,3,4,4-$d_4$)-N-((phenyl-$d_5$)methyl)propanamide, (R)-2-(2,5-dioxopyrrolidin-1-yl-3,3,4,4-$d_4$)-N-(phenylmethyl-$d_2$)propanamide, (R)-2-(2,5-dioxopyrrolidin-1-yl-3,3,4,4-$d_4$)-N-((phenyl-$d_5$)methyl-$d_2$)propanamide, (R)-2-(2,5-dioxopyrrolidin-1-yl-3,3,4,4-$d_4$)-N-((2-fluorophenyl)methyl-$d_2$)propanamide, (R)-2-(2,5-dioxopyrrolidin-1-yl-3,3,4,4-$d_4$)-N-(2-fluorobenzyl)propanamide, (S)-N-benzyl-2-(2,5-dioxopyrrolidin-1-yl-3,3,4,4-$d_4$)propanamide, (S)-2-(2,5-dioxopyrrolidin-1-yl-3,3,4,4-$d_4$)-N-((phenyl-$d_5$)methyl)propanamide, (S)-2-(2,5-dioxopyrrolidin-1-yl-3,3,4,4-$d_4$)-N-(2-fluorobenzyl)propanamide, (S)-2-(2,5-dioxopyrrolidin-1-yl-3,3,4,4-$d_4$)-N-(phenylmethyl-$d_2$)propanamide, (S)-2-(2,5-dioxopyrrolidin-1-yl-3,3,4,4-$d_4$)-N-((phenyl-$d_5$)methyl-$d_2$)propanamide, (S)-2-(2,5-dioxopyrrolidin-1-yl-3,3,4,4-$d_4$)-N-((2-fluorophenyl)methyl-$d_2$)propanamide, (R,S)—N-benzyl-2-(2,5-dioxopyrrolidin-1-yl-3,3,4,4-$d_4$) propanamide, (R,S)-2-(2,5-dioxopyrrolidin-1-yl-3,3,4,4-$d_4$)-N-((phenyl-$d_5$)methyl)propanamide, (R,S)-2-(2,5-dioxopyrrolidin-1-yl-3,3,4,4-$d_4$)-N-(2-fluorobenzyl)propanamide, (R,S)-2-(2,5-dioxopyrrolidin-1-yl-3,3,4,4-$d_4$)-N-(phenylmethyl-$d_2$)propanamide, (R,S)-2-(2,5-dioxopyrrolidin-1-yl-3,3,4,4-$d_4$)-N-((phenyl-$d_2$)methyl-$d_2$)propanamide, and (R,S)-2-(2,5-dioxopyrrolidin-1-yl-3,3,4,4-$d_4$)-N-((2-fluorophenyl)methyl-$d_2$)propanamide.

3. The compound according to claim 1, wherein the compound is (R)—N-benzyl-2-(2,5-dioxopyrrolidin-1-yl-3,3,4,4-$d_4$)propanamide.

4. The compound according to claim 1, wherein the compound is (R)-2-(2,5-dioxopyrrolidin-1-yl-3,3,4,4-$d_4$)-N-((phenyl-$d_5$)methyl)propanamide.

5. The compound according to claim 1, wherein the compound is (R)-2-(2,5-dioxopyrrolidin-1-yl-3,3,4,4-$d_4$)-N-(2-fluorobenzyl)propanamide.

6. The compound according to claim 1, wherein the compound is (R)-2-(2,5-dioxopyrrolidin-1-yl-3,3,4,4-$d_4$)-N-(phenylmethyl-$d_2$)propanamide.

7. The compound according to claim 1, wherein the compound is (R)-2-(2,5-dioxopyrrolidin-1-yl-3,3,4,4-$d_4$)-N-((phenyl-$d_5$)methyl-$d_2$)propanamide.

8. The compound according to claim 1, wherein the compound is (R)-2-(2,5-dioxopyrrolidin-1-yl-3,3,4,4-$d_4$)-N-((2-fluorophenyl)methyl-$d_2$)propanamide.

9. The compound according to claim 1, wherein each A is deuterium.

10. The compound according to claim 1, wherein X is hydrogen or deuterium.

11. The compound according to claim 1, wherein the compound is (S)—N-benzyl-2-(2,5-dioxopyrrolidin-1-yl-3,3,4,4-$d_4$)propanamide.

12. The compound according to claim 1, wherein the compound is (S)-2-(2,5-dioxopyrrolidin-1-yl-3,3,4,4-$d_4$)-N-((phenyl-$d_5$)methyl)propanamide.

13. The compound according to claim 1, wherein the compound is (S)-2-(2,5-dioxopyrrolidin-1-yl-3,3,4,4-$d_4$)-N-(2-fluorobenzyl)propanamide.

14. The compound according to claim 1, wherein the compound is (S)-2-(2,5-dioxopyrrolidin-1-yl-3,3,4,4-$d_4$)-N-(phenylmethyl-$d_2$)propanamide.

15. The compound according to claim 1, wherein the compound is (S)-2-(2,5-dioxopyrrolidin-1-yl-3,3,4,4-$d_4$)-N-((phenyl-$d_5$)methyl-$d_2$)propanamide.

16. The compound according to claim 1, wherein the compound is (S)-2-(2,5-dioxopyrrolidin-1-yl-3,3,4,4-$d_4$)-N-((2-fluorophenyl)methyl-$d_2$)propanamide.

17. The compound according to claim 1, wherein the compound is (R,S)—N-benzyl-2-(2,5-dioxopyrrolidin-1-yl-3,3,4,4-$d_4$)propanamide.

18. The compound according to claim 1, wherein the compound is (R,S)-2-(2,5-dioxopyrrolidin-1-yl-3,3,4,4-$d_4$)-N-((phenyl-$d_5$)methyl)propanamide.

19. The compound according to claim 1, wherein the compound is (R,S)-2-(2,5-dioxopyrrolidin-1-yl-3,3,4,4-$d_4$)-N-(2-fluorobenzyl)propanamide.

20. The compound according to claim 1, wherein the compound is (R,S)-2-(2,5-dioxopyrrolidin-1-yl-3,3,4,4-$d_4$)-N-(phenylmethyl-$d_2$)propanamide.

21. The compound according to claim 1, wherein the compound is (R,S)-2-(2,5-dioxopyrrolidin-1-yl-3,3,4,4-$d_4$)-N-((phenyl-$d_5$)methyl-$d_2$)propanamide.

22. The compound according to claim 1, wherein the compound is (R,S)-2-(2,5-dioxopyrrolidin-1-yl-3,3,4,4-$d_4$)-N-((2-fluorophenyl)methyl-$d_2$)propanamide.

* * * * *